US011992538B2

(12) United States Patent
Riedel et al.

(10) Patent No.: US 11,992,538 B2
(45) Date of Patent: May 28, 2024

(54) POLYMERIZABLE DENTAL COMPOSITION BASED ON CONDENSED SILANES

(71) Applicant: VOCO GmbH, Cuxhaven (DE)

(72) Inventors: Silke Riedel, Cuxhaven (DE); Gerrit Lübbe, Cuxhaven (DE); Manfred Thomas Plaumann, Cuxhaven (DE)

(73) Assignee: VOCO GMBH, Cuxhaven (DE)

( * ) Notice: Subject to any disclaimer, the term of this patent is extended or adjusted under 35 U.S.C. 154(b) by 940 days.

(21) Appl. No.: 16/995,394

(22) Filed: Aug. 17, 2020

(65) Prior Publication Data

US 2021/0052469 A1 Feb. 25, 2021

(30) Foreign Application Priority Data

Aug. 19, 2019 (DE) .................. 102019122174.9

(51) Int. Cl.
| | |
|---|---|
| *A61K 6/16* | (2020.01) |
| *A61K 6/60* | (2020.01) |
| *A61K 6/76* | (2020.01) |
| *A61K 6/77* | (2020.01) |
| *A61K 6/887* | (2020.01) |
| *C08L 83/04* | (2006.01) |

(52) U.S. Cl.
CPC .................. *A61K 6/16* (2020.01); *A61K 6/60* (2020.01); *A61K 6/76* (2020.01); *A61K 6/77* (2020.01); *A61K 6/887* (2020.01); *C08L 83/04* (2013.01)

(58) Field of Classification Search
CPC . A61K 6/16; A61K 6/77; A61K 6/887; A61K 6/76; A61K 6/60; C08L 83/04; A61C 13/087; A61C 5/77; A61C 13/0003; A61C 19/003; A61C 5/30; A61C 13/00; A61C 5/00; A61C 13/09; A61C 13/08
USPC ...................................................... 433/228.1
See application file for complete search history.

(56) References Cited

U.S. PATENT DOCUMENTS

| | | |
|---|---|---|
| 3,347,954 A | 10/1967 | Hellmut et al. |
| 4,243,692 A | 1/1981 | Scholze et al. |
| 4,298,738 A | 11/1981 | Lechtken et al. |
| 4,443,587 A | 4/1984 | Schmitt et al. |
| 4,447,520 A | 5/1984 | Henne et al. |
| 4,493,911 A | 1/1985 | Schmitt et al. |
| 4,522,693 A | 6/1985 | Henne et al. |
| 4,737,593 A | 4/1988 | Ellrich et al. |
| 4,772,530 A | 9/1988 | Gottschalk et al. |
| 4,868,091 A | 9/1989 | Boettcher et al. |
| 4,874,450 A | 10/1989 | Gottschalk |
| 4,954,414 A | 9/1990 | Adair et al. |
| 5,002,769 A | 3/1991 | Friedman |
| 5,008,303 A | 4/1991 | Gasser et al. |
| 5,055,372 A | 10/1991 | Shanklin et al. |
| 5,057,393 A | 10/1991 | Shanklin et al. |
| 5,063,257 A | 11/1991 | Akahane et al. |
| 5,100,929 A | 3/1992 | Jochum et al. |
| 5,236,362 A | 8/1993 | Cohen et al. |
| 5,399,770 A | 3/1995 | Leppard et al. |
| 5,472,991 A | 12/1995 | Schmitt et al. |
| 5,717,125 A | 2/1998 | Wolter et al. |
| 5,767,169 A | 6/1998 | Leppard et al. |
| 5,847,025 A | 12/1998 | Moszner et al. |
| 5,877,232 A * | 3/1999 | Storch ...................... A61K 6/20 526/279 |
| 5,984,683 A | 11/1999 | Sakata et al. |
| 6,020,528 A | 2/2000 | Leppard et al. |
| 6,084,004 A | 7/2000 | Weinmann et al. |
| 6,127,449 A | 10/2000 | Bissinger et al. |
| 6,136,886 A | 10/2000 | Deguchi |
| 6,196,843 B1 | 3/2001 | Kawaguchi et al. |
| 6,245,828 B1 | 6/2001 | Weinmann et al. |
| 6,288,138 B1 | 9/2001 | Yamamoto et al. |
| 6,566,413 B1 | 5/2003 | Weinmann et al. |
| 6,613,812 B2 | 9/2003 | Bui et al. |
| 6,624,236 B1 | 9/2003 | Bissinger et al. |
| 6,642,286 B2 | 11/2003 | Nakayama et al. |
| 6,833,425 B1 | 12/2004 | Hecht et al. |
| 6,852,775 B1 | 2/2005 | Soglowek et al. |
| 6,936,642 B2 | 8/2005 | Lehmann et al. |

(Continued)

FOREIGN PATENT DOCUMENTS

| | | | |
|---|---|---|---|
| BE | 450140 A | * | 1/2020 |
| CA | 2296227 A1 | | 7/2000 |

(Continued)

OTHER PUBLICATIONS

Megan A. Cole et al: "Thiol-ene functionalized siloxanes for use as elastomeric dental impression materials", Dental Materials, Bd. 30, Nr. 4, 1. Apr. 2014 (Apr. 1, 2014), Seiten 449-455, XP055743888, Amsterdam, NL ISSN: 0109-5641, DOI: 10.1016/j.dental. 2014.01. 11.*
Cole, Megan A. et al., "Thiol-Ene functionalized siloxanes for use as elastomeric dental impression materials," Dent Mater, 30(4): 449-455 (2014).
Search Report issued for related European Application No. 20190855. 5, dated Nov. 11, 2020 (4 pages).
Search Report issued for related German Application No. 102019122174.9, dated Jan. 13, 2021 (7 pages).
Dadashi-Silab et al., "Photoinduced Electron Transfer Reactions for macromolecular Synthesis" Chemical Reviews, 116(17): 10212-10275 (2016).

(Continued)

*Primary Examiner* — Matthew M Nelson
(74) *Attorney, Agent, or Firm* — Armstrong Teasdale LLP

(57) ABSTRACT

The present invention relates to novel polymerizable dental compositions comprising, (A) polysiloxanes, wherein the polysiloxanes comprise a mixture of the condensates of the three silanes (a1), (a2) and (a3) and/or a cocondensate of a mixture of the three silanes (a1), (a2) and (a3) and/or a mixture of at least two of the cocondensates (a1)/(a2), (a1)/(a3) and (a2)/(a3) and/or a mixture of the condensate of one of the three silanes (a1), (a2) or (a3) with the cocondensate of the other two silanes, (B) fillers and (C) initiators and/or catalysts and/or activators for the polymerization.

20 Claims, No Drawings

(56) References Cited

U.S. PATENT DOCUMENTS

| | | | |
|---|---|---|---|
| 6,953,535 B2 | 10/2005 | Hecht et al. | |
| 7,081,485 B2 | 7/2006 | Suh et al. | |
| 7,148,382 B2 | 12/2006 | Wolf et al. | |
| 7,214,726 B2 | 5/2007 | Qian | |
| 7,276,545 B2 | 10/2007 | Eckhardt et al. | |
| 7,488,762 B2 | 2/2009 | Takano et al. | |
| 7,605,190 B2 | 10/2009 | Moszner et al. | |
| 7,879,924 B2 | 2/2011 | Torii et al. | |
| 7,932,414 B2 | 4/2011 | Wolter | |
| 7,989,519 B2 | 8/2011 | Vogt et al. | |
| 8,076,441 B2 | 12/2011 | Wolter | |
| 8,129,444 B2 | 3/2012 | Hecht et al. | |
| 8,501,834 B2 | 8/2013 | Maletz et al. | |
| 8,669,302 B2 | 3/2014 | Blomker et al. | |
| 8,697,769 B2 | 4/2014 | Blomker et al. | |
| 8,697,772 B2 | 4/2014 | Blomker et al. | |
| 8,883,876 B2 | 11/2014 | Lueck | |
| 8,889,758 B2 | 11/2014 | Moszner et al. | |
| 8,915,736 B2 | 12/2014 | Blomker et al. | |
| 9,023,916 B2 | 5/2015 | Blomker et al. | |
| 9,079,828 B2 | 7/2015 | Blomker et al. | |
| 9,206,205 B2 | 12/2015 | Wolter et al. | |
| 9,233,992 B2 | 1/2016 | Wolter et al. | |
| 9,314,408 B2 | 4/2016 | Blomker et al. | |
| 9,326,917 B2 | 5/2016 | Maletz et al. | |
| 9,474,697 B2 * | 10/2016 | Riedel | A61C 9/0006 |
| 9,532,931 B2 | 1/2017 | Lubbe | |
| 9,770,528 B2 | 9/2017 | Kilway et al. | |
| 9,795,541 B2 | 10/2017 | Fontein et al. | |
| 9,839,585 B2 * | 12/2017 | Fontein | A61K 6/887 |
| 10,342,744 B2 | 7/2019 | Moszner et al. | |
| 2004/0185009 A1 | 9/2004 | Penhasi et al. | |
| 2007/0027229 A1 | 2/2007 | Moszner et al. | |
| 2007/0142495 A1 | 6/2007 | Neffgen et al. | |
| 2008/0300340 A1 * | 12/2008 | Gross | A61K 6/893 523/120 |
| 2011/0071234 A1 * | 3/2011 | Gross | A61K 6/887 523/116 |
| 2011/0082232 A1 * | 4/2011 | Gross | A61K 6/887 523/115 |
| 2012/0123012 A1 | 5/2012 | Rheinberger et al. | |
| 2015/0080490 A1 * | 3/2015 | Burtscher | A61K 6/889 522/18 |
| 2015/0299469 A1 | 10/2015 | Takada et al. | |
| 2016/0128909 A1 * | 5/2016 | Fontein | A61K 6/887 523/116 |
| 2016/0128911 A1 * | 5/2016 | Fontein | A61K 6/887 523/116 |
| 2018/0369075 A1 | 12/2018 | Moszner et al. | |
| 2019/0010172 A1 * | 1/2019 | Moszner | A61K 6/853 |
| 2019/0256533 A1 * | 8/2019 | Shuto | C07F 7/0838 |
| 2021/0052469 A1 * | 2/2021 | Riedel | C08L 83/06 |

FOREIGN PATENT DOCUMENTS

| | | | |
|---|---|---|---|
| CA | 2202732 C * | 7/2001 | A61K 6/083 |
| CA | 2368323 A1 | 7/2002 | |
| DE | 1495520 A1 | 4/1969 | |
| DE | 2420351 A1 | 11/1974 | |
| DE | 2758414 A1 | 7/1979 | |
| DE | 3236026 A1 | 3/1984 | |
| DE | 3246654 A1 | 6/1984 | |
| DE | 3941629 A1 | 6/1990 | |
| DE | 3902417 A1 | 8/1990 | |
| DE | 4133494 A1 | 4/1993 | |
| DE | 4416857 C1 | 6/1995 | |
| DE | 69017484 T2 | 7/1995 | |
| DE | 3941629 C2 | 11/1995 | |
| DE | 3801511 C2 | 11/1996 | |
| DE | 19708294 A1 | 9/1997 | |
| DE | 19648283 A1 | 5/1998 | |
| DE | 19754029 A1 | 6/1998 | |
| DE | 19711514 B4 | 9/1998 | |
| DE | 19860361 A1 | 6/2000 | |
| DE | 19903177 A1 | 7/2000 | |
| DE | 69231737 T2 | 8/2001 | |
| DE | 19860364 C2 | 12/2001 | |
| DE | 69801010 T2 | 3/2002 | |
| DE | 10147125 A1 | 4/2002 | |
| DE | 10102297 A1 | 8/2002 | |
| DE | 10119831 A1 | 10/2002 | |
| DE | 4231579 C2 | 11/2002 | |
| DE | 10126476 A1 | 12/2002 | |
| DE | 19961341 C2 | 9/2003 | |
| DE | 19941738 B4 | 2/2004 | |
| DE | 29924636 U1 * | 7/2004 | A61K 6/0017 |
| DE | 69725380 T2 | 8/2004 | |
| DE | 69921231 T2 | 10/2005 | |
| DE | 60116142 T2 | 7/2006 | |
| DE | 102006019092 A1 | 3/2007 | |
| DE | 60029481 T2 | 7/2007 | |
| DE | 102006016474 A1 | 10/2007 | |
| DE | 102006050153 A1 | 5/2008 | |
| DE | 602004009552 T2 | 7/2008 | |
| DE | 102007050763 A1 | 4/2009 | |
| DE | 202010014676 U1 | 12/2010 | |
| DE | 102014210432 A1 | 12/2015 | |
| DE | 102014210432 A1 * | 12/2015 | A61K 6/0088 |
| DE | 102014116389 A1 | 5/2016 | |
| DE | 102014116402 A1 | 5/2016 | |
| DE | 112006001049 B4 | 4/2017 | |
| DE | 102019122174 A1 * | 2/2021 | A61K 6/16 |
| EP | 0007508 A2 | 2/1980 | |
| EP | 0047902 A2 | 3/1982 | |
| EP | 0057474 A2 | 8/1982 | |
| EP | 0059451 A1 | 9/1982 | |
| EP | 0073413 A2 | 3/1983 | |
| EP | 0173567 A2 | 3/1986 | |
| EP | 0184095 A2 | 6/1986 | |
| EP | 0285133 A2 | 10/1988 | |
| EP | 0262629 B1 | 4/1991 | |
| EP | 0366977 B1 | 3/1993 | |
| EP | 0807853 A2 | 11/1997 | |
| EP | 0897710 A2 | 2/1999 | |
| EP | 0948955 A1 | 10/1999 | |
| EP | 1194110 B1 | 4/2002 | |
| EP | 0948955 B1 | 9/2003 | |
| EP | 0980682 B1 | 11/2003 | |
| EP | 0783880 B1 | 8/2004 | |
| EP | 1563821 A1 | 8/2005 | |
| EP | 1236459 B1 | 11/2005 | |
| EP | 1839640 A2 | 10/2007 | |
| EP | 1685182 B1 | 12/2007 | |
| EP | 1872767 A1 | 1/2008 | |
| EP | 1881010 A1 | 1/2008 | |
| EP | 1905415 A1 | 4/2008 | |
| EP | 1720506 B1 | 11/2008 | |
| EP | 2070506 A1 | 6/2009 | |
| EP | 2070935 A1 | 6/2009 | |
| EP | 2133064 A1 | 12/2009 | |
| EP | 1874847 B1 | 2/2011 | |
| EP | 2436363 A2 | 4/2012 | |
| EP | 2436364 A2 | 4/2012 | |
| EP | 2436365 A2 | 4/2012 | |
| EP | 2436366 A2 | 4/2012 | |
| EP | 2436668 A1 | 4/2012 | |
| EP | 2450025 A1 | 5/2012 | |
| EP | 2374445 B1 | 7/2015 | |
| EP | 2748206 B1 | 9/2015 | |
| EP | 2965742 A1 | 1/2016 | |
| EP | 3090722 A1 | 11/2016 | |
| EP | 2916801 B1 | 2/2017 | |
| EP | 2374444 B1 | 3/2017 | |
| EP | 3046962 B1 | 5/2018 | |
| EP | 3058014 B1 | 6/2018 | |
| EP | 2931756 B1 | 8/2018 | |
| EP | 3166569 B1 | 11/2018 | |
| EP | 3424983 A1 * | 1/2019 | A61K 6/15 |
| EP | 2623086 B1 | 7/2019 | |
| EP | 2623087 B1 | 7/2019 | |
| JP | H08311115 A | 11/1996 | |
| JP | 2000212018 A * | 8/2000 | A61K 6/0017 |
| JP | 3157278 B2 * | 4/2001 | |

(56) References Cited

FOREIGN PATENT DOCUMENTS

| | | |
|---|---|---|
| JP | 3437881 B2 * | 8/2003 |
| JP | 2016034912 A | 3/2016 |
| WO | 2002085974 A1 | 10/2002 |
| WO | 2002092021 A1 | 11/2002 |
| WO | 2002092023 A1 | 11/2002 |
| WO | 2005011621 A1 | 2/2005 |
| WO | 2005051332 A1 | 6/2005 |
| WO | 2012091154 A1 | 7/2012 |
| WO | 2013041723 A1 | 3/2013 |
| WO | 2013053693 A1 | 4/2013 |

OTHER PUBLICATIONS

Huck-Jones et al., "Chemische Identität einzelner Partikel" [Chemical Identity of Individual Particles], in Nachrichten aus der Chemie, 62: 886-887 (2014).

Ilie et al., "Investigations on mechanical behaviour of dental composites," Clinical Oral Investigations, 13(4): 427-438 (2009).

Watts et al. "Determination of polymerization kinetics in visible light cured materials: Methods development," Dental Materials 7(4): 281-287 (1991).

* cited by examiner

POLYMERIZABLE DENTAL COMPOSITION BASED ON CONDENSED SILANES

CROSS-REFERENCE TO RELATED APPLICATIONS

This application claims priority to German Patent Application No. 102019122174.9, filed on Aug. 19, 2019, which is herein incorporated by reference in its entirety.

BACKGROUND OF THE DISCLOSURE

Polysiloxane compounds have long been known and are obtainable, for example, by hydrolysis and condensation of silanes having hydrolyzable groups (see, for example, DE 27 58 414 A1) or by hydrosilylation of allyl or vinyl compounds with SiH-containing compounds. Polysiloxane compounds can be processed further to give a multitude of products, for example overlayers, coatings, membranes or bulk materials. This further processing is frequently based on a crosslinking reaction of organically polymerizable groups in the polysiloxane compounds (e.g. (meth)acrylate groups) and the resulting formation of crosslinked polysiloxane compounds.

A specific group of polysiloxane compounds contains, in the organic groups (side chains), besides an organically polymerizable group, additional free polar functional groups, for example hydroxyl or carboxyl groups.

For instance, DE 44 16 857 C1 relates to hydrolyzable and polymerizable silanes, to processes for preparation thereof and to the use thereof for production of silica (hetero) polycondensates and (hetero)polymers. Hydrolyzable, organically modified silanes find wide use in the production of scratch-resistant coatings for a wide variety of different substrates, for the production of fillers, of adhesives and sealing compounds or of shaped bodies.

DE 44 16 857 C1 discloses the use of silica (hetero) polycondensates (polysiloxane compounds) in curable dental materials. The polysiloxane compounds described here comprise free polar functional groups (e.g. carboxyl or hydroxyl groups) capable of complexing suitable metal ions/transition metal ions (e.g. ions of titanium, zirconium or tin). In curable dental compositions, this can have a positive effect on x-ray opacity, on contact toxicity and on the refractive index of a corresponding curable or cured dental material.

DE 198 60 364 C2 relates to polymerizable dental compositions based on siloxane compounds that are capable of curing and to the use and production thereof. This publication describes the preparation of cyclic polysiloxanes and the use thereof as a basis for polymerizable dental compositions. In spite of high density of groups capable of polymerization, they are said to have a low viscosity which enables high filler loading, which leads to compositions having low polymerization shrinkage. Here too, free polar functions are present as well as the polymerizable units in the organic side chains of the polysiloxanes described.

The free polar functional groups, for example in the aforementioned polysiloxane compounds, however, regularly lead to undesired properties. For instance, it has been found that the hydrophilicity of the polysiloxane compounds caused by the (free) polar functional groups leads to increased water sorption in the presence of moisture, which reduces the wet strength of the curable dental material in a disadvantageous manner. Probably due to the formation of internal hydrogen bonds, there is an increase in viscosity. This then has an adverse effect on handling in the production of the curable dental compositions.

There is a considerable need on the part of dental practitioners and the dental industry to adapt polysiloxane compounds further to the demands on a modern (curable or cured) dental material and to minimize the aforementioned disadvantages. Polysiloxane compounds adapted in such a way should have improved physical properties for dental purposes (i.e. lead to dentally improved physical properties of the corresponding curable/cured dental materials), for example lower polymerization shrinkage on polymerization/crosslinking of the polysiloxane compounds (i.e. on curing), increased strength and/or limited water sorption with simultaneously comfortable consistency of the curable dental material.

The first successes in the improvement of the polysiloxanes were achieved through addition or substitution of different substrates onto the free polar functionalities of the above-described specific polysiloxanes.

EP 1 874 847 B1 relates to a process for preparing silanes having two, three or even more structural units linked together by a urethane-, acid amide- and/or carboxylic ester-containing bridge, each of which contains at least one organically polymerizable residue and at least one silyl radical. These silanes should especially be suitable for modification of the properties of silicic acid (hetero)polycondensates and silyl-containing organic polymers. The process disclosed should also be suitable for bridging of already precondensed silicic acid (hetero)polycondensates.

The silicic acid (hetero)polycondensates (polysiloxane compounds) disclosed in EP 1 874 847 B1 have a free hydroxyl group (i.e. a free polar functional group). These free hydroxyl groups can react with a dicarboxylic acid derivative or diisocyanate such that hydroxyl groups form a link (bridge) with a dicarboxylic acid derivative or diisocyanate. Such linked polysiloxane compounds have a much higher molecular weight without any significant reduction in the double bond density (as a result of the organically polymerizable (meth)acrylate groups). Double bond density is understood here to mean the quotient of the number of polymerizable double bonds in a compound and the molecular weight of this compound. The higher molecular weight has a positive effect on biocompatibility and polymerization shrinkage during crosslinking of the linked polysiloxane compounds. At the same time, the hydrophobicity of the polysiloxane compounds was increased. However, it has been found that the higher molecular weight has an adverse effect on the viscosity of the linked polysiloxane compounds (and hence on processibility in manufacturing the curable dental material). The viscosity increases markedly with the degree of crosslinking, i.e. with the molecular weight, such that there is no longer satisfactorily tolerable processibility in manufacturing a corresponding curable dental material comprising such linked polysiloxane compounds, even at quite a low degree of linkage.

EP 1 685 182 B1 relates to silanes and silicic acid polycondensates and partial condensates formed therefrom, in which an organic radical bonded to a silicon is present, which is branched and bears an independently organically polymerizable group at each of the two branches, or bears such a group at one of the two branches and has a radical having a further silicon atom at the other.

The polysiloxane compounds disclosed in EP 1 685 182 B1 also comprise free polar functional groups in the form of hydroxyl groups. By reaction of carboxylic acid or isocyanate derivatives, which themselves likewise comprise polymerizable double bonds (e.g. (meth)acrylate groups), it is thus possible to link organically polymerizable groups onto free polar functional groups. These reaction products regularly have elevated strength with simultaneously increased hydrophobicity and improved biocompatibility due to the elevated molecular weight.

However, in these cases too, it has been shown that the introduction of additional polymerizable double bonds leads to increased polymerization shrinkage on crosslinking of the polysiloxane compounds, since the double bond density is markedly increased, but the increase in the molecular weight is only comparatively small.

WO 2013/041723 A1 discloses hydrolyzable and polymerizable silanes (including silicic acid polycondensates, i.e. siloxanes) having adjustable spatial distribution of the functional groups, and the use thereof. The teaching disclosed in WO 2013/041723 A1 relates to a method for chain extension of radicals bonded to silicon via carbon in silanes or siloxanes.

WO 2013/053693 A1 discloses silicic acid polycondensates (siloxanes) having cyclic olefin-containing structures and methods for preparation thereof, and the use thereof. WO 2013/053693 A1 discloses that polymer materials having moduli of elasticity adjustable within wide limits combined with high elastic strain (i.e. without brittleness) and hence high fracture toughness can be produced from silicic acid (hetero)polycondensates having cyclic olefin-containing structures.

DE 10 2014 210 432 A1 describes polysiloxane compounds which have the aforementioned disadvantages from the prior art in a curable or cured dental composition at least only in attenuated form, if at all. The conceptual approach to these systems is based on the idea of converting the free functional group in the silane such that no additionally polymerizable double bonds are introduced into the system. Instead, hydrocarbyl radicals of high molecular weight having at least 11 carbon atoms are incorporated into the system. Surprising findings in the case of these curable dental compositions were: i) a good viscosity of the polysiloxane compounds (the viscosity should be 50 Pa*s or less at a temperature of 25° C.) and an associated excellent processibility in the production of a curable dental material containing the polysiloxane compounds, ii) good hydrophobicity, iii) good strength, especially good flexural strength, iv) very low polymerization shrinkage on crosslinking of the polysiloxane compounds, i.e. on curing of the curable dental material, v) good biocompatibility, and vi) a refractive index almost identical to the refractive index of standard dental glasses.

The measures taken in DE 10 2014 210 432 A1 thus solved several problems at once:

Elimination of polar functional groups prevented the formation of intermolecular interactions. It was thus possible to keep the viscosity of the system at a comparatively low level in spite of a remarkable increase in molecular weight.

Incorporation of hydrocarbyl radicals of relatively high molecular weight resulted in widening of intramolecular spacing in the polysiloxane structure, and so it was possible to increase the accessibility of the free-radically polymerizable groups during the curing and hence to optimize the conversion rate. How else could one explain the fact that in these systems, with a comparatively reduced double bond density, the strength of the materials, for example the flexural strength of the cured dental compositions, remains at a very good level and in many cases is actually increased compared to the polysiloxanes without further conversion.

The increase in molecular weight with the same functionality, i.e. in the case of an effective lowering of the double bond density, made it possible to adjust especially what is perhaps the clinically most important technical parameter for a curable dental composition, namely the value of the volume shrinkage during the curing, to an extremely low value. In clinical practice, therapeutic success is also dependent primarily on whether the dental material, for example, seals a cavity prepared by the dentist with high marginal integrity. As a result of shrinkage of the material in the course of polymerization, marginal gaps can form, through which bacteria penetrate into the tooth and then cause the treatment to fail.

Incorporation of hydrocarbyl residues of relatively high molecular weight also made the polysiloxane structure comparatively hydrophobic, such that the undesired water sorption now adopts extremely low values.

The free-radically curable compositions described in DE 10 2014 210 432 A1 are especially suitable for use in a therapeutic method for temporary or permanent filling of a dental cavity. The systems are additionally suitable for use in a therapeutic method as base material, as adhesive (bonding), as a flowable composite material (flow material), as a fissure sealant, as a crown and bridge material, as an inlay/onlay and/or as core buildup material.

DE 10 2014 116 389 A1 discloses combinations of polysiloxanes with disiloxanes, which are particularly suitable for the production of flowable, curable dental materials which are applied by an application cannula or a static mixer. Besides good flow properties in the cannula or mixer and optimal adaptation to the tooth substance, these materials show a sufficiently high packability, so that the good physical properties introduced by the polysiloxanes are fully effective. Furthermore, the combination of polysiloxanes with disiloxanes surprisingly also increased the modulus of elasticity. The cured dental material can thus offer greater resistance to deformation and thus better withstand the constant chewing stresses.

DE 10 2014 116 402 A1 teaches the use of the combinations of polysiloxanes with disiloxanes in generative manufacturing methods, wherein the procedures comprise the stereolithography, the digital light processing, polyjet technology, the galvanometer type scanning method, the microstereolithography, the multi-jet modelling, the selective laser sintering, the 3D printing, the fused deposition modelling, the 3D plotting, the laminated object manufacturing or the film transfer imaging.

The use of polysiloxanes for the production of curable dental composition have made some different development progresses over time, but the mere fact that there are currently only three product families based on polysiloxanes commercially available on the market, shows that the great breakthrough of this interesting and biocompatible substance class has not yet been achieved. The main reason for the currently missing general acceptance of this substance class is the fact that the polymerized polysiloxanes have not yet reached high mechanic values of the flexural strength and the modulus of elasticity at their top, like conventional systems based on traditional dental monomers (bis-GMA, UDMA and TEGDMA) have. Besides the flexural strength, the modulus of elasticity is also a decisive parameter and a key feature for the selection of a restoration material, because a high modulus of elasticity means a high resistance of the material to its elastic deformation, which is especially important when compensating occlusal forces and justifies the high clinical relevance of this parameter.

According to the currently valid ISO standard DIN EN ISO 4049, entitled "Polymer-based restorative materials", the limit of the flexural strength for this material class is 80 MPa if this material is also suitable for restorations of occlusal surfaces. Polysiloxane based restoration materials have such level, but the top values of conventional composite restorative materials are not reached.

In a large scale older investigation of N. Ilie and R. Hickel (Clin. Oral Invest. (2009), 13, 427 438), entitled "Investigations on mechanical behaviour of dental composites", 61 commercially available composite materials were examined and have been tested according to the standard. The following results were obtained: i) Flexural strength=FS in MPa, modulus of elasticity=MOE in GPa, the average values are given, see publication, table 2, bottom of page 433; ii) Hybrid composites: 29 examined materials, FS 116.9, MOE 7.3; iii) Condensable composites: 9 examined materials, FS 105.9, MOE 8.4; iv) Polysiloxane based composites: 2 examined materials, FS 104.3, MOE 7.5; v) Nano-hybrid composites: 7 examined materials, FS 103.1, MOE 5.0; vi) Flowable composites: 10 examined materials, FS 99.8, MOE 4.4; and vii) Microfilled composites: 4 examined materials, FS 73.5, MOE 3.8.

The values prove an acceptable level of mechanical properties of polysiloxane based restorative materials, whereas it should be considered that these early polysiloxane based restorative materials contain, in addition to polysiloxanes, a larger proportion of conventional dental monomers without Si atoms.

In a very recent compilation, taken from the textbook "Werkstoffkunde in der Zahnmedizin, Moderne Materialien and Technologien", edited by M. Rosentritt, N. Illie, U. Lohbauer, 2018, Georg Thieme Verlag, Stuttgart, page 208, table 7.3, "Mechanische Eigenschaften verschiedener Kompositkategorien", the following values can be found: Fiber reinforced composite: FS 132.9, MOE 8.2; Microhybrid: FS 127.8, MOE 6.8; Bulk-fill (flowable): FS 127.6, MOE 5.0; Nanohybrid: FS 125.7, MOE 5.9; Bulk-fill (highly viscous): FS 123.4, MOE 7.1; and Flowable: FS 119.3, MOE 4.2.

This compilation shows that within the last 10 years the mechanical values of the flexural strength of all the restoration materials could be increased by about 20 points each on average and that new composite compositions have been developed (bulk-fill materials).

Unlike the classic light-curable filling composites which are applied in individual, thin layers of about 2 mm to ensure adequate curing of the material and to compensate the volume shrinkage, bulk-fill materials are capable of being photopolymerized in layer thicknesses of up to 5 mm. This performance has been achieved by a higher transparency of the materials. Bulk-fill composites are as shown above divided into two groups: the low viscous, flowable materials and the high viscous, modelable types.

It was the object of the invention to improve significantly the mechanical values of the flexural strength and the modulus of elasticity of the biocompatible polysiloxanes and to bring them into line with the outstanding values of conventional dental composite systems at the top or to exceed the mechanical values of conventional restorative materials. At the same time the clinical relevant values of the volume shrinkage should be reduced. By the polymerization, bonds are formed between the molecules so that the educts are closer together and the resulting solid polymerizates have a denser structure compared to the liquid starting materials. This volume contraction can lead to stresses within the restoration materials and is clinically undesirable. Marginal gap formation and the development of secoundary caries are associated with the phenomenon of shrinkage.

SUMMARY OF THE DISCLOSURE

In one embodiment, the present invention relates to novel polymerizable dental compositions, comprising:

(A) polysiloxanes, wherein the polysiloxanes comprise a mixture of the condensates of the three silanes (a1), (a2) and (a3) and/or a cocondensate of a mixture of the three silanes (a1), (a2) and (a3) and/or a mixture of at least two of the cocondensates (a1)/(a2), (a1)/(a3) and (a2)/(a3) and/or a mixture of the condensate of one of the three silanes (a1), (a2) or (a3) with the cocondensate of the other two silanes, wherein silane (a1) corresponds to the formula $(R^1O)_a R^2{}_b Si[-A(-Y\{-B[-PG]_f\}_e)_d]_c$, wherein Y=—C(=O)NH—, —NHC(=O)—, —OC(=O)NH—, —NHC(=O)O—, —SC(=O)NH—, —NHC(=O)S—, —NHC(=O)NH—, —OC(=O)N(—C(=O)NH—)—, —SC(=O)N(—C(=O)NH—)—, —NHC(=O)N(—C(=O)NH—)—, —C(=O)NHC(=O)NH—, or —NHC(=O)NHC(=O)—, wherein the bond arranged on the left in each formula is closer to the structural element A and the bond arranged on the right is closer to the structural element B, PG=polymerizable group, A=an organic linking group, connecting Si with Y and comprising 1 to 20 C-atoms, B=an organic linking group, connecting Y with PG and comprising 1 to 20 C-atoms, $R^1$=H or C1- to C4-alkyl,
$R^2$=C1- to C4-alkyl,
a=2 or 3,
b=0 or 1,
c=1 or 2,
d=1 to 3,
e=1 or 2,
f=1 to 5,
a+b+c=4, and wherein silane (a2) corresponds to the formula $(R^1O)_a R^2{}_b Si[-A'(PG)_f]_c$, wherein PG=polymerizable group, A'=an organic linking group, connecting Si with PG and comprising 1 to 20 C-atoms and none of the groups —C(=O)NH—, —NHC(=O)—, —OC(=O)NH—, —NHC(=O)O—, —SC(=O)NH—, —NHC(=O)S—, —NHC(=O)NH—, —OC(=O)N(—C(=O)NH—)—, —SC(=O)N(—C(=O)NH—)—, —NHC(=O)N(—C(=O)NH—)—, —C(=O)NHC(=O)NH—, or —NHC(=O)NHC(=O)—, $R^1$=H or C1- to C4-alkyl,
$R^2$=C1- to C4-alkyl,
a=2 or 3
b=0 or 1
c=1 or 2
f=1 to 5,
a+b+c=4, and wherein the silane (a3) corresponds to the formula $(R^1O)_a R^2{}_b SiAr_c$, wherein $R^1$=H or C1- to C4-alkyl,
$R^2$=C1- to C4-alkyl,
Ar=aryl, wherein different Ar groups may be the same or different,
a=2 or 3,
b=0 or 1,
c=1 or 2
a+b+c=4, (B) fillers, and
(C) initiators and/or catalysts and/or activators for the polymerization.

The cured dental products formed from the polymerizable dental compositions according to the invention, are useful as dental material, in particular as flowable or condensable, permanent or temporary filling composite, as so called "bulk fill" material, as core buildup material, as dental luting cement, as dental sealing material, as dental lacquer, as dental base material, as crown and bridge material, as dental adhesive (bonding), as dental primer, as soft or hard relining material, as inlay, onlay and/or overlay, as artificial tooth, as orthodontic material, as denture, as dental framework, as dental temporary prosthesis, as dental block material, as partial or full prosthesis. Furthermore, they are suitable for use in generative dental manufacturing method, also known as "rapid prototyping", preferably for stereolithography, preferred for digital light processing (DLP), selective laser assembling (SLA), microstereolithography, 3D-printing, laminated object manufacturing or film transfer imaging.

The invention further relates to a process for producing the dental compositions and to a method for producing a respective dental product. Additionally claimed are inventive kits containing the novel polymerizable dental compositions.

The present invention also relates to polymerizable dental compositions, comprising components (A), (B) and (C) as defined above and one or more than one compound which is/are not polysiloxane(s) according to the invention. Optionally inventive polymerizable dental compositions may also contain (D) organic, polymerizable monomers which are not polysiloxanes according to the invention (i.e., which are other than Component (A)), preferably for reaction with the inventive polysiloxanes. (i.e., Component (A)).

The present invention also relates to polymerizable dental compositions, comprising components (A), (B), (C) and optionally (D) as defined above and one or more than one compound which is/are not polysiloxane(s) according to the invention (i.e., which are other than Component (A)), but polymerizable compounds without Si-atom which contain acid groups. Optionally inventive polymerizable dental compositions thus may also contain:

(E) Organic Monomers without Si-Atoms Bearing Acid Groups.

Inventive embodiments also include polymerizable dental materials as defined above, comprising at least one (e.g., comprising one, two or more than two or all substances) of the group of the additives (F) consisting of:
rheological auxiliaries,
colorants, preferably color pigments,
aromas,
stabilizers, in particular daylight stabilizers,
inhibitors,
molecular weight regulators,
preservatives, preferably parabens,
interface-active substances, preferably surfactants,
microbicides, preferably bactericides,
organic polymers and oligomers and compounds having high molecular weights,
thickeners,
dental medicines and
plasticizers.

Inventive embodiments also include polymerizable dental materials as defined above, comprising at least one solvent (G) (i.e., comprising one, two or more than two solvents (G)).

Most preferably the present invention relates to polymerizable dental compositions and polymerized dental compositions, as defined above for specific use in a therapeutic method (a method for the therapeutic treatment of the human or animal body, preferably of the human body).

In one embodiment, the present disclosure is directed to polymerizable dental compositions containing (A) polysiloxanes, wherein the polysiloxanes comprise at least a mixture of the condensates of the three silanes (a1), (a2) and (a3) and/or at least a cocondensate of a mixture of the three silanes (a1), (a2) and (a3) and/or at least a mixture of at least two of the cocondensates (a1)/(a2), (a1)/(a3) and (a2)/(a3) and/or at least a mixture of the condensate of one of the three silanes (a1), (a2) or (a3) with the cocondensate of the other both silanes.

In one embodiment, the present disclosoure is directed to polymerizable dental compositions containing (A) polysiloxanes, wherein the polysiloxanes comprise any mixture of condensates and cocondensates comprising (a1), (a2) and (a3), for example the mixture of two or three different cocondensates (a1)/(a2)/(a3) or a mixture of a cocondensate (a1)/(a2)/(a3) with the condensate (a1), etc.

For example, in one embodiment, the disclosure is directed to a polymerizable dental composition comprising homo- and/or cocondensates of at least one of each of the three silanes (a1), (a2) and (a3).

Further aspects of the present invention and preferred configurations thereof will become apparent from the description, which follows, the working examples and the claims.

DETAILED DESCRIPTION OF THE DISCLOSURE

The term "comprise" is used in the context of this application in its usual and generally accepted meaning.

The term "(meth)acryl" is understood in the context of the present text to mean both "acryl" and "methacryl".

In the context of this text, the term "polymerizable groups" is understood to mean functional groups which, as a constituent of molecules, give rise to solid polymerizates by curing, i.e. which are capable to convert from a liquid-pasty phase into a solid phase. Here monomers react to form polymers. The reactions comprise both chain-growth reactions and step-growth reactions, including free radical chain polymerization, coordinative chain polymerization, cationic chain polymerization and anionic chain polymerization and also polyaddition.

Polysiloxane compounds have long been known and are obtainable, for example, by hydrolysis and condensation of silanes having hydrolyzable groups (see, for example, DE 27 58 414 A1) or by hydrosilylation of allyl or vinyl compounds with SiH-containing compounds. Polysiloxane compounds can be processed further to give a multitude of products, for example overlayers, coatings, membranes or bulk materials. This further processing is frequently based on a crosslinking reaction of organically polymerizable groups in the polysiloxane compounds (e.g. (meth)acrylate groups) and the resulting formation of crosslinked polysiloxane compounds.

Preferably the groups polymerize (cure or crosslink) in a chain-growth reaction, either free-radically or cationic. Preferably, the groups polymerize free-radically.

Chain-like and/or cyclic and/or cage-type polysiloxanes substituted by polymerizable groups are generally synthesized via the sol-gel process by controlled hydrolysis and condensation of appropriately functionalized derivatives of alkoxides of silicon or of halosilanes. These production methods have been described many times in the literature. In general, such a synthesis proceeds from a standard silane, for example isocyanatopropyldiethoxymethylsilane, which is reacted in a first step in a standard reaction, for example in an isocyanate-alcohol addition, for example with glycerol 1,3-dimethacrylate, to give the corresponding urethane. The resulting compound consists on the one hand of the silicon atom which is furnished with hydrolyzable and condensable groups and is linked via a spacer consisting of an alkyl group (here a propyl group) and a urethane group as a structural connecting element to a further functional structural segment, in this case to two free-radically polymerizable (meth) acrylate groups. Such a simple synthesis method can be modified in various ways, since the possible reactions between appropriately functionalized silanes and suitable reactants seem unlimited. There is a correspondingly large number of synthesis suggestions in the literature. The starting compound thus comprises an inorganically condensable structural element, a variable connecting element and a polymerizable organic base structure. In a catalytically controlled hydrolysis and condensation, the polysiloxane is obtained as an inorganic condensate substituted, for example by free-radically or cationic polymerizable groups. Whether the polycondensate is in the form of chains, rings or three-dimensional cage forms, or in the corresponding mixed forms, depends on the exact conditions of the condensation. These include not only the reaction conditions (pH, amount of solvent and water, type and amount of catalyst, reaction temperature, manner of processing, etc.) but also the structural forms of the starting silane, important factors being the number of alkoxy groups, the number of polymerizable groups, the chemical nature of the connecting element and the chain length of the spacer. Details of this can be found both in the scientific literature and in the patent literature.

Below, possible structure types are specified by way of example, wherein the polymerizable groups have free-radically curable (meth)acrylate groups.

Specifically, cyclic, chain-like and cage-type structures and a possible mixed form of cyclic and chain-like condensates are illustrated below. Depending on the reaction conditions and the structural elements of the educts, the synthesis of both pure form condensates and mixed form condensates is possible.

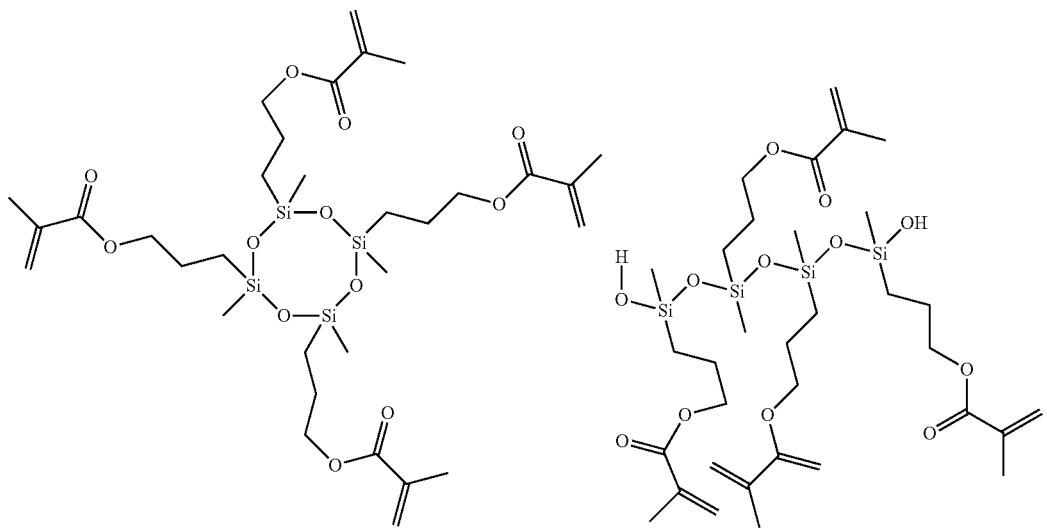

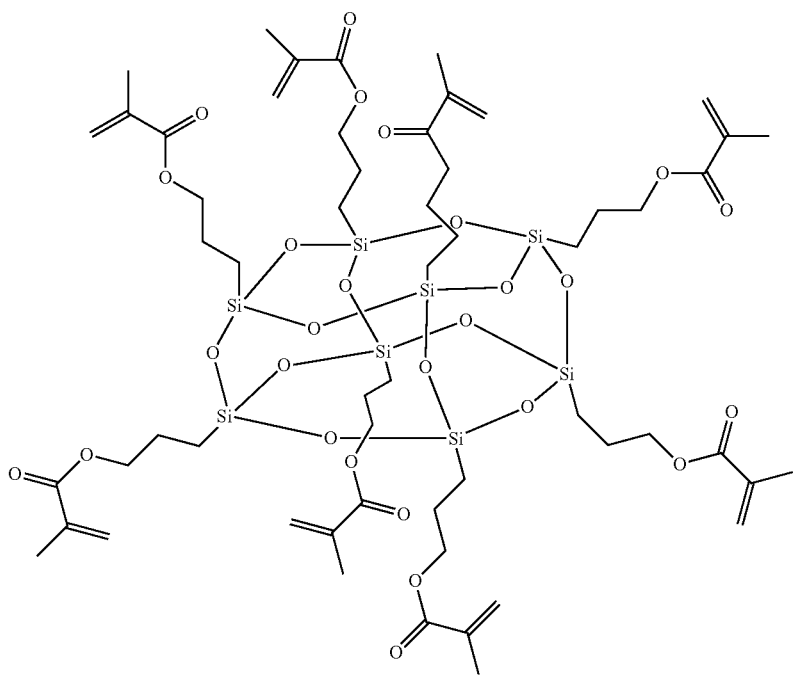

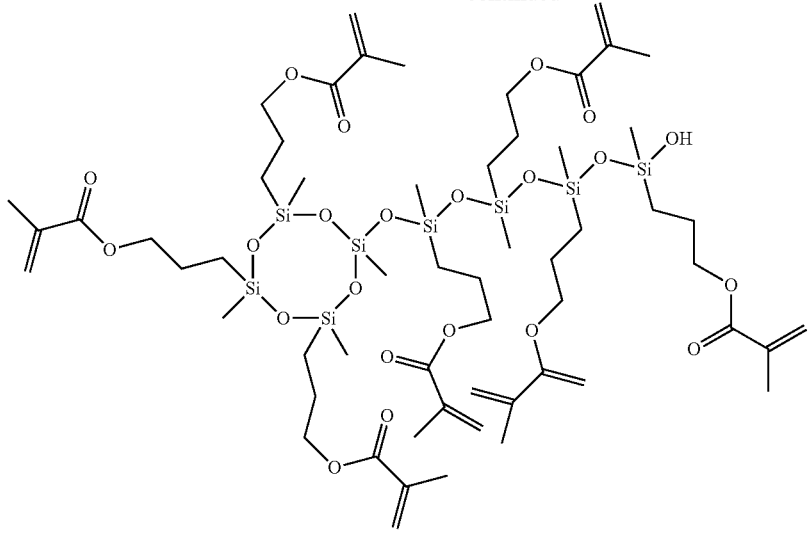

The polysiloxanes, being a link between inorganic and organic chemistry, have exceptional material properties. Since they are additionally physiologically inert, i.e. have no significant toxicity, they are especially important for applications in medicine. The reason why polysiloxanes are virtually nontoxic is the low biological attackability of the silicon-carbon bonds and the restricted ability of the highly hydrophobic polymer chains to diffuse through cell membranes, which is why they should be particularly suitable for implantation (in teeth).

Surprisingly it has now been found that polysiloxane based dental composite materials for restoration with extremely good mechanical properties are available even without having to fall back to conventional dental monomers if the polymerizable matrix comprises polysiloxanes, wherein the polysiloxanes (A) comprise a mixture of the condensates of the three silanes (a1), (a2) and (a3) and/or a cocondensate from a mixture of the three silanes (a1), (a2) and (a3) or a mixture of at least two of the condensates (a1)/(a2), (a1)/(a3) and (a2)/(a3) and/or a mixture of the condensate of one of the three silanes (a1), (a2) and (a3) with the cocondensate of the other two silanes.

In a preferred embodiment, the amount of the silanes (a1), (a2) and (a3) in the cocondensate or in the mixture of the condensates or cocondensates is:

(a1) in the amount of 10 to 70% by weight, preferably 20 to 60% by weight, (a2) in the amount of 10 to 70% by weight, preferably 20 to 50% by weight, and (a3) in the amount of 5 to 60% by weight, preferably 10 to 40% by weight, respectively based on the total amount of the silanes (a1), (a2) and (a3).

Such mixtures are new and are not suggested by the state of the art.

Component (A)—Different Silanes (a1), (a2) and (a3)

The structures of the silanes (a1), (a2) and (a3) are set forth below, as well as the procedures for their synthesis. The CAS numbers mentioned in this context are to be understood as examples. The same substances can have different CAS numbers. This may, for example, be the case if there are different isomers (constitutional isomers, stereo isomers, conformational isomers, configurational isomers, enantiomers, diastereomers) or if the substance is characterized as a reaction product of its starting substances. These variants are also suitable and can be used.

Silane $(R^1O)_a R^2_b Si[-A(-Y\{-B[-PG]_f\}_e)_d]_c$ (a1):

Silane (a1) has the formula $(R^1O)_a R^2_b Si[-A(-Y\{-B[-PG]_f\}_e)_d]$, wherein:

Y=—C(=O)NH—, —NHC(=O)—, —OC(=O)NH—, —NHC(=O)O—, —SC(=O)NH—, —NHC(=O)S—, —NHC(=O)NH—, —OC(=O)N(—C(=O)NH—)—, —SC(=O)N(—C(=O)NH—)—, —NHC(=O)N(—C(=O)NH—)—, —C(=O)NHC(=O)NH—, or —NHC(=O)NHC(=O)—, wherein the bond arranged on the left in each formula is closer to the structural element A and the bond arranged on the right is closer to the structural element B, PG=polymerizable group, A=an organic linking group, connecting Si with Y and comprising 1 to 20 C-atoms, B=an organic linking group, connecting Y with PG and comprising 1 to 20 C-atoms, $R^1$=H or C1- to C4-alkyl, $R^2$=C1- to C4-alkyl, a=2 or 3, b=0 or 1, c=1 or 2, d=1 to 3, e=1 or 2, f=1 to 5 and a+b+c=4.

In a preferred embodiment, Y is selected from the group consisting of —$(X)_x$—, C(=O)NH—, —NHC(=O)—$(X)_x$— and —$(X)_x$C(=O)N(—C(=O)NH—)—, wherein X is selected from the group consisting of O, S and NH, and preferably X is selected from the group consisting of O and S, and wherein the index x is either 0 or 1, and preferably is 1.

In one embodiment, Y is selected from the group consisting of —$(X)_x$—, C(=O)NH—, —NHC(=O)—$(X)_x$—, —$(X)_x$C(=O)N(—C(=O)NH—)—, —C(=O)NHC(=O)NH—, and —NHC(=O)NHC(=O)—, wherein X is selected from the group consisting of O, S, and NH, x is either 0 or 1, and wherein the bond arranged on the left in each formula is closer to the structural element A and the bond arranged on the right is closer to the structural element B.

In a preferred embodiment the polymerizable group PG is selected from the group consisting of —CH=CH$_2$, —C(CH$_3$)=CH$_2$, —C(=O)—CH=CH$_2$, —C(=O)—C(CH$_3$)=CH$_2$, —Z—C(=O)—CH=CH$_2$ and —Z—C(=O)—C(CH$_3$)=CH$_2$, wherein Z is selected from the group consisting of O and NH. In a especially preferred embodiment the polymerizable group PG is selected from the group consisting of —Z—C(=O)—CH=CH$_2$ and —Z—C(=O)—C(CH$_3$)=CH$_2$, wherein Z is selected from the group consisting of O and NH. In a particularly preferred embodiment the polymerizable group PG is selected from the group consisting of —Z—C(=O)—CH=CH$_2$ and —Z—C(=O)—C(CH$_3$)=CH$_2$, wherein Z=O.

In another preferred embodiment, the group PG is selected from the group consisting of structural elements comprising an oxirane unit, preferably an epoxycyclohexane unit or a norbornene epoxide unit. In one embodiment, PG is selected from:

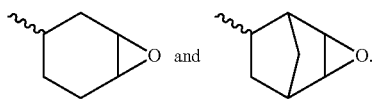

In one embodiment, the organic linking group A, connecting the Si-atom to the group Y is a (d+1) valent, straight-chain, branched or cyclic group, comprising 1 to 20 C-atoms, and optionally may contain O atoms, S atoms, NR groups, ester groups or thioester groups.

In a preferred embodiment, the linking group A is selected from the group consisting of —(CH$_2$)$_n$— wherein n=1 to 12, —(CH$_2$)$_n$—N(CH$_3$)—(CH$_2$)$_n$— wherein n=1 to 4, —(CH$_2$)$_n$N[(CH$_2$)$_n$—]$_2$ wherein n=1 to 4, and —(CH$_2$)$_n$—CH(R)—(CH$_2$)$_n$— wherein n=0 to 4 and R=methyl, ethyl, or phenyl, wherein the bond arranged on the left is connected to the Si atom and the bond arranged on the right is connected to the Y group.

In a particularly preferred embodiment the linking group A is —(CH$_2$)$_n$— wherein n=1 to 6.

In one embodiment, the organic linking group B, connecting the group Y to the polymerizable group PG is a (f+1)-valent, straight-chain, branched or cyclic group, comprising 1 to 20 C-atoms, and optionally may contain O atoms, S atoms, NR groups, ester groups or thioester groups.

In a preferred embodiment, the linking group B is selected from the group consisting of —(CH$_2$)$_n$— wherein n=1 to 12, —CH$_2$CH(CH$_3$)—, —CH(CH$_3$)CH$_2$—, —(CH$_2$)$_2$(OCH$_2$CH$_2$)$_n$— wherein n=1 to 6, —(CH$_2$)$_n$OC(=O)(CH$_2$)$_m$— wherein n and m independently=1 to 6, —(CH$_2$)C(=O)O(CH$_2$)$_m$ wherein n and m independently=1 to 6, —CH(CH$_2$OPh)CH$_2$—,

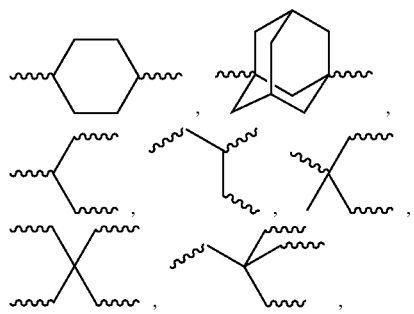

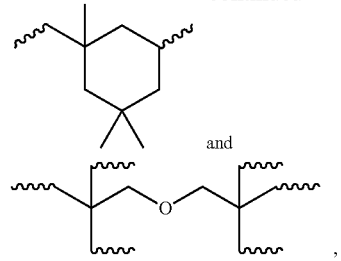

and wherein the bond arranged on the left is connected to the group Y and the bond(s) arranged on the right is/are connected to the group PG.

In a particularly preferred embodiment, the linking group B is —(CH$_2$)$_n$— wherein n=1 to 6.

In a preferred embodiment, the radical R$^1$ is selected from the group consisting of H, methyl and ethyl.

In a preferred embodiment, the index d=1 to 2.

In a preferred embodiment, the index f=1 to 2.

Preferred silanes (a1) include those where e is 1; PG is —Z—C(=O)C(=CH$_2$)R$^3$, where Z is O or NH and R$^3$ is H or methyl; and Y is selected from the group consisting of —C(=O)NH—, —NH—C(=O)—, —X—C(=O)—NH—, and —NH—C(=O)—X—, where X is O, S, or NH. Such preferred silanes include those having the following formulas:

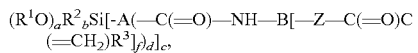

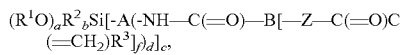

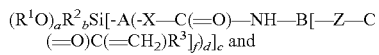

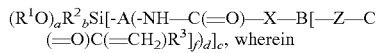
wherein

A=an organic linking group, connecting Si with Y, wherein A is selected from the group comprising —(CH$_2$)$_n$— wherein n=1 to 12, —(CH$_2$)$_n$—N(CH$_3$)—(CH$_2$)$_n$— wherein n=1 to 4, —(CH$_2$)$_n$N[(CH$_2$)$_n$—]$_2$ wherein n=1 to 4 and —(CH$_2$)$_n$—CH(R)—(CH$_2$)$_n$— wherein n=0 to 4 and R=methyl, ethyl, or phenyl, and preferably A is —(CH$_2$)$_n$— wherein n=1 to 6;

B=an organic linking group, connecting Y with Z, wherein B is selected from the group comprising —(CH$_2$)$_n$— wherein n=1 to 12, —CH$_2$CH(CH$_3$)—, —CH(CH$_3$)CH$_2$—, —(CH$_2$)$_2$(OCH$_2$CH$_2$)$_n$— wherein n=1 to 6, —(CH$_2$)$_n$OC(=O)(CH$_2$)$_m$— wherein n and m independently=1 to 6, —(CH$_2$)C(=O)O(CH$_2$)$_m$ wherein n and m independently=1 to 6, —CH(CH$_2$OPh)CH$_2$—,

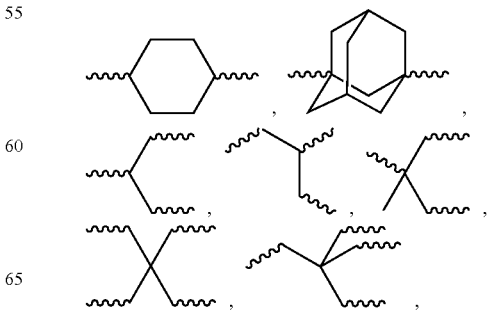

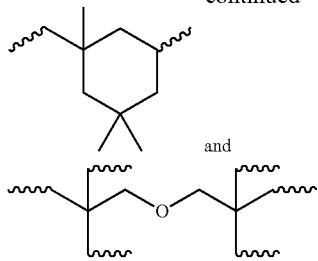

and preferably B is —$(CH_2)_n$— wherein n=1 to 6,
X=O, S, NH; preferably O;
Z=O, NH; preferably O;
$R^1$=H or C1- to C4-alkyl, preferably H, methyl or ethyl;
$R^2$=C1- to C4-alkyl,
$R^3$=H, methyl; preferably methyl;
a=2 or 3,
b=0 or 1,
c=1 or 2,
d=1 to 3, preferably 1 to 2,
f=1 to 5, preferably 1 to 2, and
a+b+c=4.

Synthesis of Silanes with Urethane, Thiourethane, Urea or Amide Groups Proceeding from Isocyanates Silanes with urethane, thiourethane or urea groups can be easily prepared by Sn or Bi catalyzed reaction of the corresponding silanes comprising OH, SH or $NH_2$ groups with (meth)acryloyl-substituted isocyanates.

Alternatively a Sn or Bi catalyzed reaction of isocyanate-substituted silanes with the corresponding OH, SH or $NH_2$-substituted (meth)acrylate compounds is also possible.

By reacting isocyanate-substituted silanes with carboxyl-substituted (meth)acrylate compounds, the corresponding amides can be produced by splitting off $CO_2$.

Synthesis of $(R^1O)_aR^2{}_bSi[-A(-X—C(=O)—NH—B[—Z—C(=O)C(=CH_2)R^3]_f]_d]_c$

The synthesis of the silanes $(R^1O)_aR^2{}_bSi[-A(-X—C(=O)—NH—B[—Z—C(=O)C(=CH_2)R^3]_f]_d]_c$ is effected by tin or bismuth catalysis from a silane with XH group and a (meth)acrylate compound with an isocyanate group. Preferred catalysts are dibutyltin dilaurate and bismuth neodecanoate. Under slight heating one XH group reacts with an isocyanate group in an equimolar ratio. The reaction usually runs completely and can easily be monitored in the IR spectrum until the isocyanate band (2270 cm$^{-1}$) has completely disappeared.

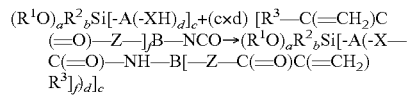

Several commercially available starting compounds are shown in the following Tables 1 and 2.

TABLE 1

| | $(R^1O)_aR^2{}_bSi[—A(—XH)_d]_c$ | | | | | | |
|---|---|---|---|---|---|---|---|
| CAS-Nr. | $R^1$ | $R^2$ | XH | a | b | c | d | -A- |
| 53764-54-8 | Me | — | OH | 3 | 0 | 1 | 1 | —$(CH_2)_3$— |
| 53394-61-9 | Et | — | OH | 3 | 0 | 1 | 1 | —$(CH_2)_3$— |
| 99697-20-8 | Me | Me | OH | 2 | 1 | 1 | 1 | —$(CH_2)_3$— |
| 162781-70-6 | Et | — | OH | 3 | 0 | 1 | 1 | —$CH_2$— |
| 4420-74-0 | Me | — | SH | 3 | 0 | 1 | 1 | —$(CH_2)_3$— |
| 14814-09-6 | Et | — | SH | 3 | 0 | 1 | 1 | —$(CH_2)_3$— |
| 31001-77-1 | Me | Me | SH | 2 | 1 | 1 | 1 | —$(CH_2)_3$— |

TABLE 1-continued

| | $(R^1O)_aR^2{}_bSi[—A(—XH)_d]_c$ | | | | | | |
|---|---|---|---|---|---|---|---|
| CAS-Nr. | $R^1$ | $R^2$ | XH | a | b | c | d | -A- |
| 30817-94-8 | Me | — | SH | 3 | 0 | 1 | 1 | —$CH_2$— |
| 60764-83-2 | Et | — | SH | 3 | 0 | 1 | 1 | —$CH_2$— |
| 877593-17-4 | Me | — | SH | 3 | 0 | 1 | 1 | —$(CH_2)_{11}$— |
| 57765-40-9 | Me | — | SH | 2 | 0 | 2 | 1 | —$(CH_2)_3$— |
| 13822-56-5 | Me | — | $NH_2$ | 3 | 0 | 1 | 1 | —$(CH_2)_3$— |
| 3663-44-3 | Me | Me | $NH_2$ | 2 | 1 | 1 | 1 | —$(CH_2)_3$— |
| 3179-76-8 | Et | Me | $NH_2$ | 2 | 1 | 1 | 1 | —$(CH_2)_3$— |
| 71408-48-5 | Me | — | $NH_2$ | 3 | 0 | 1 | 1 | —$CH_2$— |
| 18306-83-7 | Et | — | $NH_2$ | 3 | 0 | 1 | 1 | —$CH_2$— |
| 51749-36-1 | Me | — | $NH_2$ | 2 | 0 | 2 | 1 | —$(CH_2)_3$— |
| 53746-12-6 | Et | — | $NH_2$ | 2 | 0 | 2 | 1 | —$(CH_2)_3$— |
| 330457-46-0 | Me | — | OH | 3 | 0 | 1 | 1 | —$(CH_2)_3$—N($CH_3$)—$(CH_2)_2$— |
| 24801-87-4 | Me | — | OH | 3 | 0 | 1 | 2 | —$(CH_2)_3$N[$(CH_2)_2$—]$_2$ |
| 7538-44-5 | Et | — | OH | 3 | 0 | 1 | 2 | —$(CH_2)_3$N[$(CH_2)_2$—]$_2$ |

TABLE 2

| | [$R^3$—C(=$CH_2$)C(=O)—Z—]$_f$B—NCO | | | |
|---|---|---|---|---|
| CAS-Nr. | $R^3$ | Z | f | —B— |
| 30674-80-7 | Me | O | 1 | —$(CH_2)_2$— |
| 130025-29-5 | Me | O | 1 | —$CH_2CH(CH_3)$— |
| 86241-25-0 | Me | O | 1 | —$(CH_2)_3$— |
| 93956-19-5 | Me | O | 1 | —$CH_2$— |
| 13641-96-8 | H | O | 1 | —$(CH_2)_2$— |
| 223909-47-5 | H | O | 1 | —$CH_2CH(CH_3)$— |
| 119096-71-8 | H | O | 1 | —$(CH_2)_3$— |
| 886577-76-0 | H | O | 2 | |
| 953028-96-1 | H | NH | 1 | —$(CH_2)_3$— |
| 61994-33-0 | H | NH | 1 | |

Some syntheses of the silanes $(R^1O)_aR^2{}_bSi[-A(-X—C(=O)—NH—B[—Z—C(=O)C(=CH_2)R^3]_f]_d]_c$ are shown by way of example hereinafter.

Silane (1) is synthesized by the reaction of 3-(trimethoxysilyl)-1-propanol with 2-isocyanatoethyl methacrylate.

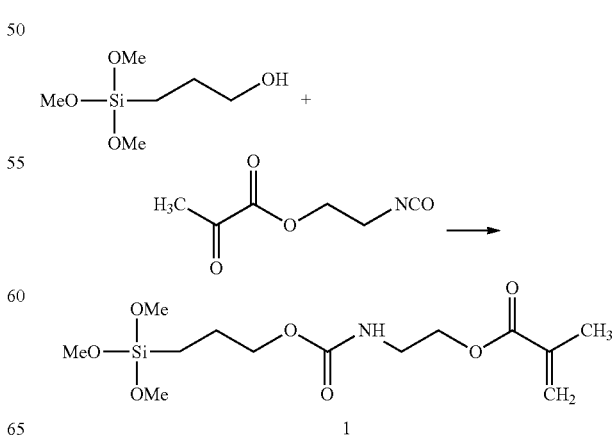

1

Silane (2) is synthesized by the reaction of 3-(methyldimethoxysilyl)-1-propanol with 2-isocyanatoethyl methacrylate.

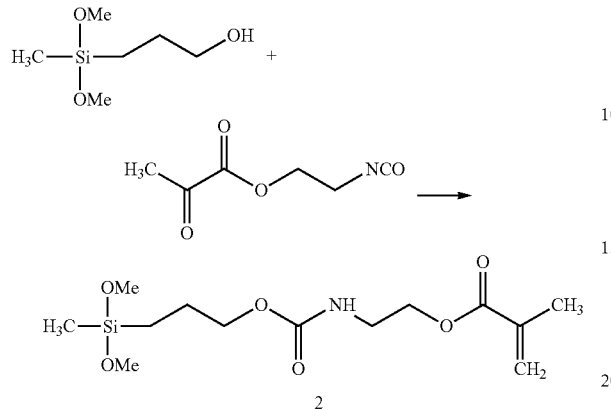

2

Silane (3) is synthesized by the reaction of 1-(triethoxysilyl)methanol with 2-isocyanatoethyl methacrylate.

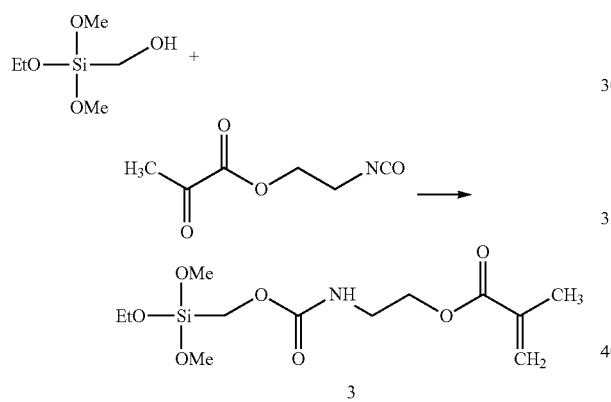

3

Silane (4) is synthesized by the reaction of 3-(trimethoxysilyl)-1-propanol with 3-isocyanatopropyl methacrylate.

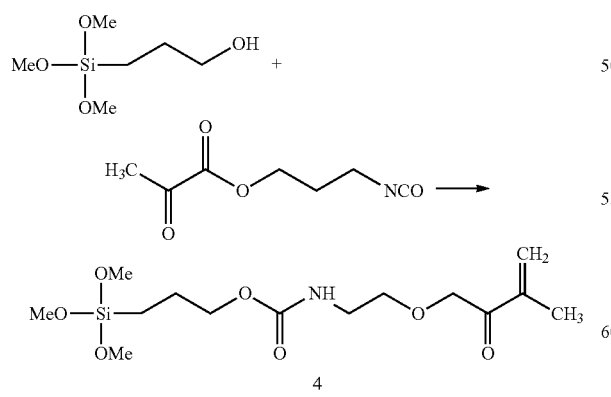

4

Silane (5) is synthesized by the reaction of 3-(trimethoxysilyl)-1-propanol with 1,1-bis(acryloyloxymethyl)ethyl isocyanate.

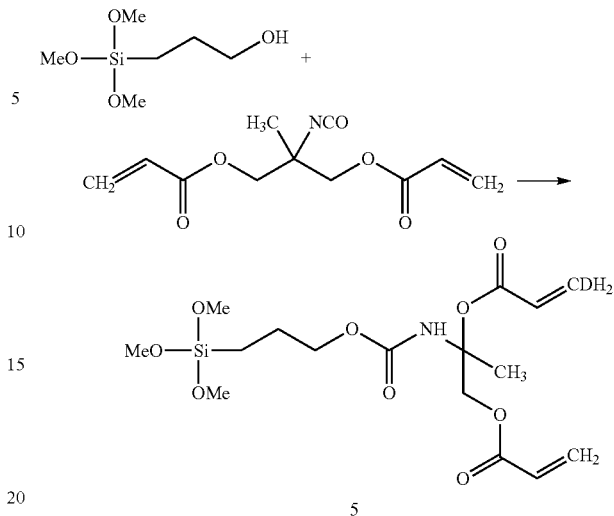

5

Silane (6) is synthesized by the reaction of 1-(trimethoxysilyl)methanethiol with 2-isocyanatoethyl methacrylate.

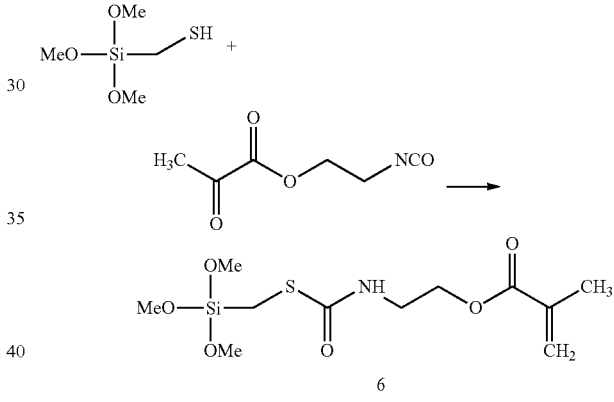

6

Silane (7) is synthesized by the reaction of 3-(trimethoxysilyl)-1-propanethiol with 2-isocyanatoethyl methacrylate.

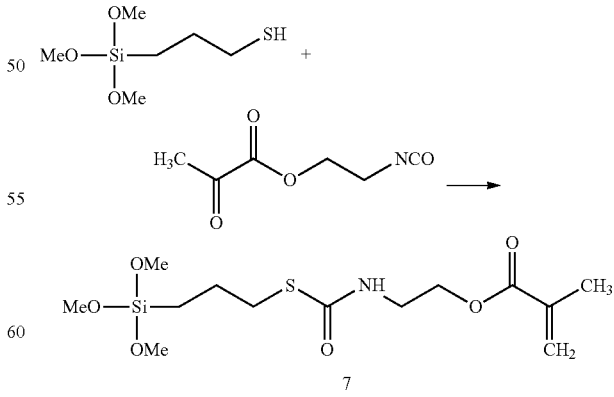

7

Silane (8) is synthesized by the reaction of 11-(trimethoxysilyl)-1-undecanethiol with 2-isocyanatoethyl methacrylate.

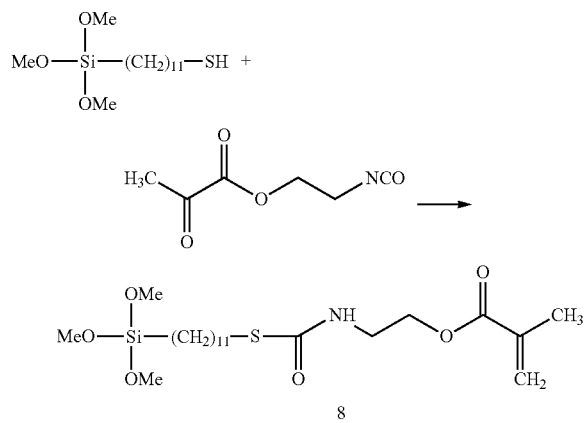

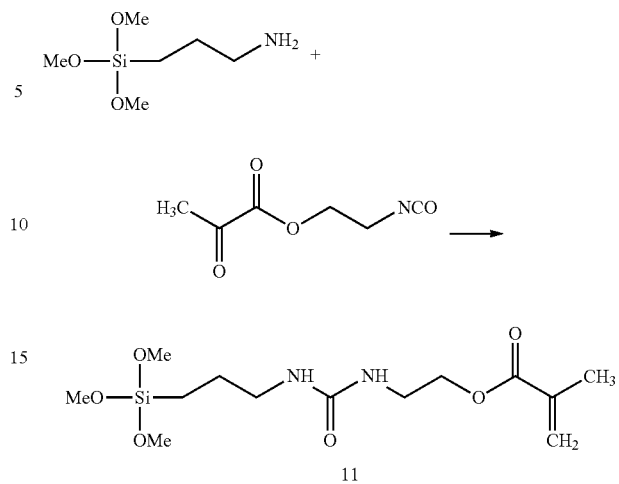

Silane (9) is synthesized by the reaction of 3-(methyldimethoxysilyl)-1-propanethiol with 2-isocyanatoethyl methacrylate.

Silane (12) is synthesized by the reaction of 3-(methyldimethoxysilyl)-1-propanamine with 2-isocyanatoethyl methacrylate.

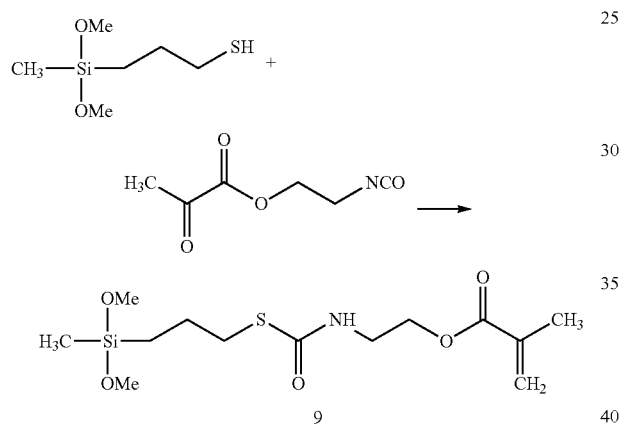

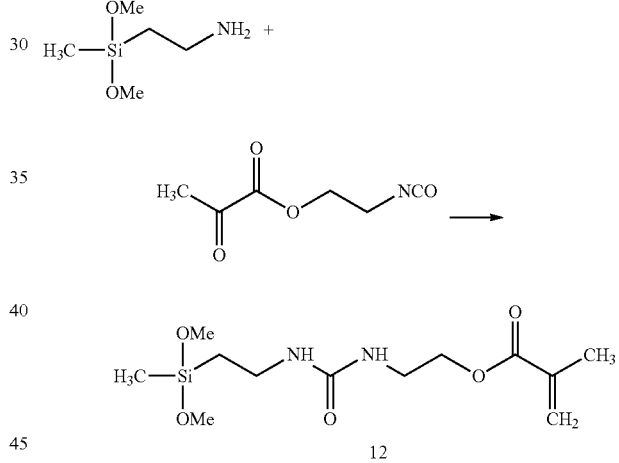

Silane (10) is synthesized by the reaction of 1-(trimethoxysilyl)methanamine with 2-isocyanatoethyl methacrylate.

Silane (13) is synthesized by the reaction of 3,3-(diethoxysilylene)bis[1-propanamine] with 2 equivalents of 2-isocyanatoethyl methacrylate.

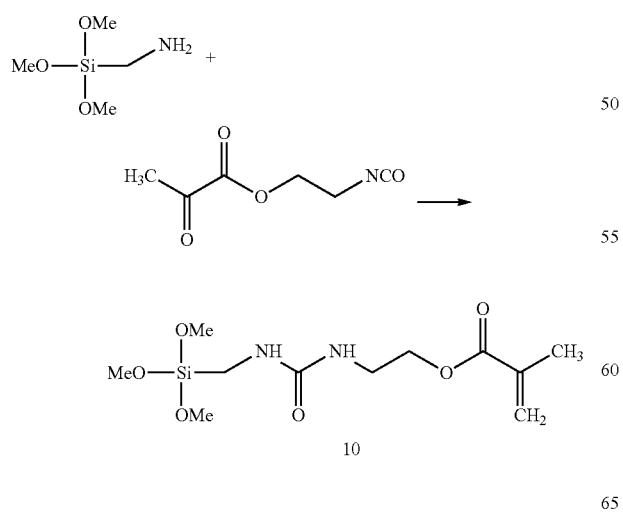

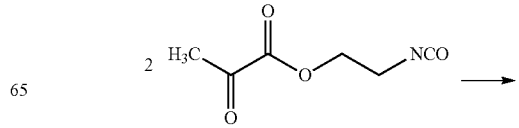

Silane (11) is synthesized by the reaction of 3-(trimethoxysilyl)-1-propanamine with 2-isocyanatoethyl methacrylate.

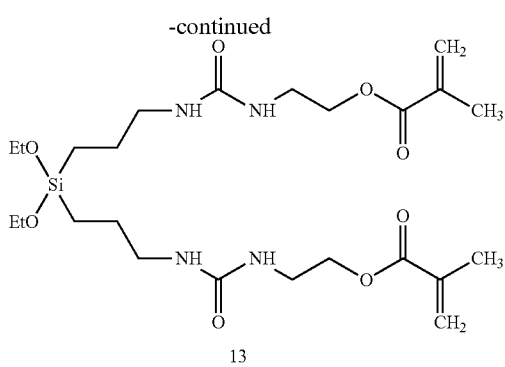

13

Silane (14) is synthesized by the reaction of 2-[methyl[3-(trimethoxysilyl)propyl]amino]ethanol with 2-isocyanatoethyl methacrylate.

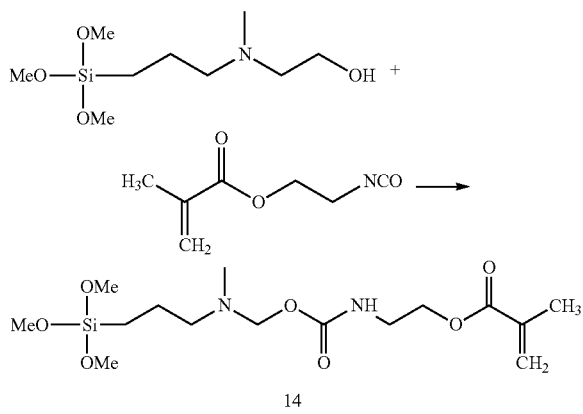

14

Silane (15) is synthesized by the reaction of 2,2'-[[3-(triethoxysilyl)propyl]imino]bis[ethanol] with 2 equivalents of 2-Isocyanatoethyl methacrylate.

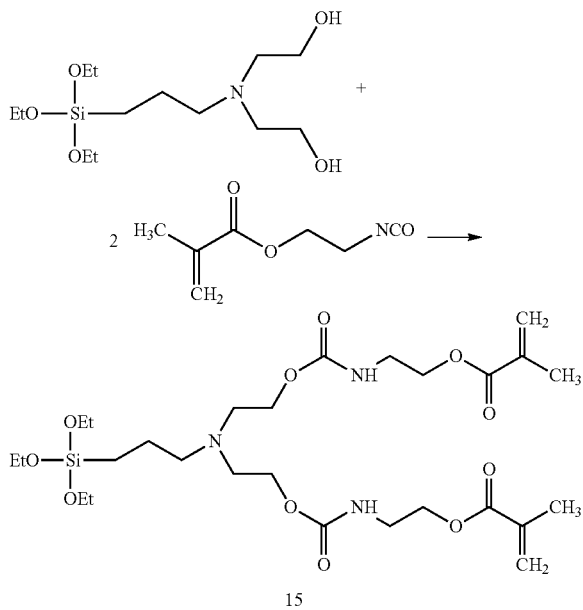

15

Synthesis of $(R^1O)_a R^2{}_b Si[-A(-X-C(=O)-N(-B[-Z-C(=O)C(=CH_2)R^3]_f)-C(=O)-NH-B[-Z-C(=O)C(=CH_2)R^3]_f)]_d]_c$ The synthesis of the silanes $(R^1O)_a R^2{}_b Si[-A(-X-C(=O)-N(-B[-Z-C(=O)C(=CH_2)R^3]_f)-C(=O)-NH-B[-Z-C(=O)C(=CH_2)R^3]_f)]_d]_c$ is carried out analogously to the synthesis described above of the silanes $(R^1O)_a R^2{}_b Si[-A(-X-C(=O)-NH-B[-Z-C(=O)C(=CH_2)R^3]_f)]_d]_c$. In this case one equivalent of XH group reacts with two equivalents of isocyanate to obtain the corresponding allophanates, thioallophanates and biurets. The reactions also proceed by tin or bismuth catalysis. Preferred catalysts are also dibutyltin dilaurate and bismuth neodecanoate. Under slight heating one XH group reacts with two equivalents of isocyanate compounds. The reaction usually runs completely and can easily be monitored in the IR spectrum until the isocyanate band (2270 cm$^{-1}$) has completely disappeared.

It is also possible to react the XH groups with the isocyanate groups in a stoichiometry between 1:1 and 1:2. Then the second reaction stage can not be carried out completely, so that a mixture of urethane and allophanate or of thiourethane and thioallophanate or of urea and biuret is obtained. Polymerizable dental compositions according to the invention can thus also contain corresponding mixed forms (a1).

$(R^1O)_a R^2{}_b Si[-A(-XH)_d]_c + (2 \times c \times d)[R^3-C(=CH_2)C(=O)-Z-]_f B-NCO \rightarrow (R^1O)_a R^2{}_b Si[-A(-X-C(=O)-N(-B[-Z-C(=O)C(=CH_2)R^3]_f)-C(=O)-NH-B[-Z-C(=O)C(=CH_2)R^3]_f)]_d]_c$ The commercially available compounds shown in Tables 1 and 2 can also be used as starting compounds.

Some syntheses of the silanes $(R^1O)_a R^2{}_b Si[-A(-X-C(=O)-N(-B[-Z-C(=O)C(=CH_2)R^3]_f)-C(=O)-NH-B[-Z-C(=O)C(=CH_2)R^3]_f)]_d]_c$ are shown by way of example hereinafter.

Allophanate silane (16) is synthesized by the reaction of 3-(trimethoxysilyl)-1-propanol with 2 equivalents of 2-Isocyanatoethyl methacrylate.

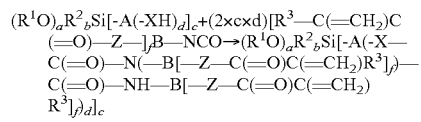

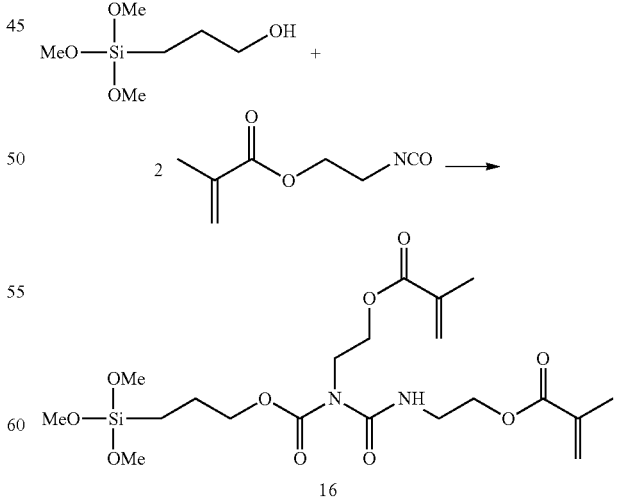

16

Allophanate silane (17) is synthesized by the reaction of 3-(methyldimethoxysilyl)-1-propanol with 2 equivalents of 2-Isocyanatoethyl methacrylate.

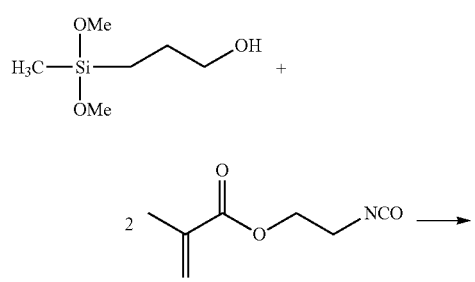

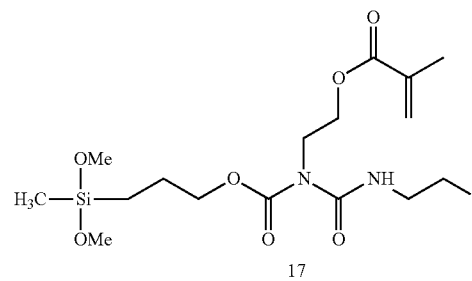

Allophanate silane (18) is synthesized by the reaction of 1-(triethoxysilyl)methanol with 2 equivalents of 2-Isocyanatoethyl methacrylate.

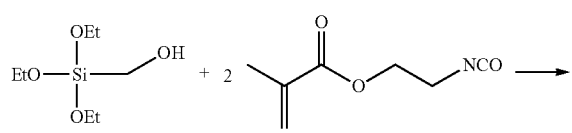

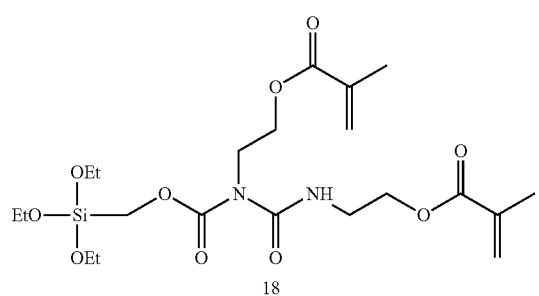

Thioallophanate silane (19) is synthesized by the reaction of 3-(trimethoxysilyl)-1-propanethiol with 2 equivalents of 2-Isocyanatoethyl methacrylate.

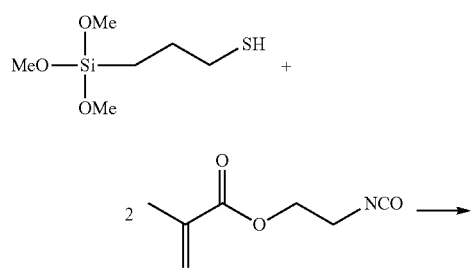

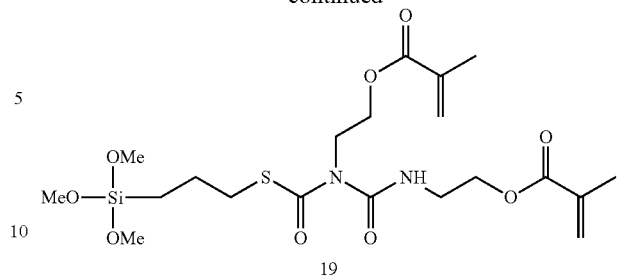

Biuret silane (20) is synthesized by the reaction of 3-(trimethoxysilyl)-1-propanamine with 2 equivalents of 2-Isocyanatoethyl methacrylate.

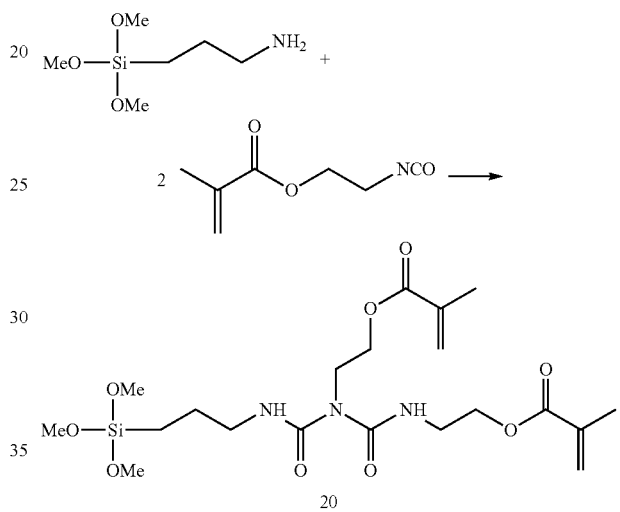

Synthesis of $(R^1O)_a R^2_b Si[-A(-NH-C(=O)-X-B[-Z-C(=O)C(=CH_2)R^3]_p)_d]_c$

The synthesis of the silane $(R^1O)_a R^2_b Si[-A(-NH-C(=O)-X-B[-Z-C(=O)C(=CH_2)R^3]_p)_d]_c$ is analogously tin or bismuth catalyzed, whereas here inversely the isocyanate group is located at the silane and the XH group at the (meth)acryl compound. Preferred catalysts are also dibutyltin dilaurate and bismuth neodecanoate. Under slight heating one XH group is reacted with one isocyanate group in an equivalent ratio. The reaction usually runs completely and can easily be monitored in the IR spectrum until the isocyanate band (2270 cm$^{-1}$) has completely disappeared.

$(R^1O)_a R^2_b Si[-A(-NCO)_d]_c + (c \times d)[R^3-C(=CH_2)C(=O)-Z-]_p B-XH \rightarrow (R^1O)_a R^2_b Si[-A(-NH-C(=O)-X-B[-Z-C(=O)C(=CH_2)R^3]_p)_d]_c$ Several commercially available starting compounds are shown in the following Tables 3 and 4.

TABLE 3

| | $(R^1O)_a R^2_b Si[-A(-NCO)_d]_c$ | | | | | | |
|---|---|---|---|---|---|---|---|
| CAS-Nr. | $R^1$ | $R^2$ | a | b | c | d | -A- |
| 15396-00-6 | Me | — | 3 | 0 | 1 | 1 | —(CH$_2$)$_3$— |
| 24801-88-5 | Et | — | 3 | 0 | 1 | 1 | —(CH$_2$)$_3$— |

TABLE 3-continued

| | | | $(R^1O)_a R^2_b Si[-A(-NCO)_d]_c$ | | | | |
|---|---|---|---|---|---|---|---|
| CAS-Nr. | $R^1$ | $R^2$ | a | b | c | d | -A- |
| 26115-72-0 | Me | Me | 2 | 1 | 1 | 1 | $-(CH_2)_3-$ |
| 33491-28-0 | Et | Me | 2 | 1 | 1 | 1 | $-(CH_2)_3-$ |
| 78450-75-6 | Me | — | 3 | 0 | 1 | 1 | $-CH_2-$ |
| 132112-76-6 | Et | — | 3 | 0 | 1 | 1 | $-CH_2-$ |
| 406679-89-8 | Me | Me | 2 | 1 | 1 | 1 | $-CH_2-$ |
| 20160-30-9 | Et | Me | 2 | 1 | 1 | 1 | $-CH_2-$ |
| 862546-89-2 | Et | — | 3 | 0 | 1 | 1 | $-(CH_2)_{10}-$ |

TABLE 4

| | | | $[R^3-C(=CH_2)C(=O)-Z-]_f B-XH$ | |
|---|---|---|---|---|
| CAS-Nr. | $R^3$ | Z | f | XH | -B- |
| 868-77-9 | Me | O | 1 | OH | $-(CH_2)_2-$ |
| 923-26-2 | Me | O | 1 | OH | $-CH_2CH(CH_3)-$ |
| 2761-09-3 | Me | O | 1 | OH | $-(CH_2)_3-$ |
| 997-46-6 | Me | O | 1 | OH | $-(CH_2)_4-$ |
| 13092-57-4 | Me | O | 1 | OH | $-(CH_2)_6-$ |
| 203245-10-7 | Me | O | 1 | OH | (cyclohexane) |
| 4855-07-6 | Me | O | 1 | OH | $-(CH_2)_8-$ |
| 56927-66-3 | Me | O | 1 | OH | $-(CH_2)_{10}-$ |
| 115372-36-6 | Me | O | 1 | OH | (adamantane) |
| 86282-42-0 | Me | O | 1 | OH | $-(CH_2)_{12}-$ |
| 2351-43-1 | Me | O | 1 | OH | $-(CH_2)_2O(CH_2)_2-$ |
| 2351-42-0 | Me | O | 1 | OH | $-(CH_2)_2O(CH_2)_2O(CH_2)_2-$ |
| 16926-87-7 | Me | O | 1 | OH | $-CH_2CH(CH_2OPh)-$ |
| 818-61-1 | H | O | 1 | OH | $-(CH_2)_2-$ |
| 999-61-1 | H | O | 1 | OH | $-CH_2CH(CH_3)-$ |
| 2761-08-2 | H | O | 1 | OH | $-(CH_2)_3-$ |
| 2478-10-6 | H | O | 1 | OH | $-(CH_2)_4-$ |
| 57198-94-4 | H | O | 1 | OH | $-(CH_2)_5-$ |
| 10095-14-4 | H | O | 1 | OH | $-(CH_2)_6-$ |
| 118915-15-4 | H | O | 1 | OH | $-(CH_2)_8-$ |
| 23117-38-6 | H | O | 1 | OH | $-(CH_2)_{10}-$ |
| 216581-76-9 | H | O | 1 | OH | (adamantane) |
| 13533-05-6 | H | O | 1 | OH | $-(CH_2)_2O(CH_2)_2-$ |
| 16695-45-7 | H | O | 1 | OH | $-(CH_2)_2O(CH_2)_2O(CH_2)_2-$ |
| 16969-10-1 | H | O | 1 | OH | $-CH_2CH(CH_2OPh)-$ |
| 1830-78-0 | Me | O | 2 | OH | (branched) |
| 101525-90-0 | Me | O | 2 | OH | (branched) |
| 1709-71-3 | H/Me | O | 2 | OH | (branched) |
| 433937-38-3 | H/Me | O | 2 | OH | (branched) |
| 1709-72-4 | H | O | 2 | OH | (branched) |
| 53151-63-6 | Me | O | 2 | OH | (branched) |
| 19727-16-3 | Me | O | 2 | OH | (branched) |
| 37275-47-1 | H | O | 2 | OH | (branched) |
| 3524-66-1 | Me | O | 3 | OH | (branched) |
| 3524-68-3 | H | O | 3 | OH | (branched) |
| 60506-81-2 | H | O | 5 | OH | (branched with O) |
| 7659-36-1 | Me | O | 1 | $NH_2$ | $-(CH_2)_2-$ |
| 7659-38-3 | H | O | 1 | $NH_2$ | $-(CH_2)_2-$ |
| 5238-56-2 | Me | NH | 1 | OH | $-(CH_2)_2-$ |
| 21442-01-3 | Me | NH | 1 | OH | $-CH_2CH(CH_3)-$ |
| 89911-51-3 | Me | NH | 1 | OH | $-(CH_2)_2O(CH_2)_2-$ |
| 89911-50-2 | H | NH | 1 | OH | $-(CH_2)_2O(CH_2)_2-$ |
| 96189-83-2 | Me | NH | 1 | OH | $-(CH_2)_2O(CH_2)_2O(CH_2)_2-$ |
| 63298-57-7 | Me | NH | 1 | $NH_2$ | $-(CH_2)_2-$ |
| 23918-29-8 | H | NH | 1 | $NH_2$ | $-(CH_2)_2-$ |

Some syntheses of the silanes $(R^1O)_a R^2_b Si[-A(-NH-C(=O)-X-B[-Z-C(=O)C(=CH_2)R^3]_f)_d]_c$ are shown by way of example hereinafter.

Silane (21) is synthesized by the reaction of 1-(trimethoxysilyl)methyl isocyanate with 2-hydroxyethyl methacrylate (HEMA).

-continued

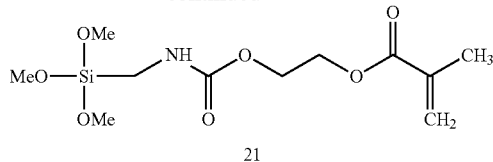

21

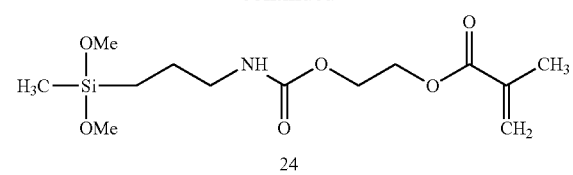

24

Silane (22) is synthesized by the reaction of 3-(trimethoxysilyl)propyl isocyanate with 2-hydroxyethyl methacrylate (HEMA).

Silane (25) is synthesized by the reaction of 1-(trimethoxysilyl)methyl isocyanate with 4-hydroxybutyl methacrylate.

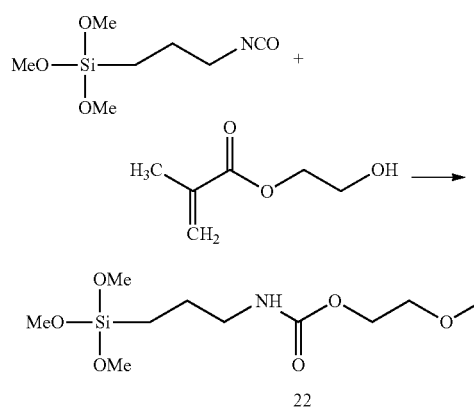

22

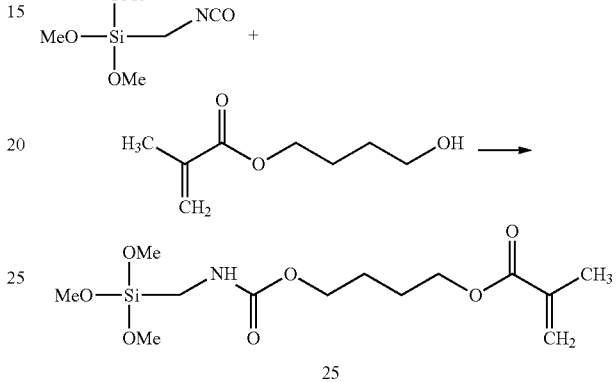

25

Silane (23) is synthesized by the reaction of 10-(triethoxysilyl)decyl isocyanate with 2-hydroxyethyl methacrylate (HEMA).

Silane (26) is synthesized by the reaction of 1-(trimethoxysilyl)methyl isocyanate with 6-hydroxyhexyl methacrylate.

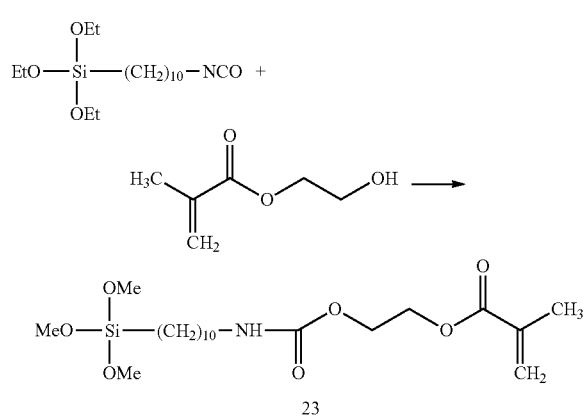

23

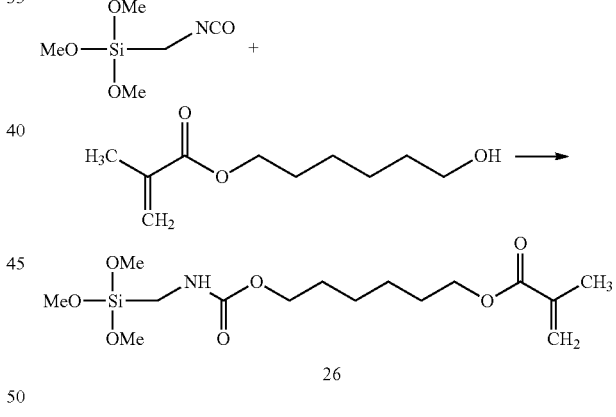

26

Silane (24) is synthesized by the reaction of 3-(methyldimethoxysilyl)propyl isocyanate with 2-hydroxyethyl methacrylate (HEMA).

Silane (27) is synthesized by the reaction of 1-(trimethoxysilyl)methyl isocyanate with 4-hydroxycyclohexyl methacrylate.

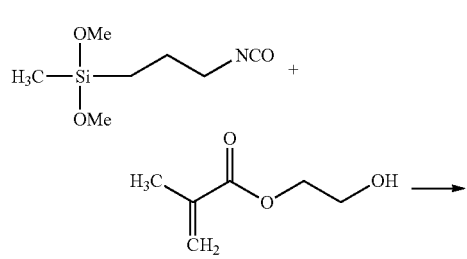

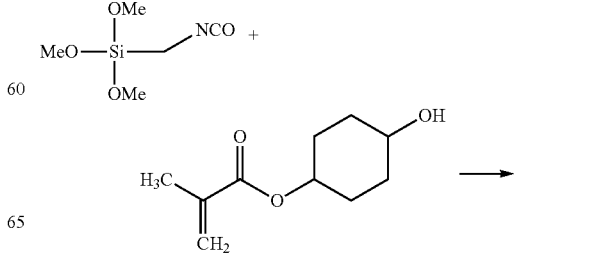

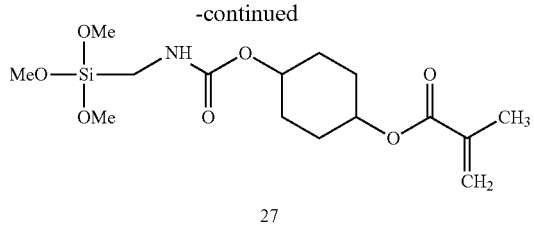

Silane (28) is synthesized by the reaction of 1-(trimethoxysilyl)methyl isocyanate with 3-hydroxyadamantan-1-yl-methacrylate.

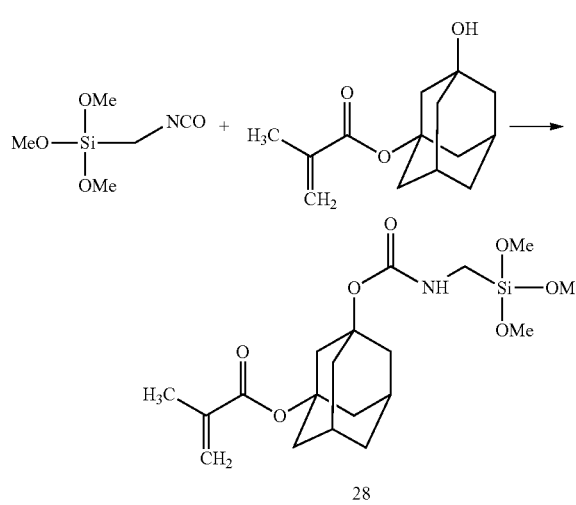

Silane (29) is synthesized by the reaction of 1-(trimethoxysilyl)methyl isocyanate with 2-(2-hydroxyethoxy)ethyl methacrylate.

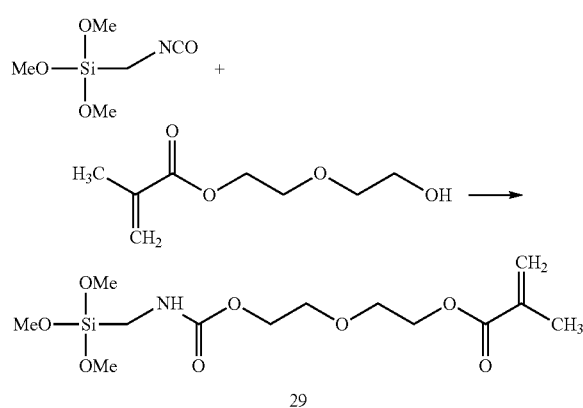

Silane (30) is synthesized by the reaction of 1-(trimethoxysilyl)methyl isocyanate with 2-[2-(2-hydroxyethoxy)ethoxy]ethyl methacrylate.

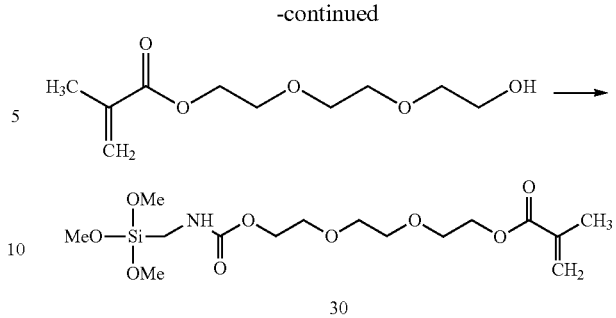

Silane (31) is synthesized by the reaction of 1-(trimethoxysilyl)methyl isocyanate with 2-hydroxy-3-phenoxy-1-propyl methacrylate.

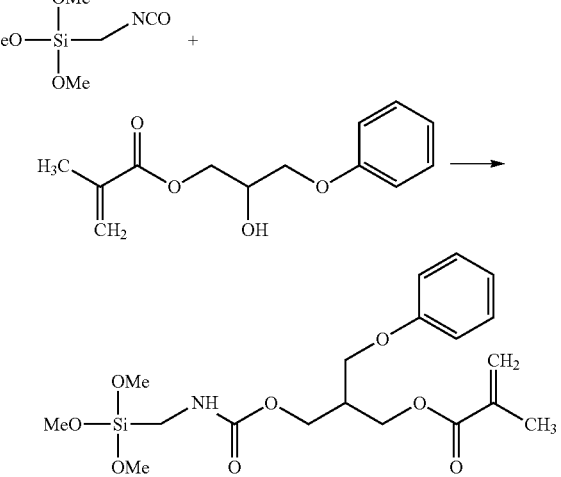

Silane (32) is synthesized by the reaction of 1-(trimethoxysilyl)methyl isocyanate with glycerol 1,3-dimethacrylate.

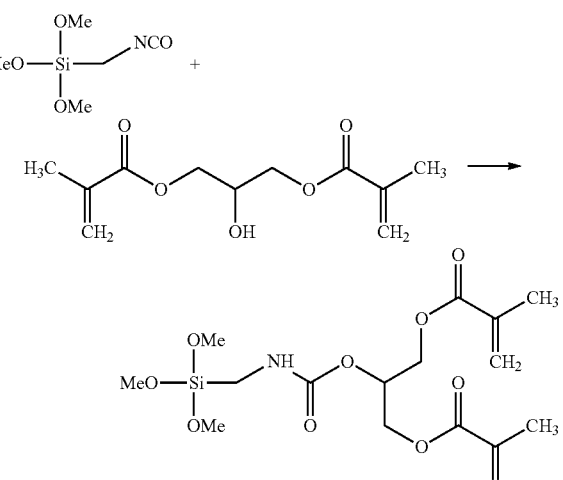

Silane (33) is synthesized by the reaction of 1-(trimethoxysilyl)methyl isocyanate with pentaerythritol trimethacrylate.

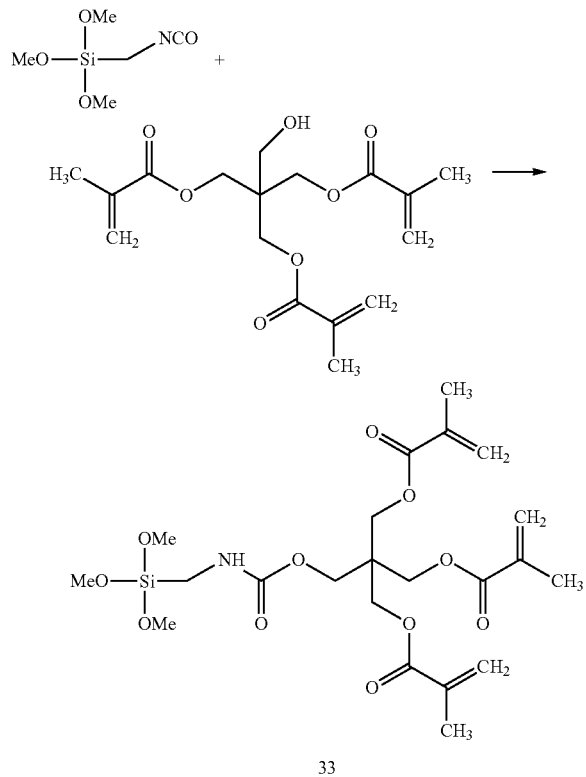

33

Silane (34) is synthesized by the reaction of 1-(trimethoxysilyl)methyl isocyanate with 2-aminoethyl methacrylate.

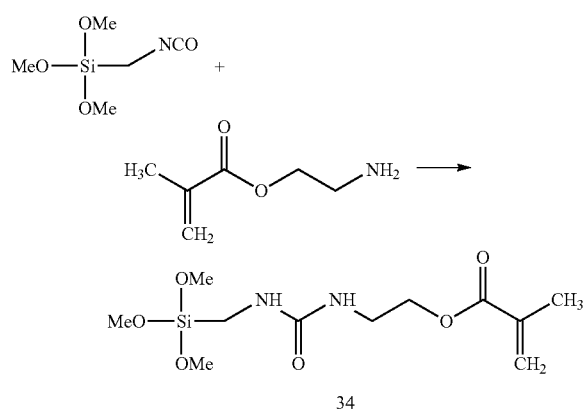

34

Silane (35) is synthesized by the reaction of 1-(trimethoxysilyl)methyl isocyanate with 2-hydroxyethyl methacrylamide.

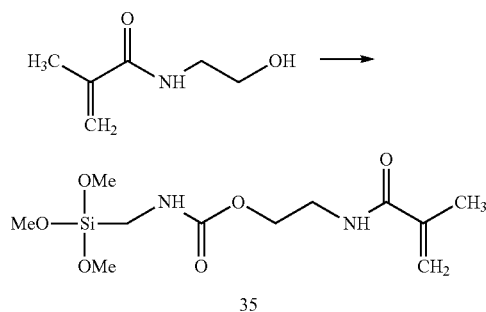

35

Synthesis of $(R^1O)_a R^2_b Si[-A(-NH-C(=O)-B[-Z-C(=O)C(=CH_2)R^3]_f)_d]_c$

The synthesis of the silane $(R^1O)_a R^2_b Si[-A(-NH-C(=O)-B[-Z-C(=O)C(=CH_2)R^3]_f)_d]_c$ is carried out tin or bismuth catalyzed by splitting off carbon dioxide from a silane with an isocyanate group and a carboxy-substituted methacrylate. Preferred catalysts are dibutyltin dilaurate and bismuth neodecanoate. Under slight heating one carboxyl group is reacted with one isocyanate group in an equivalent ratio. The reaction usually runs completely and can easily be monitored in the IR spectrum until the isocyanate band (2270 cm$^{-1}$) has completely disappeared.

$(R^1O)_a R^2_b Si[-A(-NCO)_d]_c + (c \times d)[R^3-C(=CH_2)C(=O)-Z-]_f B-COOH \rightarrow (R^1O)_a R^2_b Si[-A(-NH-C(=O)-B[-Z-C(=O)C(=CH_2)R^3]_f)_d]_c$ Several commercially available carboxyl methacrylate compounds are shown in the following Table 5. The commercially available compounds listed above in Table 3 are suitable as isocyanate-substituted silanes.

TABLE 5

| | [R$^3$—C(=CH$_2$)C(=O)—Z—]$_f$B—COOH | | | |
|---|---|---|---|---|
| CAS-Nr. | R$^3$ | Z | f | —B— |
| 141681-03-0 | H | O | 1 | —(CH$_2$)$_3$— |
| 59178-90-4 | Me | NH | 1 | —(CH$_2$)$_2$— |
| 16753-07-4 | H | NH | 1 | —(CH$_2$)$_2$— |
| 59178-91-5 | Me | NH | 1 | —(CH$_2$)$_3$— |
| 59178-91-5 | H | NH | 1 | —(CH$_2$)$_3$— |
| 20882-04-6 | Me | O | 1 | —(CH$_2$)$_2$OC(=O)—(CH$_2$)$_2$— |
| 112241-32-4 | Me | O | 1 | —(CH$_2$)$_3$OC(=O)—(CH$_2$)$_2$— |
| 51252-88-1 | Me | O | 1 | 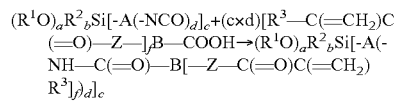 |
| 27697-00-3 | Me | O | 1 | |

TABLE 5-continued

| | [R³—C(=CH₂)C(=O)—Z—]<sub>f</sub>B—COOH | | | |
|---|---|---|---|---|
| CAS-Nr. | R³ | Z | f | —B— |
| 65859-45-2 | Me | O | 1 | 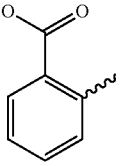 |

Some syntheses of the silanes $(R^1O)_aR^2{}_bSi[-A(-NH-C(=O)-B[-Z-C(=O)C(=CH_2)R^3]_f]_d]_c$ are shown byway of example hereinafter.

Silane (36) is synthesized by the reaction of 1-(trimethoxysilyl)propyl isocyanate with mono-2-(methacryloyloxy) ethyl succinate.

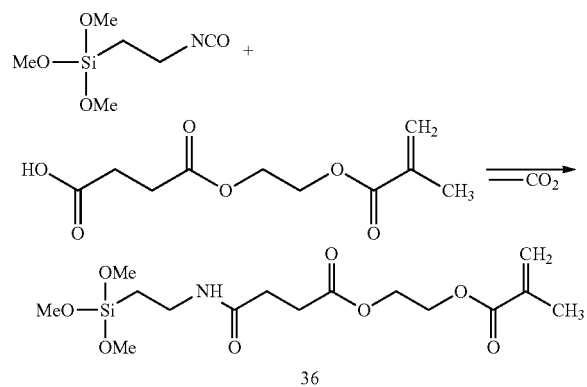

36

Silane (37) is synthesized by the reaction of 1-(trimethoxysilyl)methyl isocyanate with mono-2-(methacryloyloxy) ethyl succinate.

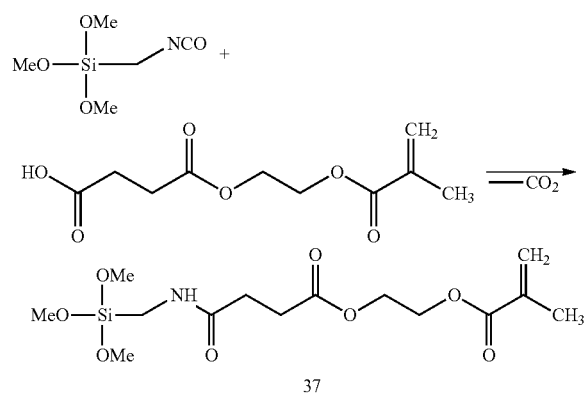

37

Silane (38) is synthesized by reaction of 1-(trimethoxysilyl)methyl isocyanate with Butanedioic acid, 1-[2-[(2-methyl-1-oxo-2-propen-1-yl)oxy]ethyl] ester

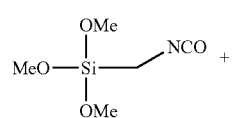

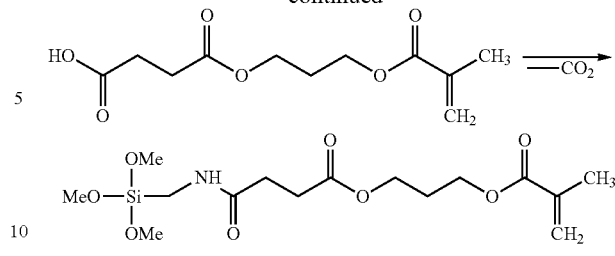

Silane (39) is synthesized by reaction of 1-(trimethoxysilyl)methyl isocyanate with 1,2-Cyclohexanedicarboxylic acid, 1-[2-[(2-methyl-1-oxo-2-propen-1-yl)oxy]ethyl] ester

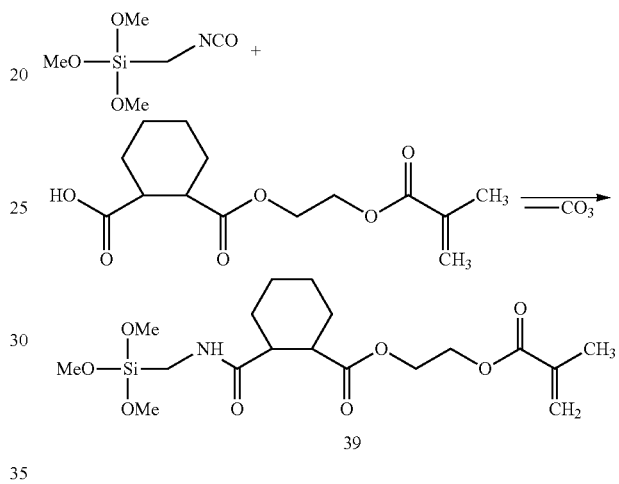

39

Silane (40) is synthesized by the reaction of 1-(trimethoxysilyl)methyl isocyanate with mono-2-(methacryloyloxy) ethyl phthalate.

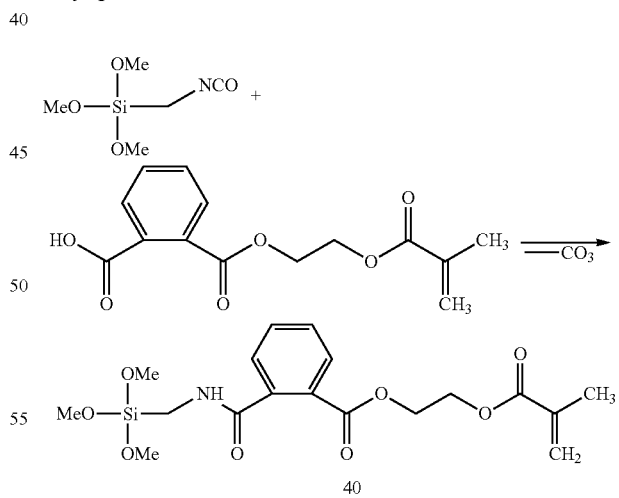

40

Synthesis of Silanes with Urethane, Thiourethane, Urea or Amide Groups Proceeding from Hydrosilanes Silanes with urethane, thiourethane, urea or amide groups can be prepared in a multi-stage synthesis by platinum catalyzed reaction of vinyl compounds with hydrosilanes. Corresponding synthesis are disclosed in US 2015/0299469 A1.

Synthesis of $(R^1O)_aR^2{_b}Si[\!-\!(CH_2)_2\!-\!CH(R^4)\!-\!NH\!-\!C(\!=\!O)\!-\!B[\!-\!Z\!-\!C(\!=\!O)C(\!=\!CH_2)R^3]_d]_c$ In a two-stage synthesis initially a carboxy methacrylate reacts with an allylamine.

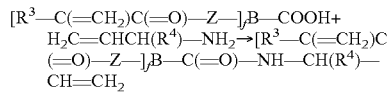

Commercially available carboxyl methacrylate compounds are shown in Table 5 above. Commercially available allylamines are listed in the following Table 6.

TABLE 6

| | $H_2C\!=\!CHCH(R^4)\!-\!NH_2$ |
|---|---|
| CAS-Nr. | $R^4$ |
| 107-11-9 | H |
| 34375-90-1 | Me |
| 70267-50-4 | Et |
| 4181-11-7 | n-Pr |
| 127209-34-1 | $^i$Pr |
| 5963-71-3 | n-Bu |
| 36024-39-2 | $^t$Bu |
| 4393-21-9 | Ph |
| 1186139-06-9 | (naphthyl) |

In the second synthesis stage the obtained vinyl compound is reacted with the hydrosilane $(R^1O)_aR^2{_b}SiH_c$ by platinum catalysis. Commercially available hydrosilanes are shown in Table 7. Further trialkoxysilanes $HSi(OR^1)_3$ can be produced according to EP 0 285 133 A2 by copper(II) hydroxide catalyzed reaction of silicon with alcohols.

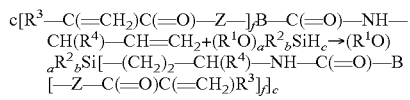

TABLE 7

| | $(R^1O)_aR^2{_b}SiH_c$ | | | | |
|---|---|---|---|---|---|
| CAS-Nr. | $R^1$ | $R^2$ | a | b | c |
| 2487-90-3 | Me | — | 3 | 0 | 1 |
| 998-30-1 | Et | — | 3 | 0 | 1 |
| 6485-85-4 | n-Pr | — | 3 | 0 | 1 |
| 6675-79-2 | $^i$Pr | — | 3 | 0 | 1 |
| 6485-86-5 | n-Bu | — | 3 | 0 | 1 |
| 16881-77-9 | Me | Me | 2 | 1 | 1 |
| 2031-62-1 | Et | Me | 2 | 1 | 1 |
| 54010-11-6 | $^i$Pr | Me | 2 | 1 | 1 |
| 2487-91-4 | n-Bu | Me | 2 | 1 | 1 |
| 19753-84-5 | Me | Et | 2 | 1 | 1 |
| 13175-88-7 | Et | Et | 2 | 1 | 1 |
| 18132-62-2 | n-Bu | Et | 2 | 1 | 1 |
| 163215-58-5 | Me | $^i$Pr | 2 | 1 | 1 |
| 5314-52-3 | Me | — | 2 | 0 | 2 |
| 18165-68-9 | Et | — | 2 | 0 | 2 |

Some syntheses of the silanes $(R^1O)_aR^2{_b}Si[\!-\!(CH_2)_2\!-\!CH(R^4)\!-\!NH\!-\!C(\!=\!O)\!-\!B[\!-\!Z\!-\!C(\!=\!O)C(\!=\!CH_2)R^3]_d]$ are shown by way of example hereinafter.

Initially the vinyl compound (41) is obtained by the reaction of mono-2-(methacryloyloxy)ethyl succinate with allylamine. The silane (42) is finally obtained by further platinum catalyzed reaction with triethoxysilane.

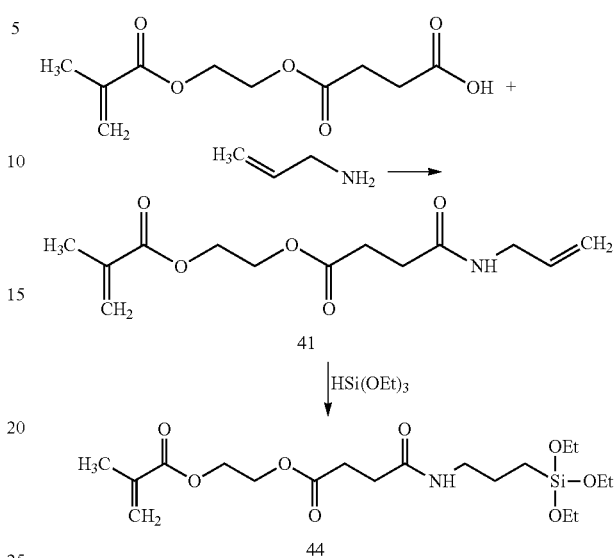

Initially the vinyl compound (43) is obtained by the reaction of 3-methacryloyl aminopropanoic acid with allylamine. The silane (44) is finally obtained by further platinum catalyzed reaction with triethoxysilane.

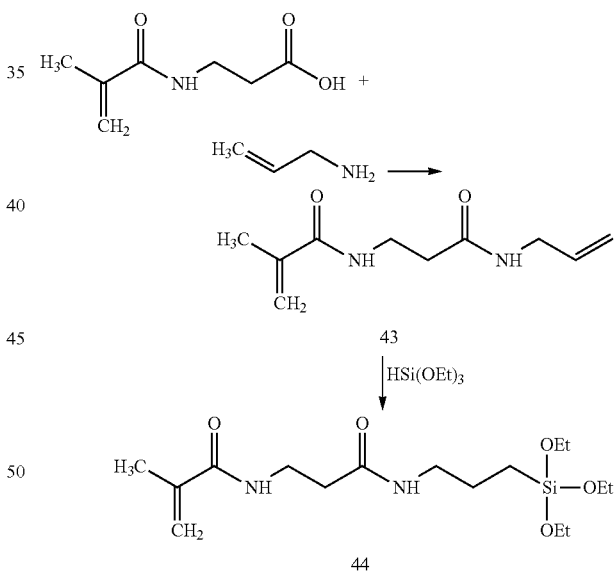

Initially the vinyl compound (45) is obtained by the reaction of 3-methacryloyl aminopropanoic acid with allylamine. The silane (46) is finally obtained by further platinum catalyzed reaction with methyldimethoxysilane.

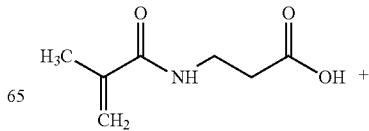

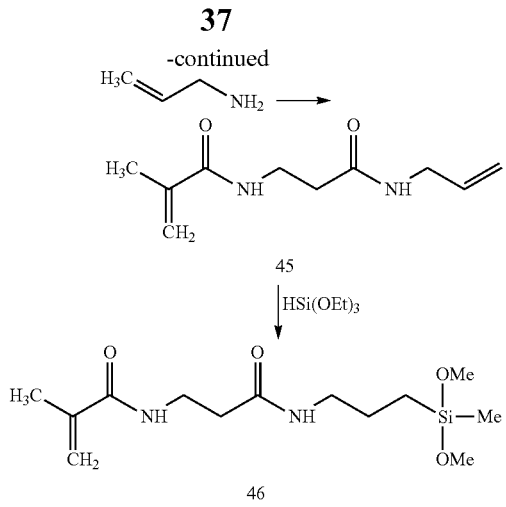

45

↓HSi(OEt)₃

46

Synthesis of $(R^1O)_aR^2{}_bSi[—(CH_2)_2—C(=O)—NH—B[—Z—C(=O)C(=CH_2)R^3]_d]_c$

In a two-stage synthesis initially an amino methacrylate is reacted with acryloyl chloride (CAS-Nr. 814-68-6). Preferably $R^3$ is a methyl group, because in this case the subsequent reaction with $(R^1O)_aR^2{}_bSiH_c$ is selectively at the acrylamide function. Commercially available amino methacrylates are shown in Table 4 (for XH=NH₂).

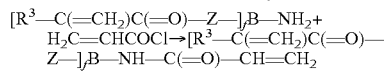

In the second synthesis stage the obtained vinyl compound is reacted with the hydrosilane $(R^1O)_aR^2{}_bSiH_c$ by platinum catalysis. Commercially available hydrosilanes are shown in Table 7.

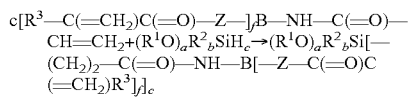

The vinyl compound (47) is obtained by the reaction of 2-aminoethyl methacrylate with acryloyl chloride. The silane (48) is finally obtained by further platinum catalyzed reaction with triethoxysilane.

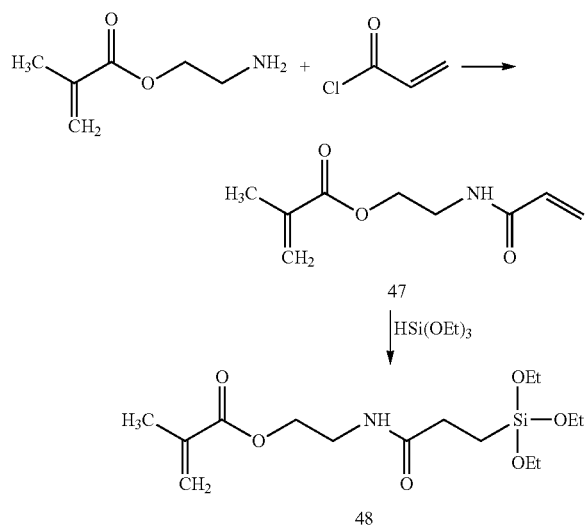

Synthesis of $(R^1O)_aR^2{}_bSi[—(CH_2)_2—CH(R^4)—X—C(=O)—NH—B[—Z—C(=O)C(=C)R^3]_d]_c$ In a two-stage synthesis initially an isocyanate-substituted methacrylate is reacted with a XH compound by tin or bismuth catalysis. Preferred catalysts are also dibutyltin dilaurate and bismuth neodecanoate. Under slight heating one XH group is reacted with an isocyanate group in an equimolar ratio. The reaction usually runs completely and can easily be monitored in the IR spectrum until the isocyanate band (2270 cm⁻¹) has completely disappeared. Commercially available isocyanate-substituted methacrylate compounds are shown above in Table 2. Commercially available XH compounds are shown in the following Table 8.

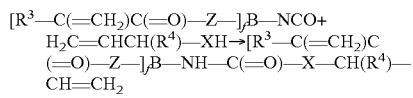

TABLE 8

| | H₂C=CHCH(R⁴)—XH | |
|---|---|---|
| CAS-Nr. | XH | R⁴ |
| 107-18-6 | OH | H |
| 598-32-3 | OH | Me |
| 616-25-1 | OH | Et |
| 4798-44-1 | OH | n-Pr |
| 4798-45-2 | OH | ⁱPr |
| 4938-52-7 | OH | n-Bu |
| 24580-44-7 | OH | ᵗBu |
| 3391-86-4 | OH | n-Pentyl |
| 21964-44-3 | OH | n-Hexyl |
| 51100-54-0 | OH | n-Heptyl |
| 35329-42-1 | OH | n-Octyl |
| 4393-06-0 | OH | Ph |
| 61619-02-1 | OH | 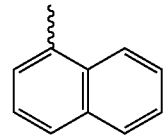 |
| 870-23-5 | SH | H |
| 5937-82-6 | SH | Me |
| 61758-08-5 | SH | n-Pentyl |
| 39707-48-7 | SH | Ph |
| 107-11-9 | NH₂ | H |
| 34375-90-1 | NH₂ | Me |
| 70267-50-4 | NH₂ | Et |
| 4181-11-7 | NH₂ | n-Pr |
| 127209-34-1 | NH₂ | ⁱPr |
| 5963-71-3 | NH₂ | n-Bu |
| 36024-39-2 | NH₂ | ᵗBu |
| 4393-21-9 | NH₂ | Ph |
| 1186139-06-9 | NH₂ | 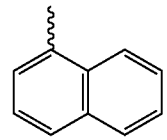 |

In the second synthesis stage the obtained vinyl compound is reacted with the hydrosilane $(R^1O)_aR^2{}_bSiH_c$ by platinum catalysis. Commercially available hydrosilanes are shown in Table 7.

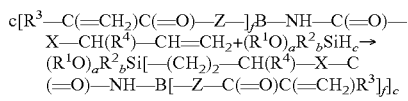

Some syntheses of the silanes $(R^1O)_aR^2_bSi[—(CH_2)_2—CH(R^4)—X—C(=O)—NH—B[—Z—C(=O)C(=CH_2)R^3]_d]_c$ are shown by way of example hereinafter.

The vinyl compound (49) is obtained by the reaction of 2-isocyanatoethyl methacrylate with 2-propen-1-ol. The silane (50) is finally obtained by further platinum catalyzed reaction with triethoxysilane.

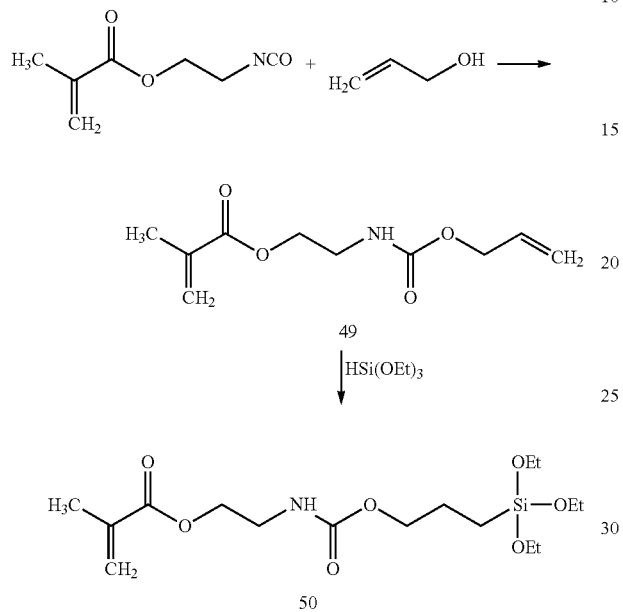

The vinyl compound (51) is obtained by the reaction of 2-isocyanatoethyl methacrylate with 2-propen-1-thiol. The silane (52) is finally obtained by further platinum catalyzed reaction with triethoxysilane.

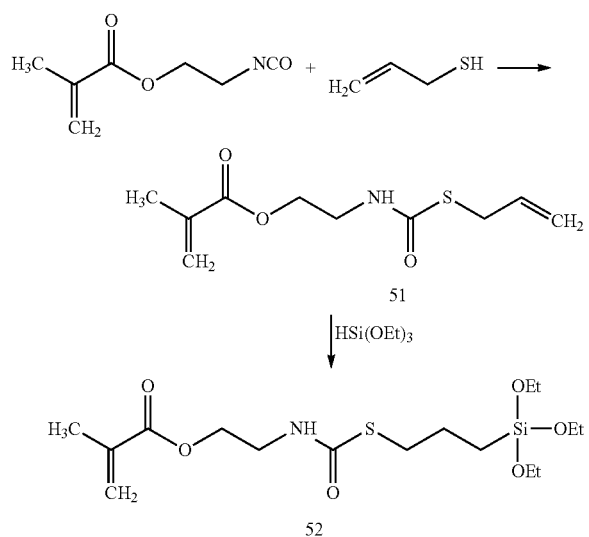

The vinyl compound (53) is obtained by the reaction of 2-isocyanatoethyl methacrylate with 3-amino-1-propene. The silane (54) is finally obtained by further platinum catalyzed reaction with triethoxysilane.

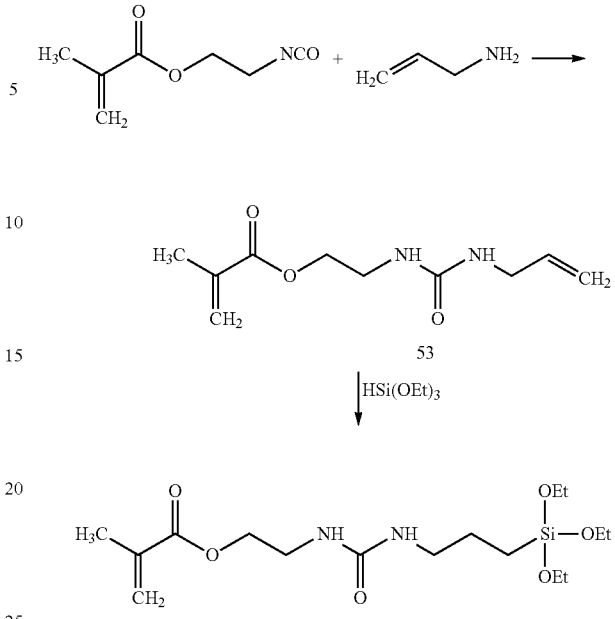

Synthesis of $(R^1O)_aR^2_bSi[—(CH_2)_2—CH(R^4)—X—C(=O)—N(—B[—Z—C(=O)C(=CH_2)R^3]_f)—C(=O)—NH—B[—Z—C(=O)C(=CH_2)R^3]_f]_c$ Analogous to the synthesis of $[R^3—C(=CH_2)C(=O)—Z—]_fB—NH—C(=O)—X—CH(R^4)—CH=CH_2$ also the silanes $(R^1O)_aR^2_bSi[—(CH_2)_2—CH(R^4)—X—C(=O)—N(—B[—Z—C(=O)C(=CH_2)R^3]_f)—C(=O)—NH—B[—Z—C(=O)C(=CH_2)R^3]_f]_c$ can be synthesized by a two-stage synthesis from XH compound and isocyanate-substituted methacrylate. Initially two equivalents of the isocyanate-substituted methacrylate are reacted with one equivalent of the XH compound by tin or bismuth cataysis, wherein the corresponding allophanates, thioallophanates or biurets are obtained. Preferred catalysts are also dibutyltin dilaurate and bismuth neodecanoate. Under slight heating the reaction usually runs completely and can easily be monitored in the IR spectrum until the isocyanate band (2270 cm$^{-1}$) has completely disappeared. Commercially available isocyanate-substituted methacryl compounds are shown above in Table 2. Commercially available XH compounds are shown in Table 8. Also here it is possible to react the XH groups with the isocyanate groups in a stoichiometry between 1:1 and 1:2, so that the second reaction stage can not be carried out completely and a mixture of urethane and allophanate or of thiourethane and thioallophanate or of urea and biuret is obtained. In the second synthesis storage the obtained vinyl compound is reacted with the hydrosilane $(R^1O)_aR^2_bSiH_c$ by platinum catalysis. Commercially available hydrosilanes are shown in Table 7.

The vinyl compound (55) is obtained by the reaction of two equivalents of 2-isocyanatoethyl methacrylate with 2-propen-1-ol. The allophanate silane (56) is finally obtained by further platinum catalyzed reaction with triethoxysilane.

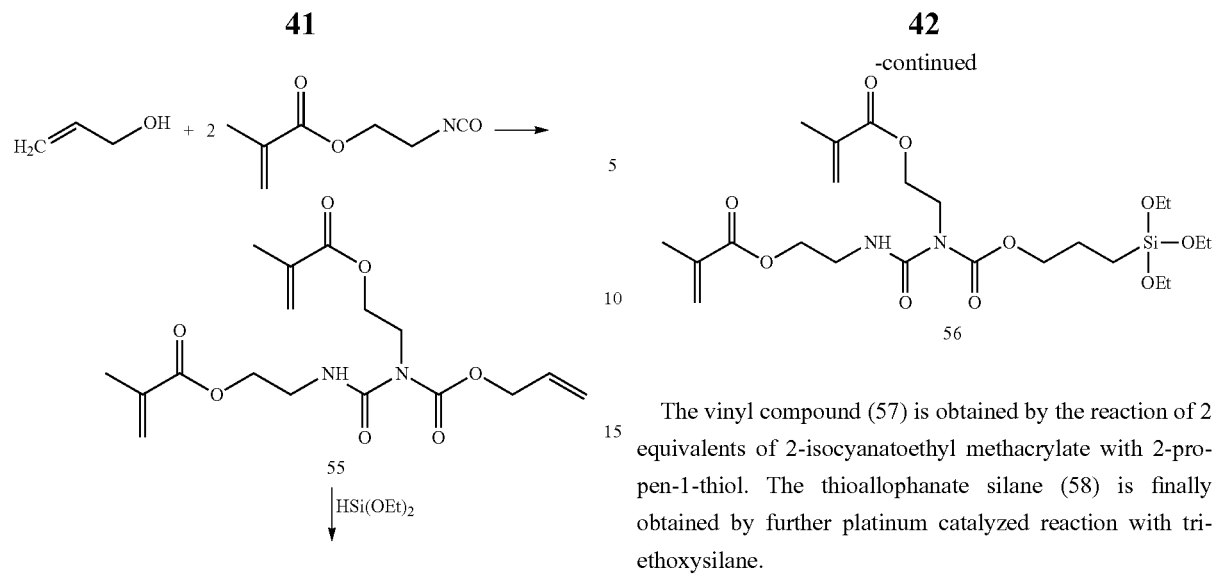
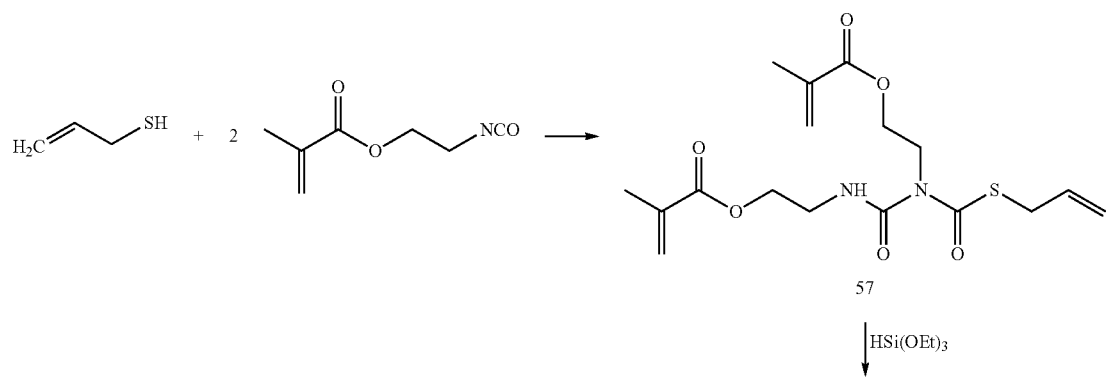
The vinyl compound (57) is obtained by the reaction of 2 equivalents of 2-isocyanatoethyl methacrylate with 2-propen-1-thiol. The thioallophanate silane (58) is finally obtained by further platinum catalyzed reaction with triethoxysilane.
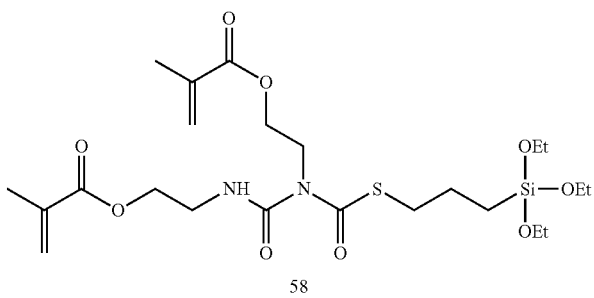

The vinyl compound (59) is obtained by the reaction of 2 equivalents of 2-isocyanatoethyl methacrylate with amino-1-propene. The biuret-silane (60) is finally obtained by further platinum catalyzed reaction with triethoxysilane.

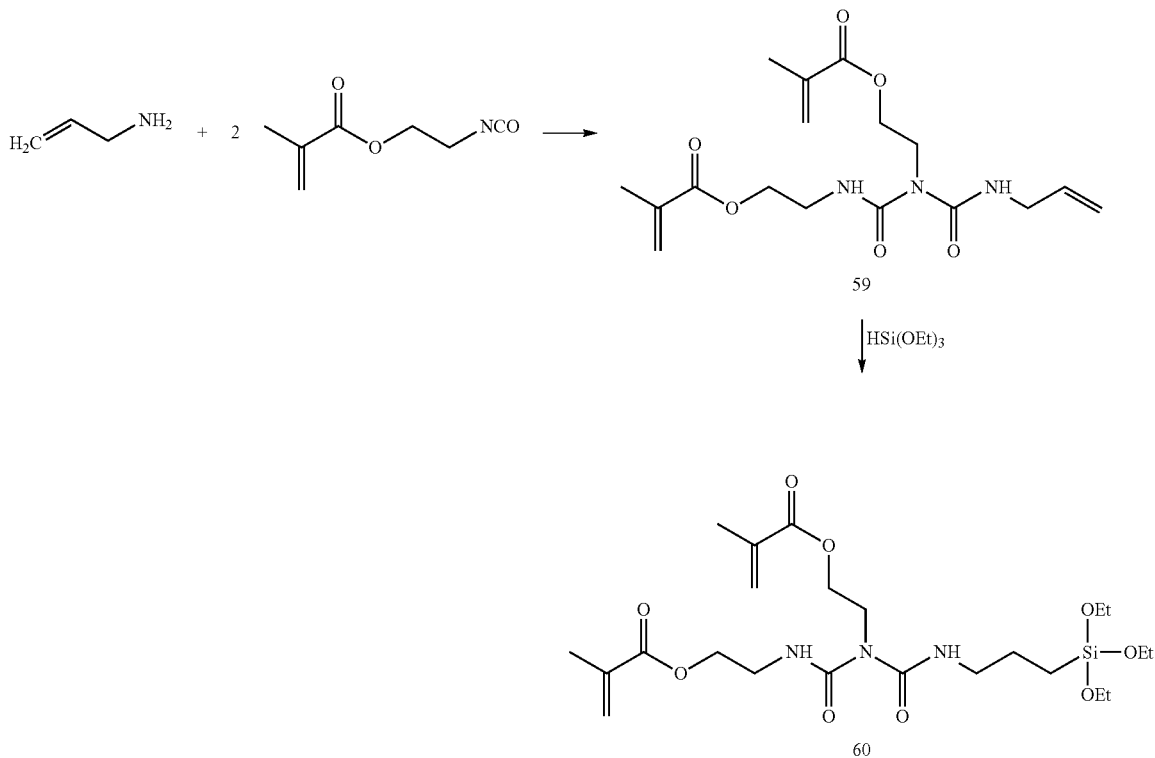

Synthesis of $(R^1O)_aR^2_bSi[-(CH_2)_2-CH(R^4)-NH-C(=O)-X-B[-Z-C(=O)C(=CH_2)R^3]_d]_c$ In a two-stage synthesis initially a OH, SH or NH$_2$ substituted (meth)acryl compound is reacted with an isocyanate-substituted vinyl compound by tin or bismuth catalysis. Preferred catalysts are also dibutyltin dilaurate and bismuth neodecanoate. Under slight heating one XH group is reacted with an isocyanate group in an equimolar ratio. The reaction usually runs complete and can easily be monitored in the IR spectrum until the isocyanate band (2270 cm$^{-1}$) has completely disappeared. Commercially available XH substituted (meth)acryl compounds are shown above in Table 4. Commercially available isocyanate-substituted vinyl compounds are shown in the following Table 9.

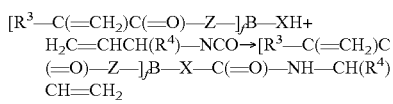

TABLE 9

| CAS-Nr. | H$_2$C=CHCH(R$^4$)—NCO<br>R$^4$ |
|---|---|
| 1476-23-9 | H |
| 155469-99-1 | Me |
| 55887-59-7 | Ph |

In the second synthesis stage the obtained vinyl compound is reacted with the hydrosilane $(R^1O)_aR^2_bSiH_c$ by platinum catalysis. Commercially available hydrosilanes are shown in Table 7.

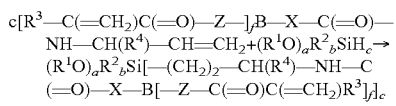

Some syntheses of the silanes $(R^1O)_aR^2_bSi[-(CH_2)_2-CH(R^4)-NH-C(=O)-X-B[-Z-C(=O)C(=CH_2)R^3]_d]_c$ are shown by way of example hereinafter.

The vinyl compound (61) is obtained by the reaction of 2-hydroxyethyl methacrylate (HEMA) with 3-isocyanato-1-propene. The silane (62) is finally obtained by further platinum catalyzed reaction with triethoxysilane.

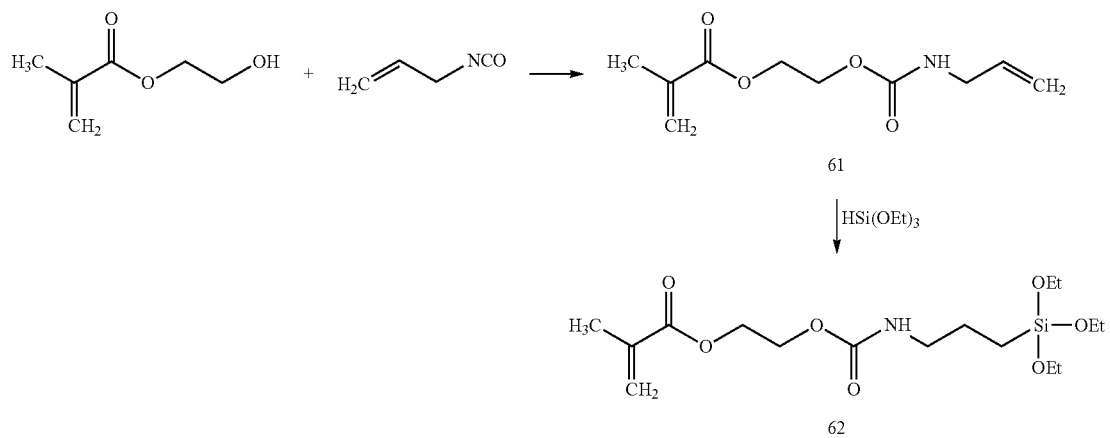
The vinyl compound (63) is obtained by the reaction of glycerol 1,3-dimethacrylate with 3-isocyanato-1-propene. The silane (64) is finally obtained by further platinum catalyzed reaction with triethoxysilane.
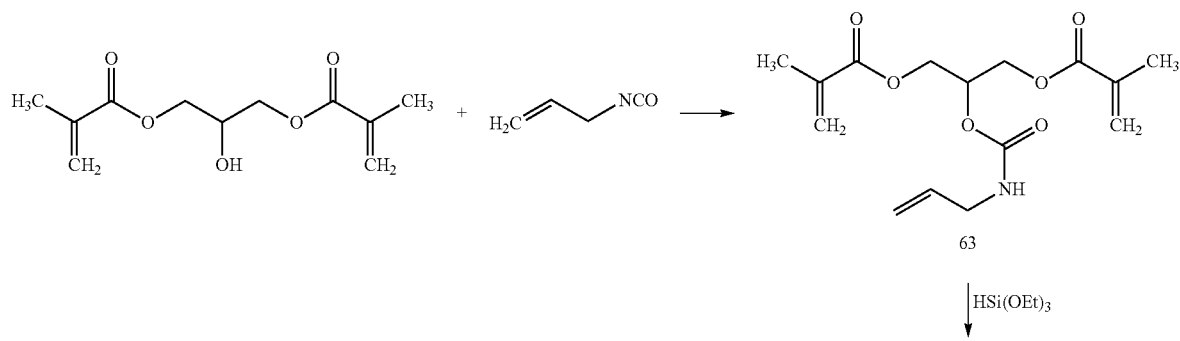
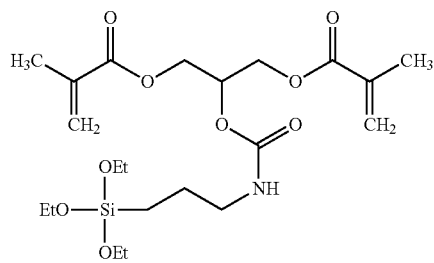

The vinyl compound (65) is obtained by the reaction of 2-hydroxypropyl methacrylate with 3-isocyanato-3-phenyl-1-propene. The silane (66) is finally obtained by further platinum catalyzed reaction with triethoxysilane.

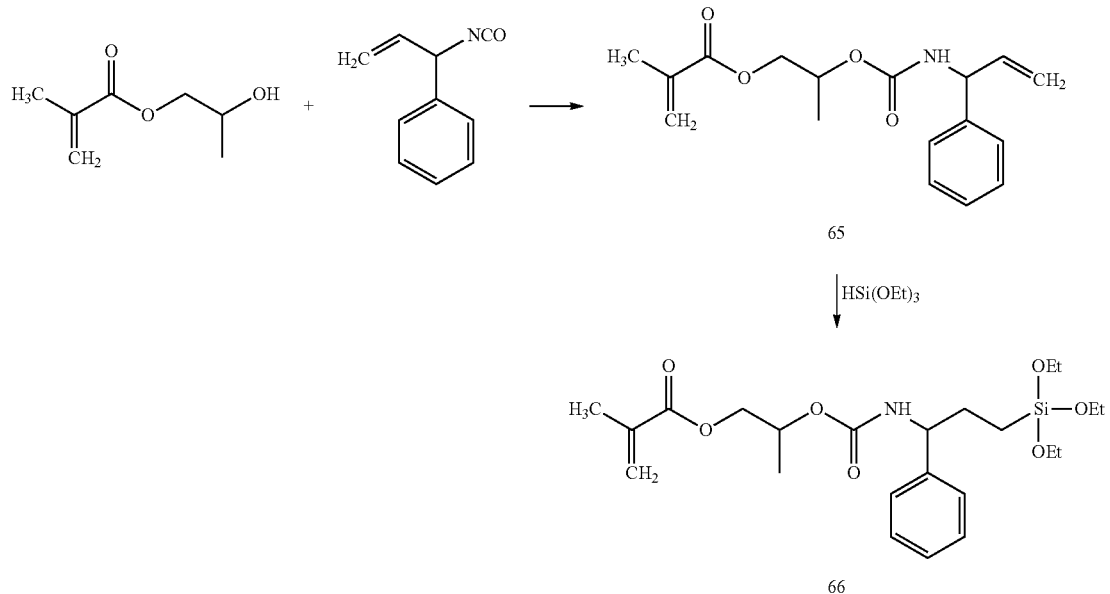

65

66

The vinyl compound (67) is obtained by the reaction of 2-aminoethyl methacrylate with 3-isocyanato-1-propene. The silane (68) is finally obtained by further platinum catalyzed reaction with triethoxysilane.

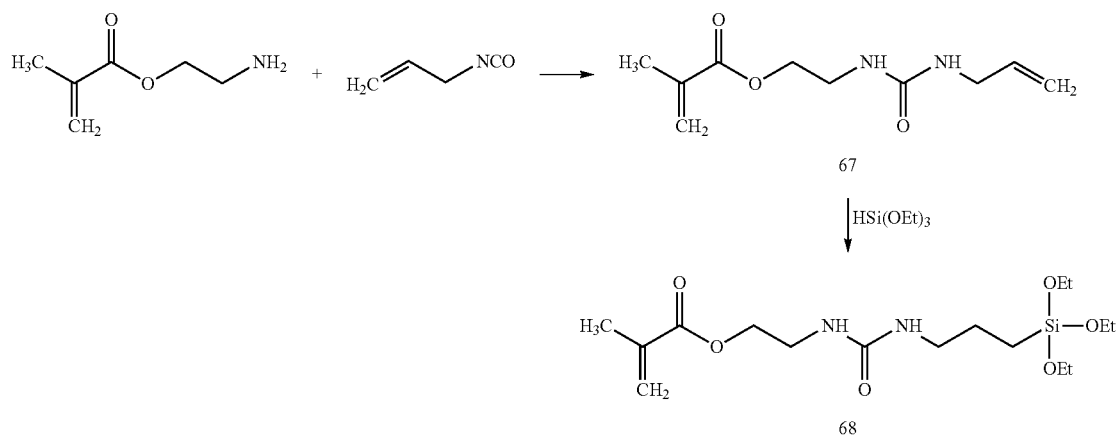

67

68

Synthesis of $(R^1O)_aR^2_bSi[-A(-C(=O)NHC(=O)NH\{-B[-Z-C(=O)C(=CH_2)R^3]_f\}_e)_d]_c$ Acylurea silanes can be synthesized, for example by a two-stage synthesis reacting vinyl functionalized amides with isocyanate-substituted methacrylates. Initially the amide reacts with an isocyanate-substituted vinyl compound by tin or bismuth cataysis. Preferred catalysts are also dibutyltin dilaurate and bismuth neodecanoate. Under slight heating an amide group is reacted with an isocyanate group in an equimolar ratio. The reaction usually runs completely and can easily be monitored in the IR spectrum until the isocyanate band (2270 cm$^{-1}$) has completely disappeared. Commercially available isocyanate-substituted vinyl compounds are shown in Table 2. Subsequently, a hydrosilylation is carried out. Commercially available hydrosilanes are shown in Table 7.

Thus, the reaction of 3-butenamide (CAS-Nr. 28446-58-4) with 2-isocyanatoethyl methacrylate and subsequent hydrosilylation with triethoxysilane results in the corresponding acylurea silane.

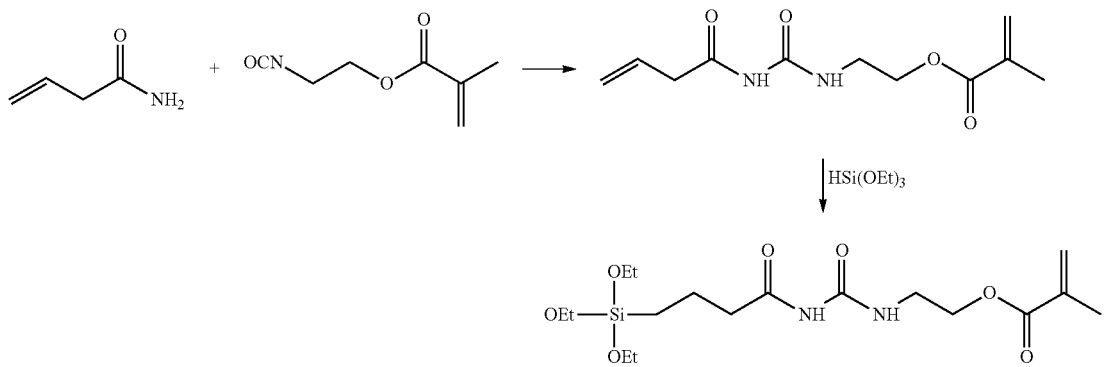

Synthesis of $(R^1O)_aR^2_bSi[-A(-NHC(=O)NHC(=O)\{-B[-Z-C(=O)C(=CH_2)R^3]_f\}_e)_d]_c$ Acylurea silanes can be synthesized, for example by a two-stage synthesis reacting an amide functionalized methacrylate with a vinyl substituted isocyanate. Initially the amide reacts with a vinyl substituted isocyanate compound by tin or bismuth cataysis. Preferred catalysts are also dibutyltin dilaurate and bismuth neodecanoate. Under slight heating an amide group reacts with a isocyanate group in an equimolar ratio. The reaction is usually complete and can easily be monitored in the IR spectrum until the isocyanate band (2270 cm$^{-1}$) has completely disappeared. Commercially available vinyl substituted isocyanate compounds are shown in Table 9. Subsequently, a hydrosilylation is carried out. Commercially available hydrosilanes are shown in Table 7.

Thus, the reaction of 2-carbamoylethyl methacrylate (CAS-Nr. 160031-60-7) with 3-isocyanato-1-propene and subsequent hydrosilylation with triethoxysilane results in the corresponding acylurea silane.

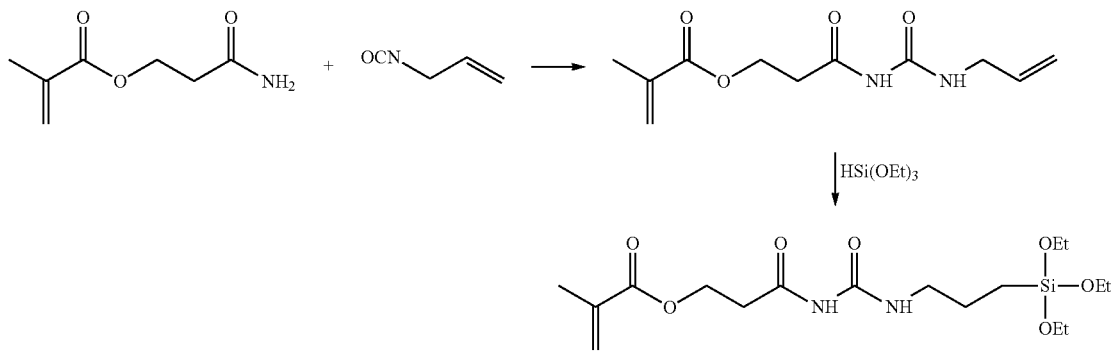

Silane $(R^1O)_aR^2_bSi[-A'(-PG)_f]_c$ (a2)

Silane (a2) corresponds to the formula $(R^1O)_aR^2_bSi[-A'(-PG)_f]_c$ wherein:
PG=polymerizable group,
A'=an organic linking group, connecting Si with PG and comprising 1 to 20 C-atoms and none of the groups —C(=O)NH—, —NHC(=O)—, —OC(=O)NH—, —NHC(=O)O—, —SC(=O)NH—, —NHC(=O)S—, —NHC(=O)NH—, —OC(=O)N(—C(=O)NH—)—, —SC(=O)N(—C(=O)NH—)—, —NHC(=O)N(—C(=O)NH—)— —C(=O)NHC(=O)NH—, or —NHC(=O)NHC(=O)—,
$R^1$=H or C1- to C4-Alkyl,
$R^2$=C1- to C4-Alkyl,
a=2 or 3,
b=0 or 1,
c=1 or 2,
f=1 to 5, and
a+b+c=4.

In a preferred embodiment, the polymerizable group PG is selected from the group consisting of —CH=CH$_2$, —C(CH$_3$)=CH$_2$, —C(=O)—CH=CH$_2$, —C(=O)—C(CH$_3$)=CH$_2$, —Z—C(=O)—CH=CH$_2$ and —Z—C(=O)—C(CH$_3$)=CH$_2$, wherein Z is selected from the group consisting of O and NH. In an especially preferred embodiment the polymerizable group PG is selected from the group consisting of —Z—C(=O)—CH=CH$_2$ and —Z—C(=O)—C(CH$_3$)=CH$_2$, wherein Z is selected from the group consisting of O and NH. In a particularly preferred embodiment the polymerizable group PG is selected from the group consisting of —Z—C(=O)—CH=CH$_2$ and —Z—C(=O)—C(CH$_3$)=CH$_2$, wherein Z=O.

In another preferred embodiment, the group PG is selected from the group consisting of structural elements comprising an oxirane unit, preferably an epoxycyclohexane unit or a norbornene epoxide unit. In one embodiment, PG is selected from the group consisting of:

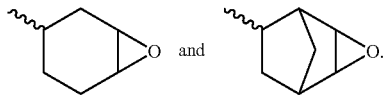

In one embodiment, the organic linking group A', connecting the Si-atom to the polymerizable group PG is a (f+1) valent, straight-chain, branched or cyclic group, comprising 1 to 20 C-atoms, and optionally may contain O atoms, S atoms, NR groups, ester groups or thioester groups.

In a preferred embodiment, the linking group A' is selected from the group consisting of —(CH$_2$)$_n$— wherein n=1 to 12, —(CH$_2$)$_n$—N(CH$_3$)—(CH$_2$)$_n$— wherein n=1 to 4, —(CH$_2$)$_n$N[(CH$_2$)$_n$—]$_2$ wherein n=1 to 4 and —(CH$_2$)$_n$—CH(R)—(CH$_2$)$_n$— wherein n=0 to 4 and R=methyl, ethyl, or phenyl, and

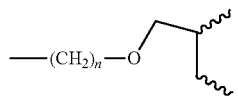

wherein n=1 to 6, wherein the bond arranged on the left is connected to the Si atom and the bond(s) arranged on the right is/are connected to the PG group(s).

In a particularly preferred embodiment, the linking group A' is —(CH$_2$)$_n$— wherein n=1 to 6.

In a preferred embodiment, the radical R$^1$ is selected from the group consisting of H, methyl and ethyl.

In a preferred embodiment, the index f is 1 or 2.

Several suitable silanes having the formula (R$^1$O)$_a$R$^2$$_b$Si[-A'(—Z—C(=O)C(=CH$_2$)R$^3$)$_f$]$_c$ are commercially available (see Table 10). Furthermore the silanes can be synthesized according to common synthesis methods. Some synthesis routes are disclosed for example in US 2015/0299469 A1.

TABLE 10

| | (R$^1$O)$_a$R$^2$$_b$Si[—A'(—Z—C(=O)C(=CH$_2$)R$^3$)$_f$]$_c$ | | | | | | | |
|---|---|---|---|---|---|---|---|---|
| CAS-Nr. | R$^1$ | R$^2$ | R$^3$ | Z | a | b | c | f | -A'- |
| 21134-38-3 | Me | — | H | O | 3 | 0 | 1 | 1 | —CH$_2$— |
| 54586-78-6 | Me | — | Me | O | 3 | 0 | 1 | 1 | —CH$_2$— |
| 78884-71-6 | Et | — | H | O | 3 | 0 | 1 | 1 | —CH$_2$— |
| 5577-72-0 | Et | — | Me | O | 3 | 0 | 1 | 1 | —CH$_2$— |
| 121177-93-3 | Me | Me | Me | O | 2 | 1 | 1 | 1 | —CH$_2$— |
| 3978-58-3 | Et | Me | Me | O | 2 | 1 | 1 | 1 | —CH$_2$— |
| 4369-14-6 | Me | — | H | O | 3 | 0 | 1 | 1 | —(CH$_2$)$_3$— |
| 2530-85-0 | Me | — | Me | O | 3 | 0 | 1 | 1 | —(CH$_2$)$_3$— |
| 57577-96-5 | Me | — | H | NH | 3 | 0 | 1 | 1 | —(CH$_2$)$_3$— |
| 10310-41-5 | Me | — | Me | NH | 3 | 0 | 1 | 1 | —(CH$_2$)$_3$— |
| 20208-39-3 | Et | — | H | O | 3 | 0 | 1 | 1 | —(CH$_2$)$_3$— |
| 21142-29-0 | Et | — | Me | O | 3 | 0 | 1 | 1 | —(CH$_2$)$_3$— |
| 80750-05-6 | $^i$Pr | — | Me | O | 3 | 0 | 1 | 1 | —(CH$_2$)$_3$— |
| 13732-00-8 | Me | Me | H | O | 2 | 1 | 1 | 1 | —(CH$_2$)$_3$— |
| 14513-34-9 | Me | Me | Me | O | 2 | 1 | 1 | 1 | —(CH$_2$)$_3$— |
| 146666-71-9 | Et | Me | H | O | 2 | 1 | 1 | 1 | —(CH$_2$)$_3$— |
| 65100-04-1 | Et | Me | Me | O | 2 | 1 | 1 | 1 | —(CH$_2$)$_3$— |

Synthesis of (R$^1$O)$_a$R$^2$$_b$Si[-A'(—Z—C(=O)C(=CH$_2$)R$^3$)$_f$]$_c$

Suitable silanes are obtained from the reaction of OH, SH or NH$_2$ functionalized silanes with methacryloyl chloride. The reaction is usually simple and quantitative. Alternatively methacrylic acids or other methacrylic acid derivates can also be used in common procedures. Suitable commercially available ZH functionalized silanes are listed in Table 11.

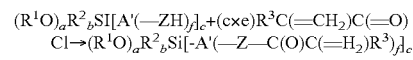

TABLE 11

| | (R$^1$O)$_a$R$^2$$_b$SI[—A'(—ZH)$_f$]$_c$ | | | | | | |
|---|---|---|---|---|---|---|---|
| CAS-Nr. | R$^1$ | R$^2$ | ZH | a | b | c | f | -A'- |
| 53764-54-8 | Me | — | OH | 3 | 0 | 1 | 1 | —(CH$_2$)$_3$— |
| 53394-61-9 | Et | — | OH | 3 | 0 | 1 | 1 | —(CH$_2$)$_3$— |
| 99697-20-8 | Me | Me | OH | 2 | 1 | 1 | 1 | —(CH$_2$)$_3$— |
| 162781-70-6 | Et | — | OH | 3 | 0 | 1 | 1 | —(CH$_2$)$_1$— |
| 13822-56-5 | Me | — | NH$_2$ | 3 | 0 | 1 | 1 | —(CH$_2$)$_3$— |
| 3663-44-3 | Me | Me | NH$_2$ | 2 | 1 | 1 | 1 | —(CH$_2$)$_3$— |
| 3179-76-8 | Et | Me | NH$_2$ | 2 | 1 | 1 | 1 | —(CH$_2$)$_3$— |
| 71408-48-5 | Me | — | NH$_2$ | 3 | 0 | 1 | 1 | —(CH$_2$)$_1$— |
| 18306-83-7 | Et | — | NH$_2$ | 3 | 0 | 1 | 1 | —(CH$_2$)$_1$— |
| 51749-36-1 | Me | — | NH$_2$ | 2 | 0 | 2 | 1 | —(CH$_2$)$_3$— |
| 53746-12-6 | Et | — | NH$_2$ | 2 | 0 | 2 | 1 | —(CH$_2$)$_3$— |
| 330457-46-0 | Me | — | OH | 3 | 0 | 1 | 1 | —(CH$_2$)$_3$—N(CH$_3$)—(CH$_2$)$_2$— |
| 24801-87-4 | Me | — | OH | 3 | 0 | 1 | 2 | —(CH$_2$)$_3$N[(CH$_2$)$_2$—]$_2$ |
| 7538-44-5 | Et | — | OH | 3 | 0 | 1 | 2 | —(CH$_2$)$_3$N[(CH$_2$)$_2$—]$_2$ |

Some syntheses of the silanes (R$^1$O)$_a$R$^2$$_b$Si[-A'(—Z—C(=O)C(=CH$_2$)R$^3$)$_f$]$_c$ are shown by way of example hereinafter.

Silane (69) is synthesized by the reaction of 3-(trimethoxysilyl)-1-propanol with methacryloyl chloride.

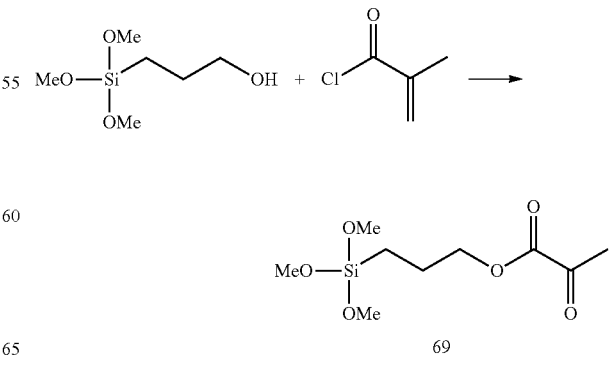

69

Silane (70) is synthesized by the reaction of 3-(methyl-dimethoxysilyl)-1-propanol with methacryloyl chloride.

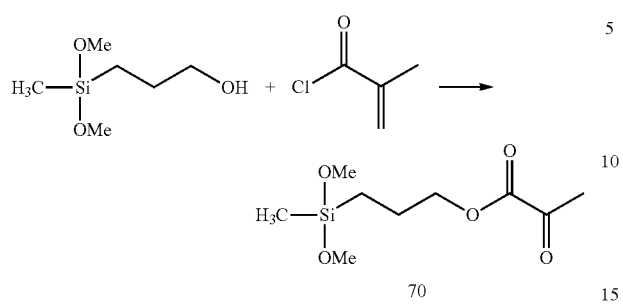

Silane (71) is synthesized by the reaction of 1-(trimethoxysilyl)-methanol with methacryloyl chloride.

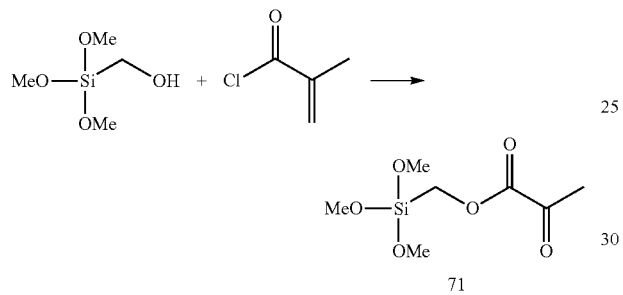

Silane (72) is synthesized by the reaction of 1-(methyl-dimethoxysilyl)-methanol with methacryloyl chloride.

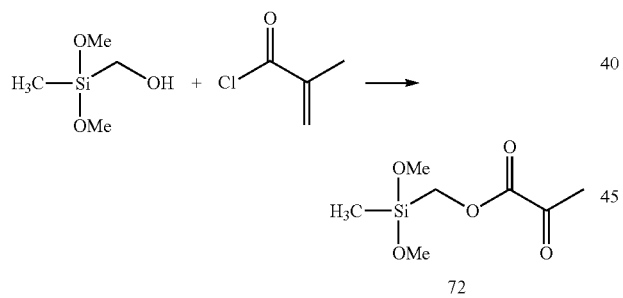

Silane (73) is synthesized by the reaction of 2,2'-[[3-(triethoxysilyl)propyl]imino]bis[ethanol] with two equivalents of methacryloyl chloride.

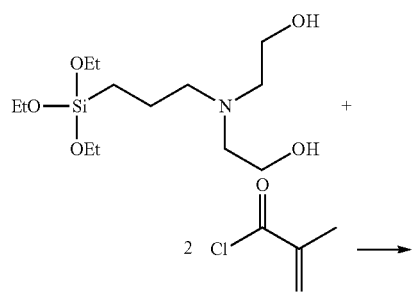

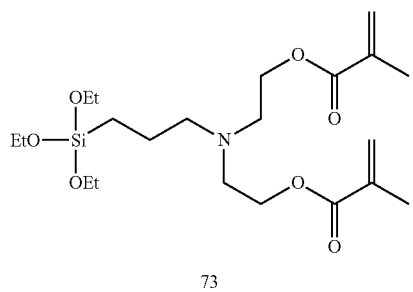

Synthesis of Silanes Proceedinq of Hydrosilanes

Suitable silanes can be prepared in a multi-stage synthesis by platinum catalyzed reaction of vinyl compounds with hydrosilanes. Corresponding syntheses are disclosed in US 2015/0299469 A1.

Synthesis of $(R^1O)_a R^2{}_b Si[-(CH_2)_{(n+2)}-Z-C(=O)C(=CH_2)R^3]_c$

In a two-stage synthesis, initially methacryloyl chloride is reacted with a OH or NH$_2$ functionalized terminal vinyl compound. Alternatively methacrylic acids or other methacrylic acid derivates can also be used in common procedures.

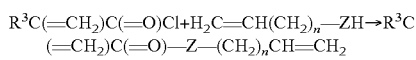

$R^3C(=CH_2)C(=O)Cl+H_2C=CH(CH_2)_n-ZH \rightarrow R^3C(=CH_2)C(=O)-Z-(CH_2)_n CH=CH_2$

TABLE 12

| | $H_2C=CH(CH_2)_n-ZH$ | |
|---|---|---|
| CAS-Nr. | n | ZH |
| 107-18-6 | 1 | OH |
| 627-27-0 | 2 | OH |
| 821-09-0 | 3 | OH |
| 821-41-0 | 4 | OH |
| 4117-10-6 | 5 | OH |
| 13175-44-5 | 6 | OH |
| 107-11-9 | 1 | NH$_2$ |
| 2524-49-4 | 2 | NH$_2$ |
| 22537-07-1 | 3 | NH$_2$ |
| 34825-70-2 | 4 | NH$_2$ |
| 151626-26-5 | 5 | NH$_2$ |
| 82223-49-2 | 6 | NH$_2$ |

In the second synthesis stage the obtained vinyl compound is reacted with the hydrosilane $(R^1O)_a R^2{}_b SiH_c$ by platinum catalysis. Commercially available hydrosilanes are shown above in Table 7.

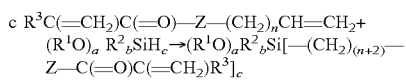

$c\ R^3C(=CH_2)C(=O)-Z-(CH_2)_n CH=CH_2 + (R^1O)_a R^2{}_b SiH_c \rightarrow (R^1O)_a R^2{}_b Si[-(CH_2)_{(n+2)}-Z-C(=O)C(=CH_2)R^3]_c$ Some syntheses of the silanes $(R^1O)_a R^2{}_b Si[-(CH_2)_{(n+2)}-Z-C(=O)C(=CH_2)R^3]_c$ are shown by way of example hereinafter.

The vinyl compound (74) is obtained by the reaction of methacryloyl chloride with 2-propen-1-ol. The silane (75) is finally obtained by further platinum catalyzed reaction with triethoxysilane.

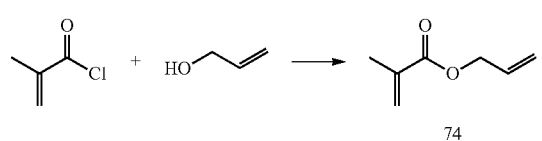

74

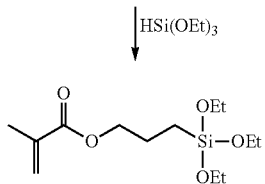

75

The vinyl compound (74 see above) is obtained by the reaction of methacryloyl chloride with 2-propen-1-ol. The silane (76) is finally obtained by further platinum catalyzed reaction with methyldimethoxysilane.

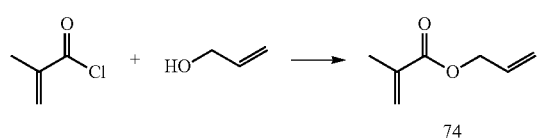

74

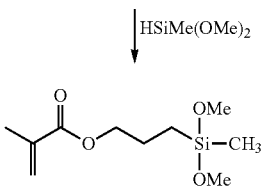

76

The vinyl compound (77) is obtained by the reaction of methacryloyl chloride with 4-penten-1-ol. The silane (78) is finally obtained by further platinum catalyzed reaction with triethoxysilane.

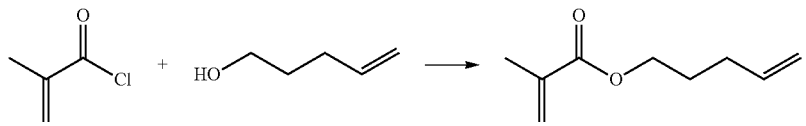

77

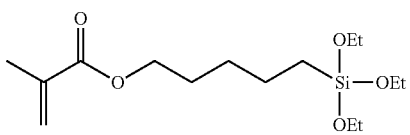

78

The vinyl compound (79) is obtained by the reaction of methacryloyl chloride with allylamine. The silane (80) is finally obtained by further platinum catalyzed reaction with triethoxysilane.

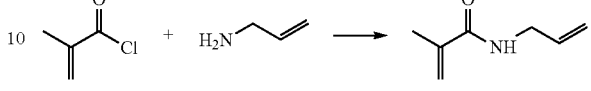

79

80

The vinyl compound (79 see above) is obtained by the reaction of methacryloyl chloride with allylamine. The silane (81) is finally obtained by further platinum catalyzed reaction with methyldimethoxysilane.

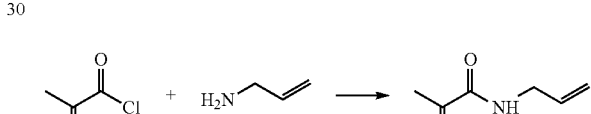

79

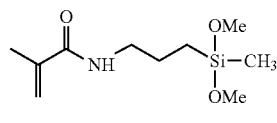

81

The vinyl compound (82) is obtained by the reaction of methacryloyl chloride with 4-penten-1-amine. The silane (83) is finally obtained by further platinum catalyzed reaction with triethoxysilane.

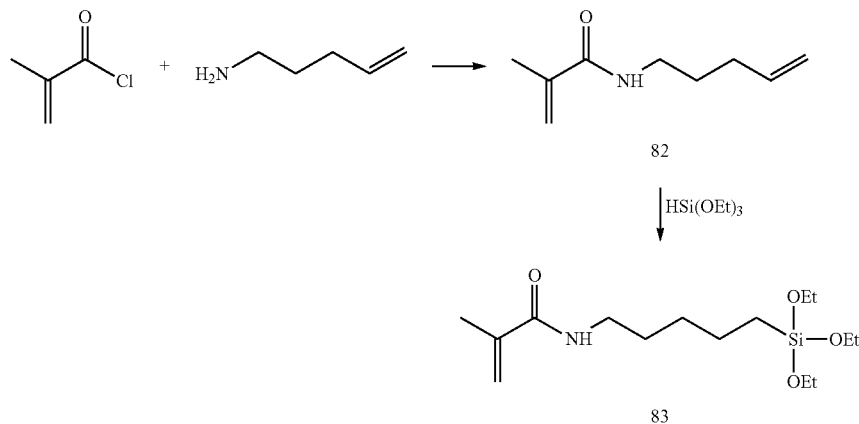

Synthesis of $(R^1O)_aR^2{}_bSi[-A'(-Z-C(=O)C(=CH_2)R^3)]_c$

Suitable OH functionalized silanes are prepared by a reaction of glycidoxy functionalized silanes with methacrylic acid. The synthesis is usually simple and quantitative. Suitable silanes with two methacrylate groups can be obtained by further reaction with methacryloyl chloride or another methacrylic acid derivate. Suitable commercially available glycidoxy functionalized silanes are listed in Table 13.

TABLE 13

$(R^1O)_aR^2{}_bSi[-A''-O-CH_2-\overset{O}{\triangle}]_c$

| CAS-Nr. | $R^1$ | $R^2$ | a | b | c | —A"— |
|---|---|---|---|---|---|---|
| 215301-24-9 | Et | Me | 2 | 1 | 1 | —CH$_2$— |
| 2530-83-8 | Me | — | 3 | 0 | 1 | —(CH$_2$)$_3$— |
| 2602-34-8 | Et | — | 3 | 0 | 1 | —(CH$_2$)$_3$— |
| 98899-94-6 | n-Pr | — | 3 | 0 | 1 | —(CH$_2$)$_3$— |
| 252255-95-1 | $^i$Pr | — | 3 | 0 | 1 | —(CH$_2$)$_3$— |
| 65799-47-5 | Me | Me | 2 | 1 | 1 | —(CH$_2$)$_3$— |
| 2897-60-1 | Et | Me | 2 | 1 | 1 | —(CH$_2$)$_3$— |
| 131535-64-3 | n-Pr | n-Pr | 2 | 1 | 1 | —(CH$_2$)$_2$— |
| 233765-90-7 | Me | — | 3 | 0 | 1 | —CH(CH$_3$)CH$_2$— |
| 139485-54-4 | Et | — | 3 | 0 | 1 | —CH(CH$_3$)CH$_2$— |
| 70187-33-6 | Me | — | 3 | 0 | 1 | —CH$_2$CH(CH$_3$)— |
| 20411-24-1 | Me | — | 2 | 0 | 2 | —(CH$_2$)$_3$— |

Furthermore suitable glycidoxy functionalized silanes can be obtained by platinum-catalyzed reaction of glycidoxy functionalized vinyl compounds with $(R^1O)_aR^2{}_bSiH_c$ (see Table 7). The preferred glycidoxy functionalized vinyl compound is 1,2-epoxy-3-allyloxypropane (CAS-Nr. 106-92-3). Suitable glycidoxy functionalized vinyl compounds can also be synthesized by known syntheses. For example glycidol (CAS-Nr. 556-52-5) can react with 3-butenoyl chloride (CAS-Nr. 1470-91-3), 4-pentenoyl chloride (CAS-Nr. 39716-58-0) or 5-hexenoyl chloride (CAS-Nr. 36394-07-7). Instead of glycidol, substituted glycidol derivates can also be used. Commercially available glycidol derivates are shown in Table 14.

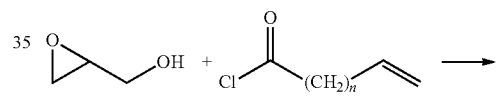

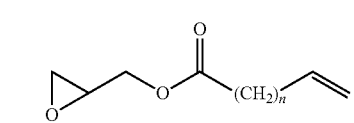

TABLE 14

| CAS-Nr. | R |
|---|---|
| 556-52-5 | H |
| 765-44-6 | Me |
| 4798-48-5 | Et |
| 33143-44-1 | Ph |

Silane (84) is synthesized by the reaction of 3-glycidoxypropyl trimethoxysilane with methacrylic acid. Further reaction with methacryloyl chloride provides the silane (85).

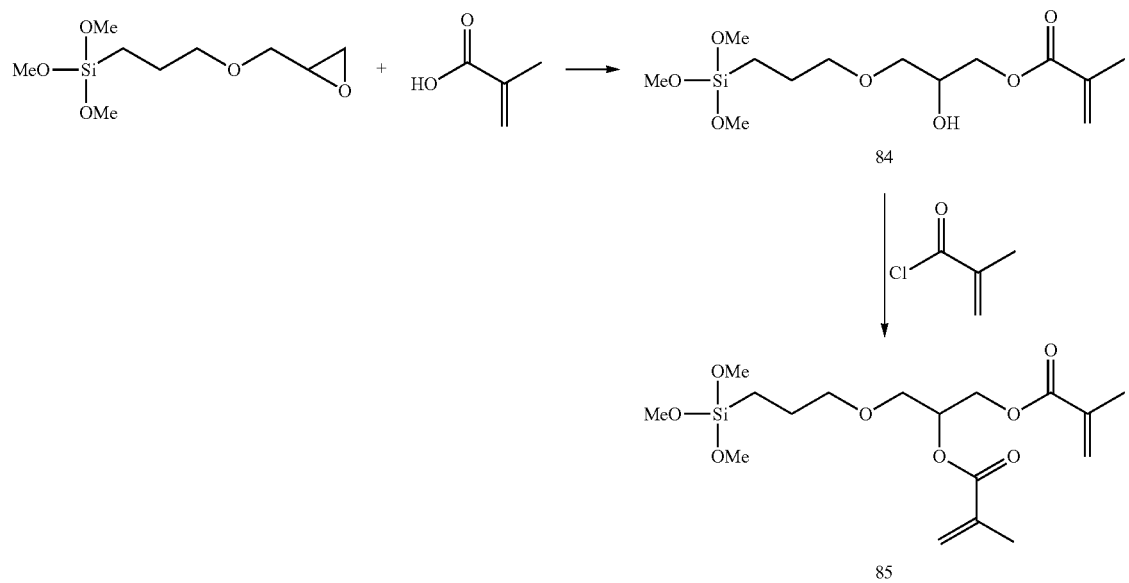

84

85

Synthesis of $(R^1O)_aR^2{}_bSi[-(CH_2)_{(n+2)}-X'-C(=O)-B'[-Z-C(=O)C(=CH_2)R^3]_f]_c$ In a two-stage synthesis initially a carboxyl (meth)acryl compound is reacted with a OH or SH functionalized terminal vinyl compound. Suitable commercially carboxyl (meth)acryl compounds are shown in Table 15. Suitable OH or SH functionalized terminal vinyl compounds are listed in Table 16. Preferred is the use of allyl alcohol or allyl mercaptan.

$[R^3C(=CH_2)C(=O)-Z-]_fB'-COOH+H_2C=CH(CH_2)_n-X'H \rightarrow [R^3C(=CH_2)C(=O)-Z-]_fB'-C(=O)-X'-(CH_2)_nCH=CH_2$

TABLE 15

| | [R³—C(=CH₂)C(=O)—Z—]fB'—COOH | | | |
|---|---|---|---|---|
| CAS-Nr. | R³ | Z | f | —B'— |
| 141681-03-0 | H | O | 1 | —(CH₂)₃— |
| 59178-90-4 | Me | NH | 1 | —(CH₂)₂— |
| 16753-07-4 | H | NH | 1 | —(CH₂)₂— |
| 59178-91-5 | Me | NH | 1 | —(CH₂)₃— |
| 59178-91-5 | H | NH | 1 | —(CH₂)₃— |
| 20882-04-6 | Me | O | 1 | —(CH₂)₂OC(=O)—(CH₂)₂— |
| 112241-32-4 | Me | O | 1 | —(CH₂)₃OC(=O)—(CH₂)₂— |
| 51252-88-1 | Me | O | 1 | 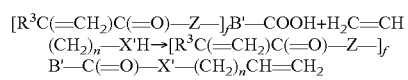 |
| 27697-00-3 | Me | O | 1 | 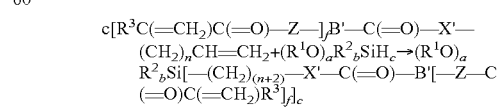 |

TABLE 15-continued

| | [R³—C(=CH₂)C(=O)—Z—]fB'—COOH | | | |
|---|---|---|---|---|
| CAS-Nr. | R³ | Z | f | —B'— |
| 65859-45-2 | Me | O | 1 | (structure) |

TABLE 16

| | H₂C=CH(CH₂)ₙ—X'H | |
|---|---|---|
| CAS-Nr. | n | X'H |
| 107-18-6 | 1 | OH |
| 627-27-0 | 2 | OH |
| 821-09-0 | 3 | OH |
| 821-41-0 | 4 | OH |
| 4117-10-6 | 5 | OH |
| 13175-44-5 | 6 | OH |
| 870-23-5 | 1 | SH |
| 5954-70-1 | 2 | SH |
| 17651-37-5 | 3 | SH |
| 17651-39-7 | 4 | SH |
| 173777-16-7 | 5 | SH |
| 178561-30-3 | 9 | SH |

In the second synthesis stage the obtained vinyl compound is reacted with the hydrosilane $(R^1O)_aR^2{}_bSiH_c$ by platinum catalysis. Commercially available hydrosilanes are shown above in Table 7.

$c[R^3C(=CH_2)C(=O)-Z-]_fB'-C(=O)-X'-(CH_2)_nCH=CH_2+(R^1O)_aR^2{}_bSiH_c \rightarrow (R^1O)_aR^2{}_bSi[-(CH_2)_{(n+2)}-X'-C(=O)-B'[-Z-C(=O)C(=CH_2)R^3]_f]_c$ Some syntheses of the silanes $(R^1O)_aR^2{}_bSi[-(CH_2)_{(n+2)}-X'-C(=O)-B'[-Z-C(=O)C(=CH_2)R^3]_f]_c$ are shown by way of example hereinafter.

Initially the vinyl compound (86) is obtained by the reaction of 3-[(2-methyl-1-oxo-2-propen-1-yl)amino]propanoic acid with propen-1-ol. The silane (87) is finally obtained by further platinum catalyzed reaction with triethoxysilane.

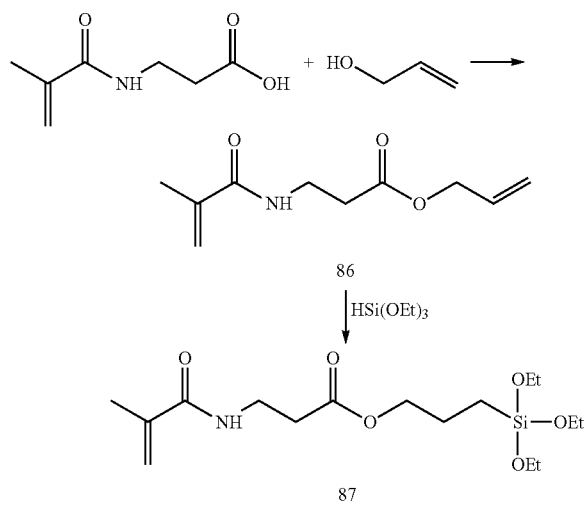

Initially the vinyl compound (88) is obtained by the reaction of 4-[(2-methyl-1-oxo-2-propen-1-yl)amino]butanoic acid with propen-1-ol. The silane (89) is finally obtained by further platinum catalyzed reaction with triethoxysilane.

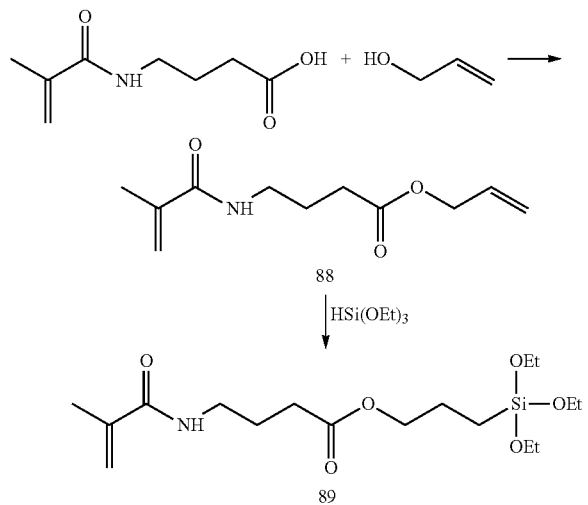

Initially the vinyl compound (90) is obtained by the reaction of 3-[(2-methyl-1-oxo-2-propen-1-yl)amino]propanoic acid with 2-propen-1-thiol. The silane (91) is finally obtained by further platinum catalyzed reaction with triethoxysilane.

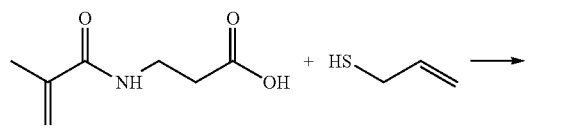

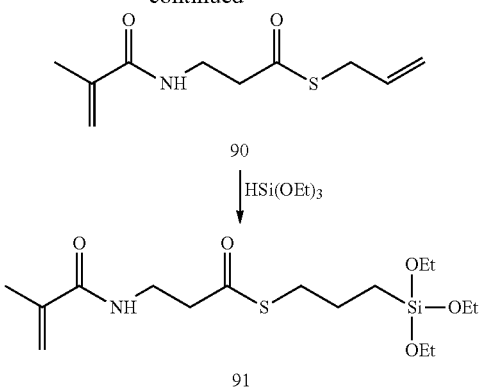

Initially the vinyl compound (92) is obtained by the reaction of 4-[(2-methyl-1-oxo-2-propen-1-yl)amino]butanoic acid with 2-propen-1-thiol. The silane (93) is finally obtained by further platinum catalyzed reaction with methyldimethoxysilane.

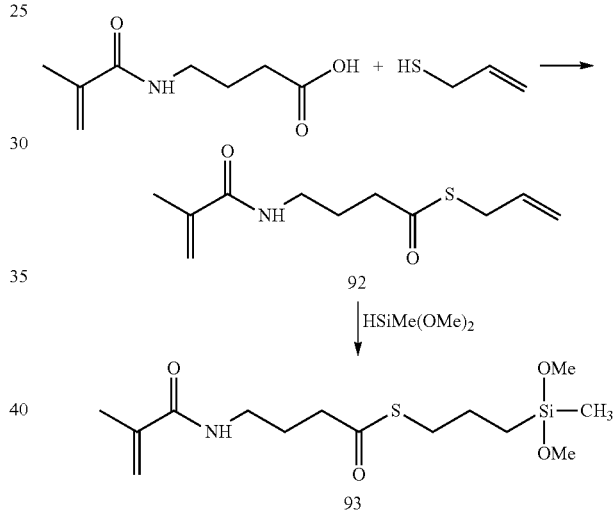

Initially the vinyl compound (94) is obtained by the reaction of mono-2-(methacryloyloxy)ethyl succinate with 2-propen-1-ol. The silane (95) is finally obtained by further platinum catalyzed reaction with triethoxysilane.

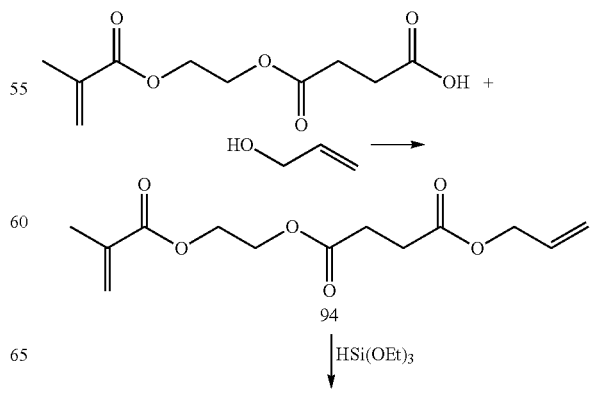

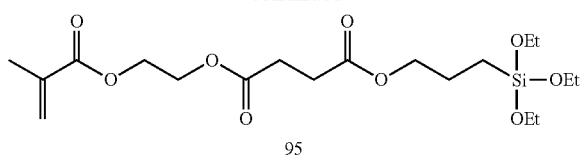
95

Initially the vinyl compound (94 see above) is obtained by the reaction of mono-2-(methacryloyloxy)ethyl succinate with 2-propen-1-ol. The silane (96) is finally obtained by further platinum catalyzed reaction with methyldimethoxysilane.

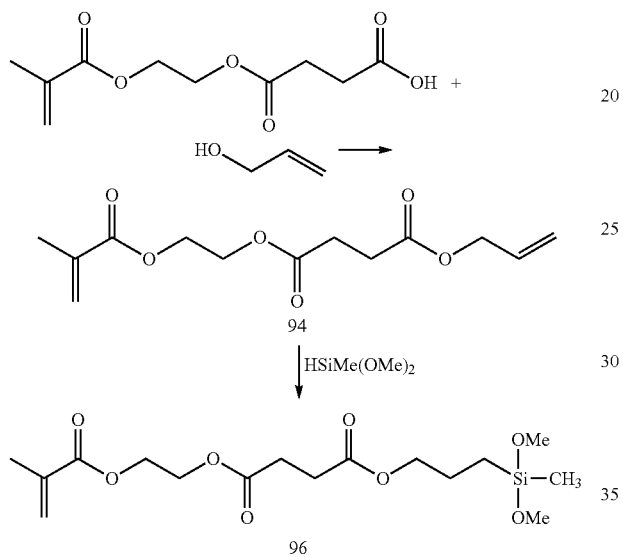

Initially the vinyl compound (97) is obtained by the reaction of mono-2-(methacryloyloxy)ethyl succinate with 2-propen-1-thiol. The silane (98) is finally obtained by further platinum catalyzed reaction with triethoxysilane.

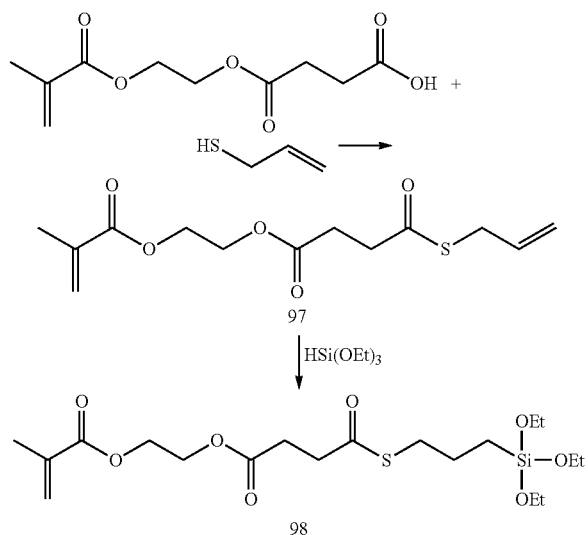

Silane $(R^1O)_aR^2{}_bSiAr_c$ (a3)

Silane (a3) corresponds to the formula $(R^1O)_aR^2{}_bSiAr_c$ wherein
$R^1$=H or C1- to C4-alkyl,
$R^2$=C1- to C4-alkyl,
Ar=aryl wherein different Ar groups can be the same or different,
a=2 or 3,
b=0 or 1,
c=1 or 2, and
a+b+c=4.

In a preferred embodiment, the radical $R^1$ is selected from the group consisting of H, methyl and ethyl.

In a further preferred embodiment, the radical Ar is a phenyl group, that may also be substituted.

Several suitable aromatic silanes are commercially available. In Table 17, silanes $(R^1O)_aR^2{}_bSiAr$ with one aryl radical and in Table 18 silanes $(R^1O)_2SiAr_2$ with two aryl radicals are listed.

TABLE 17

| | $(R^1O)_aR^2{}_bSiAr$ | | | | |
|---|---|---|---|---|---|
| CAS-Nr. | $R^1$ | $R^2$ | a | b | Ar |
| 2996-92-1 | Me | — | 3 | 0 | Ph |
| 780-69-8 | Et | — | 3 | 0 | Ph |
| 17903-00-3 | $^i$Pr | — | 3 | 0 | Ph |
| 10581-02-9 | n-Bu | — | 3 | 0 | Ph |
| 3027-21-2 | Me | Me | 2 | 1 | Ph |
| 775-56-4 | Et | Me | 2 | 1 | Ph |
| 223668-64-2 | Me | — | 3 | 0 | pentafluorophenyl |
| 17043-05-9 | Me | — | 3 | 0 | 4-bromophenyl |
| 35692-33-2 | Me | — | 3 | 0 | 2-naphthyl |
| 17995-18-5 | Et | — | 3 | 0 | 2-naphthyl |
| 17938-34-0 | Et | Me | 2 | 1 | 2-naphthyl |
| 18052-76-1 | Me | — | 3 | 0 | 1-naphthyl |

TABLE 17-continued
| | (R¹O)ₐR²_b SiAr | | | | |
|---|---|---|---|---|---|
| CAS-Nr. | R¹ | R² | a | b | Ar |
| 17938-06-6 | Et | — | 3 | 0 | 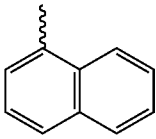 |
| 17938-33-9 | Et | Me | 2 | 1 | 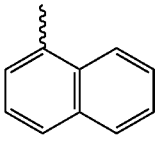 |
| 912576-47-7 | Et | — | 3 | 0 | 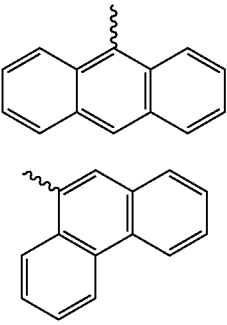 |
| 21591-53-7 | Et | — | 3 | 0 | 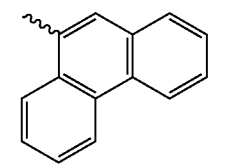 |
| 212609-47-7 | Et | — | 3 | 0 | 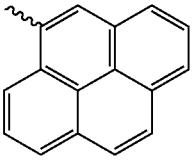 |
| 21591-51-5 | Et | — | 3 | 0 | 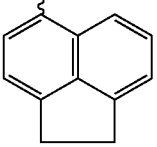 |
| 135251-76-2 | Me | — | 3 | 0 | 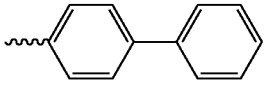 |
| 18056-97-8 | Et | — | 3 | 0 | 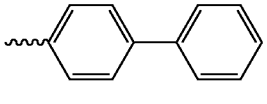 |
| 91309-02-3 | Me | Me | 2 | 1 | 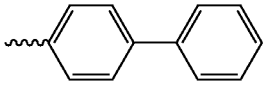 |
TABLE 18
| | (R¹O)ₐSiAr¹Ar² | | |
|---|---|---|---|
| CAS-Nr. | R¹ a | Ar¹ | Ar² |
| 6843-66-9 | Me 2 | Ph | Ph |
| 2553-19-7 | Et 2 | Ph | Ph |
| 92779-72-1 | Me 2 |  | 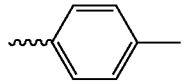 |
| 52897-51-5 | Et 2 | 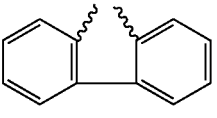 | |
| 223668-68-6 | Me 2 | 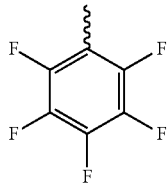 | 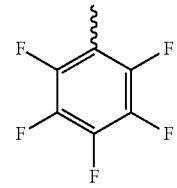 |
| 36147-17-8 | Me 2 | Ph | 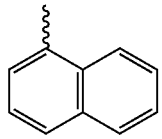 |

TABLE 18-continued

| | | | (R¹O)ₐSiAr¹Ar² | |
|---|---|---|---|---|
| CAS-Nr. | R¹ | a | Ar¹ | Ar² |
| 21591-48-0 | Me | 2 | 1-naphthyl | 1-naphthyl |
| 144677-99-6 | Me | 2 | 4-biphenyl | 4-biphenyl |

Furthermore silanes $(R^1O)_aR^2{}_bSiAr_c$ can also be produced by catalyzed reaction of aryl chlorosilanes or aryl silanes with alcohols.

By way of example here is shown the synthesis of trimethoxyphenylsilane (99) by reacting trichlorophenylsilane or phenylsilane with methanol.

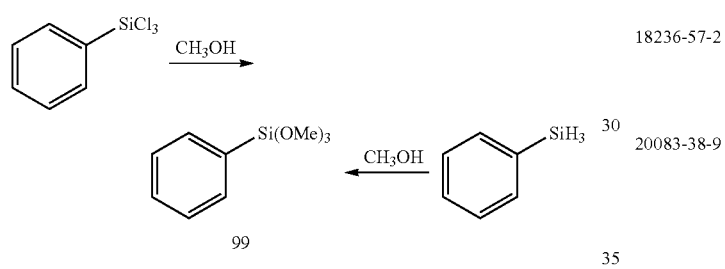

WO 2012/091154 A1 discloses the Lewis acid catalyzed synthesis of aryl alkoxysilanes by the reaction of aryl chlorosilanes with ethers. The catalyst is for example bismuth(III)chloride.

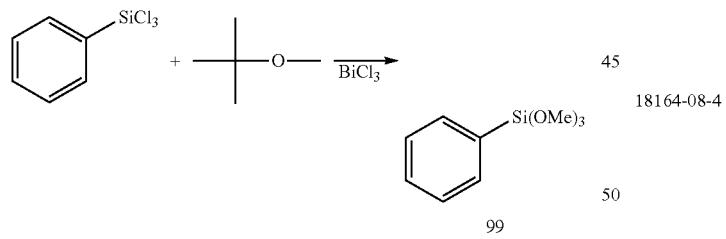

Suitable commercially available chlorosilanes are shown in Tables 19 and 20.

TABLE 19

| | | Cl_aR²_bSiAr | | |
|---|---|---|---|---|
| CAS-Nr. | R² | a | b | Ar |
| 98-13-5 | — | 3 | 0 | Ph |
| 149-74-6 | Me | 2 | 1 | Ph |
| 1125-27-5 | Et | 2 | 1 | Ph |
| 790234-74-1 | ⁱPr | 2 | 1 | Ph |
| 17887-41-1 | ᵗBu | 2 | 1 | Ph |

TABLE 19-continued

| | | Cl_aR²_bSiAr | | |
|---|---|---|---|---|
| CAS-Nr. | R² | a | b | Ar |
| 701-35-9 | — | 3 | 0 | 4-tolyl |
| 18236-57-2 | Me | 2 | 1 | 4-tolyl |
| 20083-38-9 | — | 3 | 0 | pentafluorophenyl |
| 21980-43-8 | Me | 2 | 1 | pentafluorophenyl |
| 18164-08-4 | — | 3 | 0 | 4-bromophenyl |
| 18141-19-0 | Me | 2 | 1 | 4-bromophenyl |
| 1521-07-9 | — | 3 | 0 | 2-naphthyl |

TABLE 19-continued

| CAS-Nr. | R² | a | b | Ar |
|---|---|---|---|---|
| 17998-61-7 | Me | 2 | 1 | 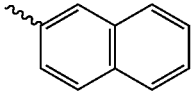 |
| 17995-31-2 | Et | 2 | 1 | 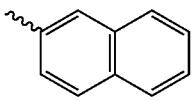 |
| 1521-08-0 | — | 3 | 0 | 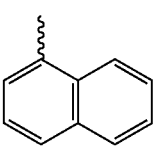 |
| 17998-62-8 | Me | 2 | 1 | 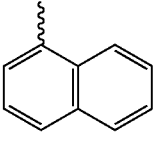 |
| 17950-78-6 | Et | 2 | 1 | 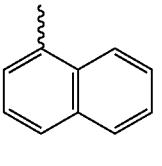 |
| 1187327-65-6 | — | 3 | 0 | 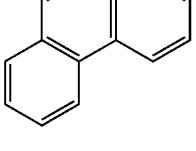 |
| 136687-79-1 | — | 3 | 0 | 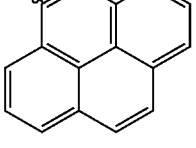 |
| 18030-61-0 | — | 3 | 0 | 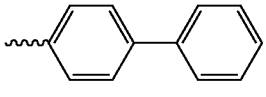 |
| 51840-45-0 | Me | 2 | 1 | 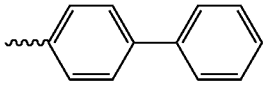 |
| 18557-48-7 | Et | 2 | 1 | 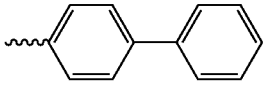 |

TABLE 20

Cl$_a$SiAr¹Ar²

| CAS-Nr. | a | Ar¹ | Ar² |
|---|---|---|---|
| 80-10-4 | 2 | Ph | Ph |
| 13788-41-5 | 2 | Ph |  |
| 18414-38-5 | 2 | 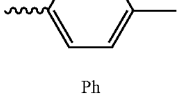 | 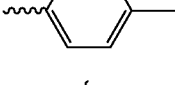 |
| 20160-53-6 | 2 | Ph | 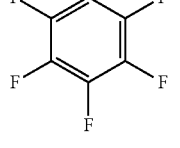 |
| 20160-45-6 | 2 | 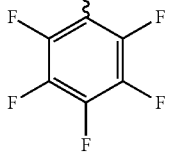 | 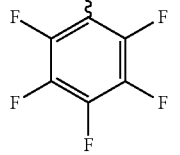 |
| 18030-58-5 | 2 | 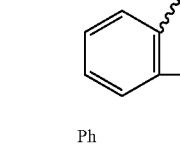 | |
| 7751-39-5 | 2 | Ph | 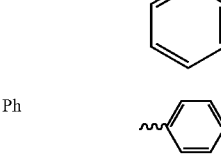 |
| 18557-48-7 | 2 | Ph | 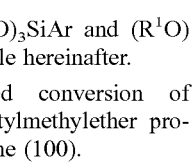 |

Some syntheses of the silanes (R¹O)$_3$SiAr and (R¹O)$_2$SiAr¹Ar² are shown by way of example hereinafter.

The bismuth(III)chloride catalyzed conversion of 2-(trichlorosilyl)naphthalene in tert-butylmethylether provides the 2-(trimethoxysilyl) naphthalene (100).

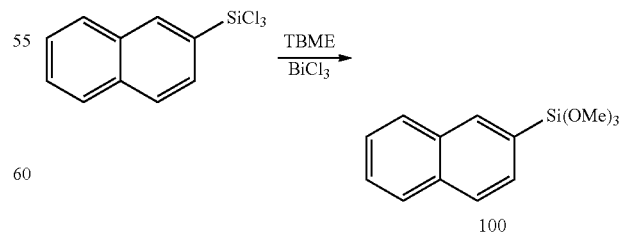

The bismuth(III)chloride catalyzed conversion of 1-(trichlorosilyl)naphthalene in tert-butylmethylether provides the 1-(trimethoxysilyl)naphthalene(101).

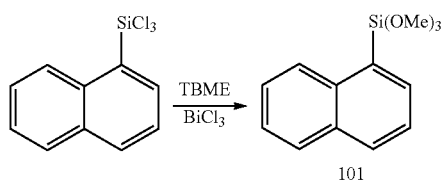

101

The bismuth(III)chloride catalyzed conversion of 4-(trichlorosilyl)-1,1'-biphenyl in tert-butylmethylether provides the 4-(trimethoxysilyl)-1,1'-biphenyl (102).

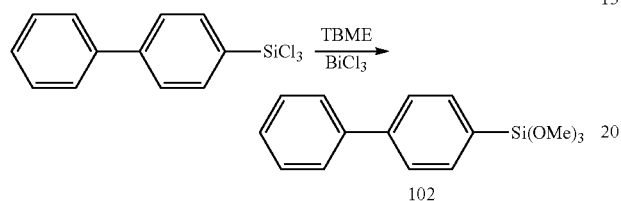

102

The bismuth(III)chloride catalyzed conversion of 9,9-dichloro-9H,9-silafluorene in tert-butylmethylether provides the 9,9-dimethoxy-9H,9-silafluorene (103).

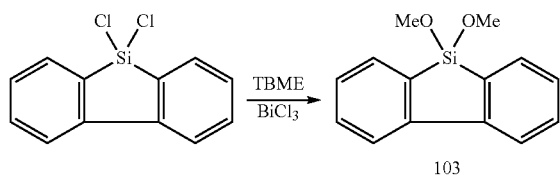

103

The bismuth(III)chloride catalyzed conversion of 4-(dichlorophenylsilyl)-1,1'-biphenyl in tert-butylmethylether provides the 4-(dimethoxyphenylsilyl)-1,1'-biphenyl (104).

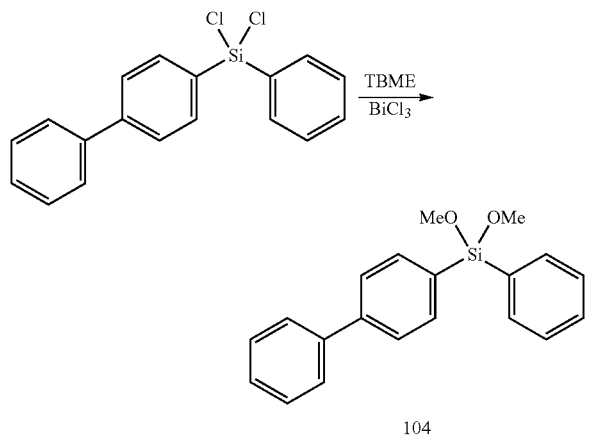

104

JP 2016-34912 A discloses the synthesis of $(R^1O)_a R^2{}_b SiAr_c$ by reaction of tetraalkoxysilanes with diarylmanganese compounds. By suitable selection of the reaction conditions, either predominantly the monoarylsilanes $(R^1O)_3 SiAr$ or the diarylsilanes $(R^1O)_2 SiAr_2$ can be obtained.

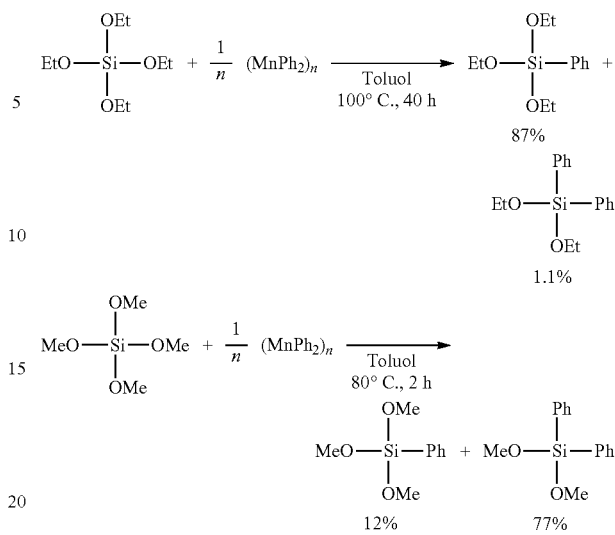

In particular aryl radicals, comprising one or more halogene atoms are preferred. By such halogene substituted aryl radicals the refractive index $n_A$ of the polysiloxanes can be adjusted more precisely in the desired range.

Component (B)—Organic and/or Inorganic Filler.

An inventive polymerizable dental composition contains in addition to component (A) also component (B), a proportion of filler particles of 0.3 to 92% by weight, based on the total mass of the polymerizable dental composition of the invention.

Depending on the indication of the dental product, the amount of the filler fraction is specified. Thus, preferably high amounts of filler are used for packable filling composites, for dental compositions for the production of inlays, onlays or overlays and for compositions for the production of dental block materials. Usually these compositions have a filler amount of 80% by weight to 92% by weight based on the total composition. Flowable dental composites, luting composites, core buildup materials, crown and bridge materials generally comprise a medium filler content in the range of 50 to 80% by weight based on the total composition, while dental lacquers, dental sealing materials or dental adhesives contain fillers in the range of 0.3 to 50% by weight based on the total composition.

The above indicated filler ranges should only be considered as reference values, because there are also special polymerizable compositions, using for example larger amounts of nanoscale fillers (20% by weight), so that they are applied as fissure sealants with a filler amount of 70% by weight based on the total composition. These fissure sealant materials can also be applied as flowable composite materials (flow materials).

Organic filler particles comprise or consist of, for example, one or more compounds selected from the group consisting of polyvinyl acetate and copolymers of polyvinyl acetate with one or more polymerizable compounds, polystyrene, polyethylene, polypropylene, waxes such as polyethylene wax, polybutylene, polybutadiene, copolymers of butadiene and styrene, polyacrylonitrile, resins such as rosin or hydrocarbon resins, poly(meth)acrylate esters, i.e. reaction products of poly(meth)acrylic acid with linear or branched aliphatic, aromatic or cycloaliphatic alcohols such as methanol, ethanol, propanol, isopropanol, the isomeric butanols and higher homologs of the alcohols mentioned having up to 22 carbon atoms, cyclohexanol, benzyl alcohol and the like, polydialkyl maleates such as dibutyl maleate and copolymers thereof, and polymers containing silyl groups, such as polyvinylsilanes or copolymers of vinylsilane with one or more of the monomers mentioned. The organic fillers can be used alone or as mixtures.

The inorganic fillers can likewise be used alone or as mixtures. To optimize the product properties, the inorganic fillers can be introduced into the formulations in different particle sizes. The fillers may have a unimodal or polymodal distribution, for example a bimodal distribution.

As inorganic fillers, it is possible to use compact glasses and different silicas in various sizes and states (monodisperse, polydisperse).

Suitable inorganic components are, for example, amorphous materials based on mixed oxides composed of $SiO_2$, $ZrO_2$ and/or $TiO_2$, and also fillers such as quartz glass ceramic or glass powders, barium silicate glasses, barium fluorosilicate glasses, strontium silicate glasses, strontium borosilicate, Li/Al silicate glasses, barium glasses, calcium silicates, sodium aluminosilicates, fluoroaluminosilicate glasses, oxides of aluminum or silicon, zeolites, apatite, zirconium silicates, sparingly soluble metal salts such as barium sulfate or calcium fluoride, and x-ray-opaque fillers such as ytterbium fluoride.

For better incorporation into the polymer matrix, the fillers may be organically surface-modified. One example is the surface treatment of the fillers with a silane. A particularly suitable coupling agent is methacryloyloxypropyltrimethoxysilane.

To adjust the rheology, the polymerizable dental compositions may contain different silicas, preferably fumed silicas.

Preferably, the polymerizable compositions of the invention contain nanoscale solid particles. The nanoscale solid particles are particles having an average particle size of not more than 200 nm, preferably not more than 100 nm and especially not more than 70 nm. The nanoscale inorganic solid particles are preferably those of oxides, sulfides, selenides and tellurides of metals, semimetals and mixtures thereof. Particular preference is given to nanoscale particles of $SiO_2$, $TiO_2$, $ZrO_2$, $ZnO$, $SnO_2$ and $Al_2O_3$, and mixtures thereof. The nanoscale solid particles are produced in a known manner, for example by flame pyrolysis, plasma methods, gas phase condensation, colloid techniques, precipitation methods, sol-gel methods, etc.

In a preferred embodiment, the nanoscale particles are in non-agglomerated and/or non-aggregated form, for example dispersed in a medium, preferably in monodisperse form.

In order to enable good binding of the nanoparticles into the polymer matrix of a polymerizable dental composition of the invention, the surfaces of the nanoparticles may likewise have been organically surface-modified, meaning that their surfaces have organic structural elements. Examples include the surface treatment of the fillers with a silane. A particularly suitable coupling agent here is also methacryloyloxypropyltrimethoxysilane.

In a further preferred embodiment, the nanoscale particles are thus non-agglomerated and/or non-aggregated, organically surface-modified nanoparticles having an average particle size of less than 200 nm, preferably less than 100 nm, more preferably less than 70 nm, which have in turn preferably been silanized.

Commercially available nanoscale, non-agglomerated and non-aggregated silica sols which can be used in accordance with the invention are traded, for example, under the "NALCO COLLOIDAL SILICAS" (Nalco Chemical Co.), "Ludox colloidal silica" (Grace) or "Highlink OG" (Clariant) names.

In a preferred embodiment, the filler fraction of a polymerizable dental composition of the invention comprises a mixture of a first filler (b1) in the form of non-agglomerated, non-aggregated organically surface-modified nanoparticles having an average particle size of less than 200 nm and a second filler (b2) in the form of macroscopic microparticles having an average particle size in the range from 0.4 μm to 10 μm. The combination of (b1) nanoparticles and (b2) microparticles in a polymerizable dental composition of the invention achieves complete and homogeneous filling of volume of the composite material. This reduces both the shrinkage of the polymerizable composition in the course of curing of the polymer matrix and the sensitivity of the composition of the invention to abrasion.

The proportion of organically surface-modified nanoparticles in a preferred polymerizable dental composition of the invention having an average particle size of less than 200 nm is greater than 1% by weight, preferably greater than 2% by weight and more preferably greater than 3% by weight. In in-house studies, it has been found that, in the case of a content of 1% by weight or less of non-agglomerated and/or non-aggregated organically surface-modified nanoparticles having an average particle size of less than 200 nm, the free-radically curable dental composition no longer has a sufficient abrasion resistance in each individual case. One reason for this is probably that, in the case of a content of 1% by weight or less of said nanoparticles, the regions between the microparticles having an average particle size of 0.4 μm to 10 μm are no longer filled adequately. On the other hand, it has been shown that, in the case of a content of more than 20% by weight of non-agglomerated and/or non-aggregated, organically surface-modified nanoparticles having an average particle size of less than 200 nm, processibility of the composition is no longer adequate. Because of the high solids content, its viscosity then becomes too high.

The materials for the nanoparticles for use in accordance with the invention are preferably oxides or mixed oxides and are preferably selected from the group consisting of oxides and mixed oxides of the elements silicon, titanium, yttrium, strontium, barium, zirconium, hafnium, niobium, tantalum, tungsten, bismuth, molybdenum, tin, zinc, ytterbium, lanthanum, cerium, aluminum and mixtures thereof. The preferred oxidic nanoparticles are, as explained, non-agglomerated and/or non-aggregated, and have been organically surface-treated.

Within a polymerizable dental composition of the invention, the microparticles bring about substantially homogeneous filling of volume, with the remaining cavities between the microparticles at least partly filled by the above-described nanoparticles (component (b1)). In the context of the present invention, microparticles are understood to mean particles having an average particle size of 400 nm to 10 μm. Preferably, the average particle size is less than 5 μm. It has been found that the completeness and homogeneity of the filling of volume of the polymerizable dental composition which is already achievable with the microparticles increases with decreasing microparticle size.

The microparticles of component (b2) may have a monomodal or polymodal particle size distribution, for example a bimodal particle size distribution. Microparticles having a bimodal or multimodal particle size distribution are preferable in accordance with the invention, since more complete filling of volume is achievable therewith than in the case of general use of microparticles having monomodal particle size distribution. In the presence of a bi- or multimodal particle size distribution, the particles of the fractions having the larger particle size bring about coarse filling of volume, while the particles of the fraction having the smaller particle size, as far as possible, fill the regions between the particles of the fractions having the larger particle size. The cavities still remaining are filled by nanoparticles as described above.

Most preferably, therefore, in a polymerizable dental composition of the invention, a component (b2) containing two or more fractions of microparticles, with different average particle sizes of the fractions, is used.

Preferably, component (b2) contains at least two microparticle fractions wherein the average particle sizes differ from one another by at least 0.5 µm, preferably by at least 0.7 µm. In some embodiments, the difference between the average particle sizes of the microparticle fractions is at least 1.0 µm.

The microparticles of different fractions may consist of the same material or of different materials; it is also possible for there to be two or more fractions of microparticles having average particle sizes that are approximately the same or within a particular range, in which case the materials of the particles differ between the fractions.

More preferably, a polymerizable dental composition of the invention comprises a component (b2) having one or more first microparticle fractions each having an average particle size in the range from 1 µm to 10 µm, preferably 1 µm to 5 µm, and one or more second microparticle fractions each having an average particle size in the range from >0.4 µm to <1 µm (i.e. larger than 0.4 µm but smaller than 1 µm), preferably 0.5 µm to 0.8 µm.

Preferably, the ratio of the total mass of the first microparticle fractions to the total mass of the second microparticle fractions is in the range from 1:1 to 12:1, preferably in the range from 1.5:1 to 8:1.

Preferably, the ratio of the average particle size of the or a first microparticle fraction to the average particle size of the or a second microparticle fraction of component (b2) is in the range from 1.5:1 to 10:1, preferably in the range from 2:1 to 5:1.

In a particularly preferred polymerizable dental composition of the invention, component (b2) comprises one or more first microparticle fractions each having an average particle size in the range from 1 µm to 10 µm, preferably 1 µm to 5 µm, and one or more second microparticle fractions each having an average particle size in the range from >0.4 µm to <1 µm, preferably 0.5 µm to 0.8 µm; wherein the ratio of the total mass of the first microparticle fractions to the total mass of the second microparticle fractions is in the range from 1:1 to 12:1, preferably 1.5:1 to 8:1 and/or the ratio of the average particle size of the or a first microparticle fraction to the average particle size of the or a second microparticle fraction of component (b2) is in the range from 1.5:1 to 10:1, preferably 2:1 to 5:1.

In a particularly preferred polymerizable dental composition of the invention, at least a portion of the microparticles of component (b2) is formed by organically surface-modified particles, preferably silanized particles, and/or at least a portion of the microparticles of component (b2) is formed by dental glass particles; preferably, at least a portion of the microparticles of component (b2) is formed by organically surface-modified dental glass particles, preferably silanized dental glass particles.

In these cases, component (b2) preferably features a bi- or multimodal particle size distribution, especially a bi- or multimodal particle size distribution having the preferred features described above.

As well as components (b1) and (b2), the polymerizable dental composition may comprise further fillers as component (b3) in addition to the mixture of filler particles.

For example, it is possible to use reinforcing filler materials such as glass fibers, polyamide fibers or carbon fibers. A polymerizable dental composition of the invention may also contain fine splinter or bead polymers, wherein the bead polymers may be homo- or copolymers of organically curable monomers.

In a particularly preferred embodiment, a polymerizable dental composition of the invention contains an x-ray-opaque filler. Most preferably, the composition of the invention contains nanoscale $YbF_3$ and/or $BaSO_4$.

In in-house studies, it has been found that a refractive index $n_A$ of the total amount of the polymerizable monomers (A) and (D) in the range from 1.45 to 1.55 very frequently leads to very good translucence values, since the refractive indices of the one, two, three or more than three fillers which form the total amount (B) of the fillers in the curable dental material can be matched in a comparatively simple manner to such a refractive index $n_A$. As a result of this good matching, the light used in light-induced polymerization of polymerizable monomers in the curable dental material achieves a high penetration depth and hence results in homogeneous polymerization. This leads to a high-quality cured dental material with very good mechanical properties.

If the refractive index $n_A$ is less than 1.45 or greater than 1.55, the aforementioned matching becomes more complex in many cases (especially in the case of a refractive index of less than 1.45), and the penetration depth of the light is acceptable only in a few cases, or is barely acceptable (since particularly intense light scattering is to be expected in most cases). This increases the risk that non-polymerized polymerizable monomers will be released from an (only partly) cured dental material and migrate into the oral cavity. In addition, such (partly) cured dental materials have a considerably reduced strength. Such curable dental materials then inconveniently have to be applied in very thin layers and each layer has to be cured individually, in order to minimize the aforementioned disadvantages. If the refractive index is greater than 1.45 but less than 1.48, in most cases, sufficiently good matching is achieved, so as to result in sufficiently good penetration depth of the light. Application of such a curable dental material (and the subsequent curing) can then be effected correspondingly without any great difficulty. If the refractive index is within a range from 1.48 to 1.55, very good results are regularly achieved, with the usual use of x-ray-opaque dental glasses.

Particular preference is given to a curable dental material of the invention (as described above, preferably as defined above as preferred) wherein the total amount of the particulate fillers (B) has a refractive index $n_B$ in the range from 1.50 to 1.55.

Especially preferred is a curable dental material according to the invention (as described above, preferably as defined above as preferred), wherein the amount of difference $|n_A - n_B|$ between the refractive index of the polymerizable monomers total amount ((A) and (D)) $n_A$ and the refractive index of the fillers total amount $n_B$ is smaller than 0.05, preferably smaller than 0.03, preferred smaller than 0.02 and especially preferred smaller than 0.01. Such dental materials show in particular the described high translucency and thus the good curing properties.

During the polymerization the density of the resin matrix increases due to the shrinkage. This increase of the density also leads to an increase of the refractive index during the polymerization. In contrast, the refractive index of the fillers during the polymerization does not change. This can lead to a decrease of the translucency and curing properties during the polymerization. The compositions according to the invention are characterized by a low shrinkage, so that only a small change of the density and of the refractive index during the polymerization occurs and so the translucency and the refractive index only change slightly during the polymerization being a reliable curing guaranteed.

Preferred is therefore a curable dental material (as described above, preferably as defined above as preferred) according to the invention in which the difference $n_P - n_A$ of the refractive index $n_P$ of the polymerized resin matrix (from (A) and (D)) and of the refractive index $n_A$ of the total amount of the polymerizable monomers (A) and (D) before the polymerization is smaller than 0.03 and preferably smaller than 0.02.

Qualitative and Quantitative Characterization of the Filler Particles:

The steps described hereinafter in the qualitative and quantitative characterization of the filler particles (especially of nanoscale filler particles) are well known to those skilled in the art and are described comprehensively in the literature.

Resin/Filler Separation:

In a first step, 1 g of a polymerizable dental composition of the invention (also called composite material hereinafter) is suspended in 10 mL of acetone and the resultant suspension is then centrifuged with a centrifuge at 5000 rpm for 10 min. The supernatant (called resin phase hereinafter) is decanted off into a collection bottle and the residue is slurried in 5 mL of acetone. The mixture is centrifuged again at 5000 rpm for 10 minutes and decanted, and the residue is slurried again in 5 mL of acetone. The steps of centrifuging, decanting and slurrying are repeated twice more under identical conditions. The total amount of residues separated from the resin phases is dried, and the total amount of resin phases is freed of acetone on a rotary evaporator.

After carrying out the first step, the dried total amount of residues regularly includes those filler particles having a particle size of about 400 nm or greater than 400 nm (called macroscopic filler particles hereinafter). The total amount of resin phases freed of acetone (called resin fraction hereinafter) regularly also includes, as well as polymerizable monomers, filler particles having a particle size of about 400 nm or especially less than 400 nm (called nanoscale particles hereinafter). This method therefore ensures that the dental composite material, by centrifugation, is separated completely into (i) a fraction of macroscopic filler particles, especially with regard to the dental glasses having a size in the order of magnitude of greater than 400 nm up to the high micrometer range, and (ii) a resin fraction including nanoscale particles.

The median particle size $d_{50}$ of the macroscopic filler particles for use in accordance with the invention in the filler component (b2) of a composition of the invention is determined by means of light scattering (laser diffraction), preferably with a Beckman Coulter LS 13320 particle size analyzer.

The nanoscale particles present in the resin fraction may, for example, be both non-aggregated and/or non-agglomerated particles, for example including x-ray-opaque particles, for example $YbF_3$ or $BaSO_4$, having particle sizes within a range from about 3 nm to 200 nm, and non-x-ray-opaque silicas which take the form, for example, of fumed silicas in the form of aggregates and/or agglomerates having a particle size within a range from about 150 nm to about 300 nm, or else silicas which are synthesized by the sol-gel process (or else from waterglass) and which are likewise in non-aggregated and/or non-agglomerated form and have particle sizes within a range from about 3 nm to 200 nm.

The total proportion by mass of inorganic particles in the resin fraction is determined gravimetrically by difference weighing after ashing of an appropriate resin fraction.

TEM in Combination with EELS:

In a second step, the filler particles in the resin fraction are subjected to a qualitative and quantitative characterization. For this purpose, TEM (transmission electron microscopy) is used in combination with EELS (electron energy loss spectroscopy).

By TEM, the particle sizes of the individual particles and the number thereof are determined; elemental determination of individual particles is carried out by EELS.

To perform the combined TEM/EELS characterization, in a first step, the concentration of the nanoscale particles in the resin fraction is first reduced by dilution with polymerizable resin. This very substantially rules out observation of "overlapping" of nanoscale particles in the later images. Such "overlapping" would distort the particle characterization. In-house studies have shown that the optimal particle concentration (i.e. the proportion by volume of the filler particles) for such studies is 1% by volume, based on the total mass of the diluted sample.

In a second step, bar specimens are produced by curing the diluted resin fractions obtained by dilution with polymerizable resin. These bar specimens are then used to produce several ultrathin sections of thickness 300 nm with an ultra-diamond knife (for example ULTRACUT UCT, LEICA, Wetzlar). The ultrathin sections are transferred to copper TEM grids for stabilization. This results in thin section preparations. These thin section preparations are then analyzed with 120 kV acceleration voltage in a TEM using bright field images.

A TEM analysis of the above-described thin section preparations allows distinction of non-aggregated and non-agglomerated nanoscale particles from aggregated and/or agglomerated particles (e.g. silicas, for example Aerosils) (for identification of the chemical composition see the details which follow).

If high-resolution images are to be examined, ultrathin sections having layer thicknesses of less than 100 nm can be produced and examined.

In a third step, the filler particles in the ultrathin sections or thin section preparations are chemically characterized by means of EELS point analyses, such that the chemical composition of individual particles becomes known (for determination of the surface modification of particles see the points below).

The volume- or weight-based proportions of particle fractions (including a plurality thereof if appropriate) are determined in a fourth step from a TEM image as follows: the image section from a TEM image viewed under a microscope is an area having edge lengths a and b which can be determined by means of the legend. Multiplying by the thickness c of the ultrathin section gives a total volume $V_{total}$ for the area under consideration in the TEM. This total volume $V_{total}$ is the sum total of the resin volume $V_{resin}$ and the volume of all the particles $V_{particles}$ within this volume (the volume of all the particles may include several groups of particles, for example sorted by various criteria, for example size). The following equation holds:

$$V_{total} = a*b*c = V_{resin} + V_{particles}.$$

The volume of individual particles (and hence the volume of all the particles in the volume under consideration) can be obtained by calculation via the sphere volume of the individual particles. For this purpose, in the TEM image, the diameter or radius of an appropriate particle is determined. The sphere volume calculated therefrom, multiplied by the density of the corresponding material of which the particle consists (material identifiable by means of EELS), gives the mass of the particle. The resin volume, obtainable from the total volume minus the particle volume, multiplied by the resin density, gives the resin mass.

The resin density is obtained very substantially from the density of the resin used for dilution and, if appropriate, the density of the diluted resin fraction (the latter can possibly be neglected in the calculation of the resin density if the proportion of the diluted resin is negligible). The proportion of the particles (or a group of particles) in percent by weight is calculated from $m_p*100/(m_{particles}+m_{resin})$ where $m_p$ is the mass of the particle fraction under consideration in the volume under consideration, $m_{particles}$ is the mass of all the particles in the volume in question and $m_{resin}$ is the mass of the resin in the volume under consideration. In the final calculation of the proportion by weight of the particle fraction under consideration, the dilution factor is taken into account appropriately.

Determination of Organic Surface Modifications:

Preliminary Assessment:

Many known x-ray-opaque filler materials (for example ytterbium fluoride or barium sulfate) have the disadvantage that they can be incorporated only with difficulty into the matrix (resin matrix) composed of polymerizable monomers (called the organic resin phase) because they do not enter into sufficient chemical bonds (binding options) with the hydrophobic groups of the medium. Vitreous fillers can be incorporated in an excellent manner into the resin matrix of dental composite materials, for example, with the aid of silanization via Si—OH groups. In the case of ytterbium fluoride and barium sulfate, no such groups are present on the surfaces; they are therefore not silanizable and lead to inadequate physical and chemical resistance in a cured dental material (see WO 2005/011621 A1, bottom of page 2).

The x-ray-opaque nanoscale particles used in a curable dental material of the invention therefore will not have any silanes on their surfaces. Instead, the linking is effected via nitrogen, oxygen, sulfur and/or phosphorus atoms (again see WO 2005/011621 A1 and our remarks further up in the text).

Removal of Polymerizable Monomers from Nanoscale Particles:

"Cross-Flow" Method:

The removal of polymerizable monomers from nanoscale particles is carried out, for example, in a "cross-flow" method known to those skilled in the art by means of ultrafiltration membranes.

In this method, a resin fraction comprising nanoscale particles, polymerizable monomers and optionally a suitable diluent is pumped from a vessel by means of a pump into a circuit composed of particular membranes, and the polymerizable monomers pass through the pores of the membranes and are separated as filtrate, while the nanoscale particles remain within the circuit (and hence within the vessel).

An example of a suitable system for this separating step is the "Vivaflow 50" system from "Sartorius Stedim Biotech GmbH, Gottingen". The pump drive (7554-95) and pump head come from the "Masterflex L/S" series from "Cole-Parmer Instrument Co.", Illinois, USA. The operation of the pump is set to 2.5 bar during the filtration. Two separation membranes of the "50,000 MWCO (PES)" type are connected in series. The MWCO (molecular weight cutoff) defines the separation limit here, i.e. the size of the molecules which can still pass efficiently through the membrane. This value is reported in daltons. The fractions obtained are subsequently analyzed as described below.

Sedimentation Field-Flow Fractionation (SF3):

Even better than the "cross-flow" method is the conduction of a sedimentation field-flow fractionation (SF3). This can especially separate different particle fractions from one another and additionally from the resin fraction. It is a prerequisite here that the different particle fractions differ sufficiently from one another in terms of size and/or density.

Corresponding equipment containing a separation column necessary for the purpose is obtainable from Postnova Analytics GmbH, Landsberg. The module containing the separation column is identified as CF2000 Centrifugal FFF and is supplemented by the further modules PN7140 (Eluent Organizer), PN1130 (Isocratic Pump), PN5300 (Autosampler), PN3621 MALS (21-Multi-Angle Light Scattering Detector) and PN8050 (Fraction Collector). In this combination, the Centrifugal FFF system allows not just the analytical but also the preparative separation of particle fractions. The fractions obtained are subsequently analyzed as described below.

Characterization of the Surface Modification:

A sample which has been produced as above and then freed of solvents, containing nanoscale particles in the form of a powder, is subsequently examined by means of spectroscopic methods (for example by means of 1H NMR, 13C NMR, 15N NMR, 29Si NMR and 31P NMR, and also IR).

Signals which cannot be attributed to a silane, for example the gamma-methacryloyloxypropylsilyl radical, are attributed to organic surface modifications not based on silanes, for example surface modifications by means of organic compounds on surfaces of ytterbium fluoride or barium sulfate particles.

The proportions of organically surface-modified particles and/or non-organically surface-modified particles can also be determined regularly by evaluation of the intensities of corresponding vibration bands in the IR spectrum. For this purpose, reference vibration bands (reference curves) of organically surface-modified or non-organically surface-modified particles with the corresponding chemical compositions are employed.

Characterization by Means of Image Analysis and Raman Spectroscopy:

The person skilled in the art is aware of additional methods and coupled methods which allow qualitative and quantitative characterization of the filler particles. In this respect, reference is made, for example, to the article "Chemische Identität einzelner Partikel" [Chemical Identity of Individual Particles] by Deborah Huck-Jones and Renate Hessemann in "Nachrichten aus der Chemie", Volume 62, September 2014, pages 886 and 887. The combination of image analysis and Raman spectroscopy disclosed therein is regularly also suitable for characterization of the filler particles in the context of the present invention. This is especially true of samples which are obtained by the resin/filler separation described above. An example of a suitable image analysis is again the TEM analysis described in the text above.

Component (C)—Initiators and/or Catalysts and/or Activator for the Polymerization A polymerizable dental composition of the invention is preferably free-radically light-curable and/or free-radically chemical curable or cationically curable.

Preference is given to a polymerizable dental composition of the invention, wherein component (C) comprises or consists of one or more light-curing initiators and/or one or more initiators for chemical or cationic polymerization.

Preferred polymerizable dental compositions of the invention are light-curable (photocurable) and comprise light-curing initiators. Examples of a light-curing initiator include substances having only photosensitizing action and combinations of sensitizer and accelerator.

Examples of photosensitizers are alpha-diketones, benzoin alkyl ethers, thioxanthones, benzophenones, acylphosphine oxides, acylgermanium compounds, acetophenones, ketals, titanocenes, sensitizing dyes, etc. The sensitizers can be employed alone or in combination. Specific substance examples from different classes can be found, for example, in DE 10 2006 019 092 A1, or in DE 39 41 629 C2.

Examples of accelerators which are used together with the sensitizers are tertiary amines, secondary amines, barbituric acids, tin compounds, aldehydes and sulfur compounds. Specific substance examples from different classes can be found, for example, in DE 10 2006 019 092 A1 or in DE 39 41 629 C2.

Further suitable initiators and initiator combinations are described in DE 601 16 142 T2.

The photoinitiators usable in the context of the present invention are characterized by that they can cause the curing of a polymerizable dental composition of the invention by absorbing light in the wavelength range from 300 nm to 700 nm, preferably from 350 nm to 600 nm and more preferably from 380 nm to 500 nm, optionally in combination with one or more coinitiators.

The absorption maximum of camphorquinone (CQ) is about 470 nm and is therefore within the blue light range. Camphorquinone (CQ) is one of the $Pl_2$ initiators and is regularly used together with a coinitiator.

Preferably, a composite material of the invention contains the combination of an alpha-diketone and an aromatic tertiary amine, preference being given to the combination of camphorquinone (CQ) and ethyl p-N,N-dimethylaminobenzoate (DABE).

Likewise preferable is the further combination of the "alpha-diketone/aromatic tertiary amine" system with a phosphine oxide, especially with bis(2,4,6-trimethylbenzoyl)phenylphosphine oxide and/or 2,4,6-trimethylbenzoyldiphenyl-phosphine oxide. With regard to the structures of suitable phosphine oxides for use in a free-radically curable dental composition of the invention, reference is made to publications DE 38 01 511 C2, DE 10 2006 050 153 A1, EP 0 184 095 B1, DE 42 31 579 C2, EP 0 366 977 B1, U.S. Pat. No. 7,081,485 B2, DE 32 36 026 A1, US 2007/0027229 A1, EP 0 262 629 B1, EP 0 073 413, U.S. Pat. No. 7,148,382 B2, U.S. Pat. No. 5,761,169, DE 197 08 294 A1, EP 0 057 474, EP 0 047 902 A, EP 0 007 508, DE 600 29 481 T2, EP 0 980 682 B1, EP 0 948 955 B1, EP 1 236 459 B1 and EP 0 173 567 A2.

The phosphine oxides specified in these publications are suitable especially alone or in combination with the "alpha-diketone/amine" system as photo-polymerization initiator system in a polymerizable dental composition of the invention.

EP 1 905 415 A1 describes polymerizable dental compositions comprising acylgermanium compounds as initiators, which are also suitable for the polymerizable dental composition of the invention.

Alternatively, it is also possible to use borate salts, as described, for example, in U.S. Pat. Nos. 4,772,530, 4,954,414, 4,874,450, 5,055,372 and 5,057,393, as photoinitiators.

Further suitable photoinitiators are described in J.-P. Fouassier, Photoinitiation, Photopolymerization and Photocuring, Hanser Publishers, Munich, Vienna, New York 1995, and in J. F. Rabek (ed.), Radiation Curing in Polymer Science and Technology, Vol. II, Elsevier Applied Science, London, New York 1993.

The person skilled in the art is aware of various initiators for chemical curing. In this regard, reference is made by way of example to EP 1 720 506. Initiators for chemical curing are also described in the publications DE 10 2006 019 092 already mentioned above and in DE 39 41 629.

Preferred initiators for chemical curing are benzoyl peroxide, lauroyl peroxide, especially dibenzoyl peroxide, in combination with amines such as N,N-dimethyl-p-toluidine, N,N-dihydroxyethyl-p-toluidine, and structurally related amines.

The peroxides and the amines are divided between two different components of the dental material. When the amine-containing component (called the base paste) is mixed with the peroxide-containing component (called the initiator or catalyst paste), the reaction of amine and peroxide (redox reaction) initiates the polymerization.

Besides peroxides and amines, hydroperoxides can also be used in combination with thioureas.

Dual-curing systems comprise a combination of photoinitiators and initiators for chemical curing.

For example, the base paste may additionally comprise a photoinitiator, such that the base paste can be used either solely as a light-curing dental composition or, together with the initiator paste, as a light- and self-curing dental composition.

As well as the oxidatively active organic peroxide compounds, the redox systems used may also be barbituric acids or barbituric acid derivatives and malonylsulfamides.

Among the barbituric acid systems, the "Bredereck systems" are of high importance. Examples of suitable "Bredereck systems" and references to the corresponding patent literature can be found in EP 1 839 640 and in DE 14 95 520, WO 02/092021 or in WO 02/092023.

Rather than the barbituric acids, it is also possible to use salts thereof. Examples of these can be found in the following documents: EP 1 872 767, EP 2 070 506, EP 1 881 010, DE 10 2007 050 763, U.S. Pat. No. 6,288,138, DE 11 2006 001 049, U.S. Pat. No. 7,214,726 and EP 2 070 935.

Suitable malonylsulfamides are described in EP 0 059 451. Preferred compounds in this context are 2,6-dimethyl-4-isobutylmalonylsulfamide, 2,6-diisobutyl-4-propylmalonylsulfamide, 2,6-dibutyl-4-propylmalonylsulfamide, 2,6-dimethyl-4-ethylmalonylsulfamide and 2,6-dioctyl-4-isobutylmalonylsulfamide.

In addition, it is possible to use sulfur compounds in the +2 or +4 oxidation state, such as sodium benzenesulfinate or sodium para-toluenesulfinate.

To accelerate the curing, the polymerization can be performed in the presence of activators in form of heavy metal compounds such as Ce, Fe, Cu, Mn, Co, Sn or Zn, particular preference being given to copper compounds. The heavy metal compounds are preferably used in the form of soluble organic compounds. Preferred copper compounds here are copper benzoate, copper acetate, copper ethylhexanoate, copper di(methacrylate), copper acetylacetonate and copper naphthenate.

The cationic polymerization can be either photoinduced or thermal. Preferably the polymerization is photoinduced, because in this application form a higher degree of crosslinking is reached, since the thermal polymerization leads to a considerable number of side reactions. Further preferred is a cationic ring opening polymerization of epoxides. Here the epoxide containing monomer reacts with the protonic acid formed from the decay of a photoinitiator to an open-chain intermediate, which as a reactive cation attacks another epoxide, opens it and continues the polymerization. The driving force of the ring-opening polymerization is the gain of ring strain energy, which is further increased in the bifunctional monomers used here due to the greater ring distortion. Cationic photoinitiators are for example ionic iodonium or sulfonium derivatives. Examples for commercially available cationic photoinitiators are (4-phenylthiophenyl)diphenylsulfonium triflate, [4(2-hydroxytetradecyl)oxy]phenyliodonium hexafluoroantimonate or p-octyloxyphenylphenyliodonium hexafluoroantimonate. By irradiating, for example, an onium salt, the onium-benzene bond is homolytically cleaved to form a phenyl radical and a radical cation, the latter reacting with R—H to form a radical, the onium-benzene and an acid. The mechanisms for other phenacyl-based photoinitiation systems are similar.

A preferred system for cationic crosslinking comprises three components: Camphorquinone, which is also used for the classical free-radical polymerization of dental materials, as light absorbing agent, an electron donor as an amine, for example the ethyl-p-N,N-dimethylaminobenzoate (DABE) mentioned above, which is also used for the classical free-radical polymerization of dental materials, and additionally a iodonium salt. Here the camphorquinone is stimulated and reacts with the amine, that converts the iodonium salt into an acidic cation in a redox process. This starts the ring-opening process of the oxiranes.

In the patent literature many initiator systems for the cationic ring-opening polymerization, especially also for the use in dental composite materials are described. Suitable systems for the dental composite materials according to the invention are in the publications EP 2 133 064 A1, entitled "Initiator system containing a diarylalkylamine derivate, hardenable composition and use thereof", EP 0 897 710 A2, entitled "Light-initiated cationic curable compositions and their use", WO 2005/051332 A1, entitled "Photoinitiator systems with anthracene-based electron donors for curing cationically polymerizable resins", U.S. Pat. No. 9,770,528 B2, entitled "Biomaterial compositions", and also the disclosure document DE 196 48 283 A1, entitled "Polymerisierbare Massen auf der Basis von Epoxiden".

Also in scientific literature the person skilled in the art can find a large number of other suitable initiators. In this respect we refer to the publication "Photoinduced Electron Transfer Reactions for macromolecular Synthesis" from S. D. Silab, S. Doran and Y. Yagci, Chem. Rev. 116, 10212-10275, 2016.

Component (D)—Organic, Polymerizable Monomers, which are not Polysiloxanes According to the Invention (i.e., are Other than Component (A)), Preferably for the Reaction with the Polysiloxanes According to the Invention The polymerizable monomers of Component (D) are monomers which—for the case of free-radically polymerization—are substances having preferably at least one (including two or more) ethylenic groups, for example, but not limited to, the (meth)acrylate monomers customarily used in dental chemistry.

The (meth)acrylate monomers may be monofunctional or polyfunctional.

Monofunctional (meth)acrylate monomers used with preference are the esters of (meth)acrylic acid with alkyl groups of 1 to 12 carbon atoms and esters of (meth)acrylic acid containing aromatic groups having 6 to 12 carbon atoms, wherein the alkyl groups and aromatic groups that form the esters may contain substituents such as hydroxyl groups and ether bonds.

The patent literature mentions a multitude of further compounds (for example in DE 39 41 629 A1), all of which are esters of acrylic or methacrylic acid and are suitable for use in a curable mixture.

The polymerizable monomers may also be hydroxyl compounds having at least one ethylenic double bond. The hydroxyl compounds of (meth)acrylates commonly used in dental chemistry can preferably be used.

Examples of polyfunctional (meth)acrylate monomers also include di(meth)acrylates of alkylene glycol having 2 to 20 carbon atoms, di(meth)acrylates of oligomers of alkylene glycol, polyalkylene glycol di(meth)acrylate, di(meth)acrylates of bisphenol A or of the diglycidyl ether of bisphenol A.

Particular preference is further given to polymerizable compounds based on a central polyalicyclic structural element, for example 3(4),8(9)-bis((meth)acryloyloxymethyl)tricyclo[5.2.1.0$^{2,6}$]decane, alkoxylated 3(4),8(9)-bis((meth)acryloyloxymethyl)tricyclo[5.2.1.0$^{2,6}$]decane, 2,3-bis((meth)-acryloyloxymethyl)bicyclo[2.2.1]heptane, alkoxylated 2,3-bis((meth)acryloyloxymethyl)bicyclo[2.2.1]heptane, 1,3,5-tri(meth)acryloyloxytricyclo[3.3.1.1$^{3,7}$]decane, alkoxylated tri(meth)acryloyloxytricyclo[3.3.1.1$^{3,7}$]-decane, and (meth)acrylates of tricyclo[5.2.1.0$^2$,6]decane-3(4),8(9)-dimethanol, alkoxylated tricyclo-[5.2.1.0$^2$,6]decane-3(4),8(9)-dimethanol, bicyclo[2.2.1]heptane-2,3-dimethanol, alkoxylated bicyclo[2.2.1]heptane-2,3-dimethanol, 1,3,5-adamantanetriol, alkoxylated 1,3,5-adamantanetriol, with urethane, urea, amide, allophanate, acylurea or biuret groups arranged between the polyalicyclic structural element and the (meth)acrylates.

Details of the preparation of these substituted (meth) acrylates can be found in patent applications EP 11 183 333, EP 11 183 328, EP 11 183 345, EP 11 183 338, EP 11 183 342 and EP 11 188 086, and in the publications cited in these documents.

Preference is also given to urethane (meth)acrylates, reaction products formed from 2 moles of a (meth)acrylate with a hydroxyl group and one mole of a diisocyanate.

Further preferred are the classical dental monomers ethylene glycol di(meth)acrylate, diethylene glycol di(meth)acrylate, 1,6-hexandiol di(meth)acrylate (HEDMA), triethylene glycol di(meth)acrylate (TEGDMA), dodecane-1,12-diol di(meth)acrylate, bisphenol A di(meth)acrylate, alkoxylated bisphenol A di(meth)acrylate, bisphenol B di(meth)acrylate, alkoxylated bisphenol B di(meth)acrylate, bisphenol C di(meth)acrylate, alkoxylated bisphenol C di(meth)acrylate, bisphenol F di(meth)acrylate, alkoxylated bisphenol F di(meth)acrylate, polyethylene glycol di(meth)acrylate, 7,7,9-trimethyl-3,14-dioxa-4,13-dioxo-5,12-diazahexadecan-1,16-diol di(meth)acrylate (UDMA), butanediol di(meth)acrylate, tetraethylene glycol di(meth)acrylate, neopentyl glycol di(meth)acrylate, 2-hydroxypropyl 1,3-di(meth)acrylate, 3-hydroxypropyl 1,2-di(meth)acrylate, pentaerythritol di(meth)acrylate, di(meth)acrylates of dihydroxymethyltricyclo[5.2.1.0$^{2,6}$]decane, 2-hydroxyethyl (meth)acrylate, 2-hydroxypropyl (meth)acrylate, 3-hydroxypropyl (meth)acrylate, 1,2-dihydroxypropyl (meth)acrylate, 1,3-dihydroxypropyl (meth)acrylate, 2,3-dihydroxypropyl (meth)acrylate, 2,2-bis-4-(2-hydroxypropoxy) phenyl)propane dimethacrylate (bis-GMA), trimethylolpropane tri(meth)acrylate, trimethylolethane tri(meth)acrylate, pentaerythritol tri(meth)acrylate, trimethylolmethane tri(meth)acrylate, pentaerythritol tetra(meth)acrylate, ditrimethylolpropane tetra(meth)acrylate, pentaerythritol hexa(meth)acrylate, butylene glycol di(meth)acrylate, propylene glycol di(meth)acrylate, nonanediol di(meth)acrylate, decanediol di(meth)acrylate, glycerol mono(meth)acrylate, glycerol di(meth)acrylate, trimethylolpropane mono(meth)acrylate, trimethylolpropane di(meth)acrylate, sorbitol mono-, di-, tri-, tetra- or penta(meth)acrylate, methyl (meth)acrylate, ethyl (meth)acrylate, propyl (meth)acrylate, butyl (meth)acrylate, hexyl (meth)acrylate, tetrahydrofurfuryl (meth)acrylate, lauryl (meth)acrylate, cyclohexyl (meth)acrylate, allyl (meth)acrylate, glycidyl (meth)acrylate, 2-ethoxyethyl (meth)acrylate, methoxy polyethylene glycol (meth)acrylate, isobornyl (meth)acrylate, 2-(N,N-dimethylamino)ethyl (meth)acrylate, N-methylol(meth)acrylamide, diacetone (meth)acrylamide, 2,2-bis[4-(meth)acryloyloxyphenyl]propane, 2,2-bis[4-(meth)acryloyloxyethoxyphenyl]propane, 2,2-bis[4-(meth)acryloyloxydiethoxyphenyl]propane, 2,2-bis[4-(meth)acryloyloxytriethoxyphenyl]propane, 2,2-bis[4-(meth)acryloyloxytetraethoxyphenyl]propane, 2,2-bis[4-(meth)acryloyloxypentaethoxyphenyl]propane, 2,2-bis[4-(meth)acryloyloxydipropoxyphenyl]propane, 2,2-bis[4-(meth)acryloyloxyethoxyphenyl]-2-[4-(meth)acryloyloxydiethoxyphenyl]propane, 2-[4-(meth)-acryloyloxydiethoxyphenyl]-2-[4-(meth)acryloyloxytriethoxyphenyl]propane, 2-[4-(meth)acryloyloxydipropoxy-phenyl]-2-[4-(meth)acryloyloxytriethoxyphenyl] propane, 2,2-bis[4-(meth)acryloyloxyisopropoxyphenyl] propane, neopentyl glycol hydroxypivalate di(meth)acrylate, aceto-acetatoxyethyl (meth)acrylate, polypropylene glycol di(meth)acrylate, glycerol alkoxylate dimethacrylate, neopentyl glycol (meth)acrylate, N,N-(1,2-dihydroxyethylene)bisacrylamide, 2,2-bis[4-(meth)acryloyloxypentaethoxyphenyl]propane, 2,2-bis[4-(meth)acryloyloxypolyethoxyphenyl]propane, diethylene glycol di(meth)acrylate, dipentaerythritol tetra(meth)acrylate, dipentaerythritol hexa(meth)acrylate, N,N-(2,2,4-trimethyl-hexamethylene)bis[2-(aminocarboxy)-propane-1,3-diol] tetra(meth)acrylate, the condensation product of 3-(4)-(meth)acryloyloxymethyl-8,(9)-hydroxymethyltricyclo [5.2.1.0$^{2,6}$]decane with dicarboxylic acids, 2-ethylhexyl (meth)acrylate, tridecyl (meth)acrylate, stearyl (meth)acrylate, benzyl (meth)acrylate, methoxy diethylene glycol (meth)acrylate, dicyclopentenyl (meth)acrylate, phenyl (meth)acrylate, pentaerythritol mono(meth)acrylate, dipentaerythritol mono(meth)acrylate, and caprolactone-modified tetrahydrofurfuryl(meth)acrylate.

The polymerizable monomers are monomers that are—for the case of a cationic polymerization—preferably one, two or more oxirane groups containing substances, such as, but not limited to, the monomer derivatives with an epoxycyclohexane unit or an epoxynorbornane unit commonly used in dental chemistry.

In the patent literature a large number of suitable compounds are described. Examples with detailed suitable synthesis informations can be found in DE 196 48 283 A1.

Component (E)—Acid Group Containing Monomers without Si Atom

Suitable monomers containing acid groups are 10-(meth)acryloyloxydecyl dihydrogen phosphate (10-MDP), 2-(meth)acryloyloxyethyl dihydrogen phosphate, 6-(meth)acryloyloxyhexyl dihydrogen phosphate, 4-(meth)acryloyloxybutyl dihydrogen phosphate, 8-(meth)acryloyloxyoctyl dihydrogen phosphate, 2-(meth)acryloyloxynonyl dihydrogen phosphate, 11-(meth)acryloyloxyundecyl dihydrogen phosphate, 20-(meth)acryloyloxyeicosyl dihydrogen phosphate, 1,3-di(meth)acyloyloxypropyl-2-dihydrogen phosphate, 2-(meth)acryloyloxyethylphenyl dihydrogen phosphate, di(2-(meth)acyloyloxyethyl) pyrophosphate, di(2-(meth)acyloyloxypropyl) pyrophosphate, di(2-(meth)acyloyloxybutyl) pyrophosphate, di(2-(meth)acyloyloxypentyl) pyrophosphate, di(2-(meth)acyloyloxyhexyl) pyrophosphate, di(2-(meth)acyloyloxydecyl) pyrophosphate, mono-, di- and/or triester of the phosphoric acid, which is obtained by the reaction of hydroxy-C2-C8-alkyl methacrylate (preferably hydroxyethyl methacrylate) or glycerol dimethacrylate with phosphorus oxychloride, glycerol dimethacrylate phosphate, pentaerythritol trimethacrylate phosphate, dipentaerythritol pentaacrylate phosphate, tetramethacryloxyethyl pyrophosphate, 4-Methacryloyloxyethyl trimellitic acid (4-MET), 4-methacryloxyethyl trimellitic anhydride (4-META), pyromellitic acid dimethacrylate, pyromellitic glycerol dimethacrylate, methacryloyloxyethyl phthalate, methacryloyloxyethyl maleate, methacryloyloxyethyl succinate, 1,3-glyceroldimethacrylate maleate and glycine-N,N'-1,2-ethanediylbis[N-(carboxymethyl)-1,1'-bis[2-[(2-methyl-1-oxo-2-propen-1-yl)oxy]ethyl]-ester.

Preferred monomers containing acid groups are 10-(meth)acryloyloxydecyl dihydrogen phosphate (10-MDP), glycerol dimethacrylate phosphate, penta-erythritoltrimethacrylate phosphate, dipentaerythritol pentaacrylate phosphate, tetra-methacryloxyethyl pyrophosphate, 4-Methacryloyloxyethyl trimellitic acid (4-MET), 4-methacryloxyethyl trimellitic anhydride (4-META), pyromellitic acid dimethacrylate, and pyromellitic glycerol dimethacrylate.

Further suitable monomers bearing acid groups are specified, for example, in EP 0980682 B1 and EP 0948955 A1. In the literature are mentioned further suitable monomers containing acid groups that improve adhesion.

Component (F)—Further Customary Additives

A polymerizable dental composition according to the invention can contain at least one (e.g., one, two, or more than two) common additive for dental compositions.

Suitable additives may be selected from the additives described herein or any other common additive for dental compositions.

These additives may have various functions. Customary additives for use in dental materials are known to those skilled in the art; he or she will select the suitable additive(s) according to the desired function. Typical additives and their functions are described by way of example hereinafter.

Polymerizable dental compositions preferably contain one or more inhibitor(s), also called stabilizer(s). These are typically added in order to prevent spontaneous polymerization. They react with free radicals formed prematurely, which are scavenged, prevent premature polymerization and increase the storage stability of the polymerizable dental composition. Standard inhibitors are phenol derivatives such as hydroquinone monomethyl ether (HQME) or 2,6-di-tert-butyl-4-methylphenol (BHT). Further inhibitors such as tert-butylhydroxyanisole (BHA), 2,2-diphenyl-1-picrylhydrazyl radicals, galvinoxyl radicals, triphenylmethyl radicals, 2,3,6,6-tetramethylpiperidinyl-1-oxyl radicals (TEMPO) and derivatives of TEMPO or phenothiazine and derivatives of phenothiazine are described in EP 0 783 880 B1. Alternative inhibitors are specified in DE 101 19 831 A1 or in EP 1 563 821 A1.

A polymerizable dental composition preferred in accordance with the invention may thus comprise, as additive, one or more polymerization inhibitor(s) for increasing the storage stability of the composition, preferably selected from the group consisting of hydroquinone monomethyl ether (HQME), phenols, preferably 2,6-di-tert-butyl-4-methylphenol (BHT) and tert-butylhydroxyanisole (BHA), 2,2-diphenyl-1-picrylhydrazyl radicals, galvinoxyl radicals, triphenylmethyl radicals, 2,3,6,6-tetramethylpiperidinyl-1-oxyl radical (TEMPO) and derivatives thereof, and phenothiazine and derivatives thereof.

A polymerizable composition of the invention may comprise, as additive, one or more fluoride-releasing substances, preferably sodium fluoride and/or amine fluorides.

UV absorbers are also included in the stabilizers and inhibitors, which are capable of absorbing UV radiation, for example, by their conjugated double bond systems and aromatic rings and are in some cases part of a polymerizable dental composition of the invention. Examples of UV absorbers are 2-hydroxy-4-methoxy-benzophenone, phenyl salicylate, 3-(2'-hydroxy-5'-methylphenyl)benzotriazole or diethyl 2,5-dihydroxy-terephthalate.

A polymerizable dental composition according to the invention can also comprise as additive one or more molecular weight regulators. Molecular weight regulators are known from the state of the art and are commercially available. They are used for example for the solution polymerization of olefins, the emulsion polymerization of methacrylates or for the production of moldings of PMMA molding compounds (PMMA=polymethyl methacrylate) by compression molding or injection molding.

Molecular weight regulators are so-called transfer reagents, which in a free radical reaction undergo transfer reactions and include mechanistical H abstraction and transmission of the free radical function to the regulator. Due to its function, the regulator is then found in the crosslinked polymer in the form of end groups.

Standard regulators are, for example, aldehydes and ketones, such as formaldehyde, acetaldehyde, propionaldehyde, n-butyraldehyde, isobutyraldehyde, methyl ethyl ketone, acetone, methyl isobutyl ketone, formic acid, ammonium formate, hydroxyammonium sulphate and hydroxyammonium phosphate, compounds containing sulphur in organically bound form, such as di-n-butyl sulphide, di-n-octyl sulphide, diphenyl sulphide, diisopropyl disulphide, di-n-butyl disulphide, di-n-hexyl disulphide, diacetyl disulphide and di-tert-butyl trisulphide, compounds containing sulphur in the form of SH groups, such as n-butyl mercaptan, n-hexyl mercaptan and n-dodecyl mercaptan, octadecyl mercaptan, further sulphur compounds such as hydrogensulphites, disulphites, compounds such as mercaptoethanol, mercaptobutanol, mercaptoacetic acid, 3-mercaptopropionic acid, mercaptosuccinic acid, thioglycerol, thioglycolic acid, diethanol sulphide, thiodiglycol, ethylthioethanol, 2,2,4,6,6-pentamethylheptane-4-thiol, 2,2,4,6,6,8,8-heptamethyl-nonane-4-thiol, thiourea, dimethyl sulphoxide, ethylhexyl thioglycolate, pentaerythritol tetrathioglycolate, mercaptopropyltrimethoxysilane, then allyl compounds such as allyl alcohol, allyl bromide, or benzyl compounds such as benzyl chloride or alkyl halides such as chloroform, bromotrichloromethane or tetrachloromethane, tetrabromomethane, methylene chloride, and also lower and higher molecular weight, monohydric or polyhydric alcohols such as methanol, ethanol, n-propanol, isopropanol, tert-butanol, sec-butanol, n-butanol, amyl alcohol, cyclohexanol, octanol, dodecanol, 1-ethylhexanol, glycerol, stearyl alcohol, oleyl alcohol, hydroxyethyl methacrylate or amines such as triethylamine, and toluene or ethylbenzene.

Preferred molecular weight regulators in inventive polymerizable dental compositions comprise various terpenes, especially terpinenes (α-terpinene, β-terpinene, γ-terpinene), phellandrenes (α-phellandrene, β-phellandrene) and terpinolene (also called δ-terpinene), 1,4-cyclohexadiene (optionally substituted), 1,3-cyclohexadiene (optionally substituted), 1,4-dihydronaphthalene, 1,4,5,8-tetrahydronaphthalene, 2,5-dihydrofuran or dimeric α-styrene (2,4-diphenyl-4-methyl-1-pentene), and linoleic acid and α-linolenic acid. These molecular weight regulators are described in the publications EP 2 374 444 B1 and EP 2 374 445 B1.

Double bond containing substances, which react according to a free-radically addition-fragmentation chain-transfer mechanism are also preferred molecular weight regulators in polymerizable dental compositions according to the invention. These agents are called AFCT reagents because of the expression "Addition-Fragmentation Chain Transfer Agents". Known AFCT reagents comprise special sulfur compounds such as allyl sulfides, allyl sulfones, dithioesters, dithiocarbamates, xanthates and trithiocarbonates.

Further known chain transmitter are reversible AFCR reagents, so called RAFT reagents.

Those substances are also preferably used in the polymerizable dental compositions according to the invention.

Further preferred transfer agents for the polymerizable compositions according to the invention are disclosed in the documents EP 3 090 722 A1, EP 2 916 801 B1, EP 2 748 206 B1, EP 2 965 742 A1, EP 3 058 014 B1, EP 3 166 569 B1, EP 3 046 962 B1 and EP 2 931 756 B1.

In some embodiments a preferred polymerizable dental composition according to the invention can contain also one or more plasticizers as additive. This substance class is comprehensively described for the use in polymerizable dental compositions. The following are explicitly named in the literature: Acid esters, selected from the group consisting of trimellitic acid esters, fatty acid esters, acetic acid esters, maleic acid esters, fumaric acid esters and citric acid esters, further tri-2-ethylhexyl trimellitate, dimethyl adipate, dibutyl adipate, diisobutyl adipate, diisonorbornyl adipate, di-2-ethylhexyl adipate, diisodecyl adipate, diethylenglycol adipate, dibutyldiglycol adipate, di-2-ethylhexyl azelate, dimethyl sebacate, dibutyl sebacate, di-2-ethylhexyl sebacate, methyl acetyl ricinoleate, epoxidized soybean oil, glycerol triacetate, 2-ethylhexyl acetate, dimethyl maleate, dibutyl maleate, di-2-ethylhexyl maleate, dibutyl fumarate, di-2-ethylhexyl fumarate, trimethyl citrate, triethyl citrate, tripropyl citrate and triisobutyl citrate, and also polyethylene glycol derivatives, polypropylene glycols, low molecular weight polyesters, dibutyl-, dioctyl-, dinonyl-, diphenyl phthalates, diisononyl adipates, tricresyl phosphates and silicone oils, dibenzyltoluene or polyethoxylated sorbitan esters, phthalic acid esters of longer crosslinked alcohols such as bis(2-ethylhexyl) phthalate or Phthalic acid polyesters, $C_2$ to $C_{18}$-dialkyl esters of C2 to $C_6$ dicarboxylic acids, such as dioctyl malate, diisopropyl adipate, aromatic or aliphatic sulfonic acid esters, such as $C_2$- to $C_{20}$-alkylsulfonic acid ester of phenols or of $C_1$ to $C_{18}$-alcohols and typical aromatic plasticizers such as polyphenyls, and isomer mixtures of $C_{20}$- to $C_{30}$-aromatics, biphenyl, 1,2-diphenylethane, decanol, 2,4,6-trimethylnaphthalene, hexamethylbenzene, diphenylmethane, 1,1-diphenylethane, pentadecane, 2,3-dimethylbiphenyl, cinnamyl alcohol, dibenzy lether, hexaethylbenzene, refined mineral oils, oleic acid, castor oil, corn oil, camphor, and sugar alcohols, and also tributyl phosphate, tri-2-ethylhexyl phosphate, triphenyl phosphate and tricresyl phosphate and plasticizers comprising a central polyalicyclic structural element. For the plasticizers mentioned, reference is made to the patent literature EP 2 623 087 B1, EP 2 623 086 B1, DE 101 47 125 A1, EP 1 194 110 B1, DE 32 46 654 A1, DE 101 26 476 A1, DE 197 11 514 B4, DE 39 02 417 A1, DE 199 61 341 C2, DE 197 54 029 A1, DE 60 2004 009 552 T2, DE 10 2008 283 306, DE 699 21 231 T2, DE 692 31 737 T2, DE 690 17 484 T2, DE 697 25 380 T2, DE 698 01 010 T2, DE 20 2010 014 676 U1, DE 199 41 738 B4, DE 10 2009 046 251 A1, DE 2420351 C3.

Since the teeth should be restored as naturally as possible, it is necessary to provide dental compositions of the invention in a wide variety of different shades. Preferred curable dental materials of the invention have characteristic shades, preferably a tooth shade covered by the "VITA classical A1-D4 shades"; such shades are referred to as A1-A4 (reddish-brownish), B1-B4 (reddish-yellowish), C1-C4 (grey shades), D2-D4 (reddish-grey). For the shade adjustment, generally inorganic dyes and organic pigments are utilized in very small amounts, which are thus used as an additive in preferred embodiments.

Further optional additives are aromas, dental medicines, organic polymers and oligomers, microbicides, preferably bactericides, interface-active substances, preferably surfactants and preservatives, preferably parabenes, rheological auxiliaries and thickeners.

Component (G)—Solvents

A polymerizable dental composition according to the invention, for example a dental adhesive, can also contain a solvent up to 70% by weight based on the total composition. As solvent the composition can also contain water. Further suitable are the commonly used organic solvents for example hydrocarbons, ketones and esters such as toluene, xylene, isooctane, acetone, butanone, methyl isobutyl ketone, ethyl acetate, butyl acetate, tetrahydrofuran, N-methylpyrrolidone, dimethylacetamine and dimethylformamide. Also alcohols such as ethanol, propanols, butanols, pentanols, hexanols, cyclohexanol, heptanols, octanols, nonanols, decanols, etc., may be used. Also suitable are cycloaliphatic and arylaliphatic alcohols.

In a preferred embodiment, the polymerizable dental composition according to the invention, for example a dental adhesive, contains an organic solvent, preferably selected from the group consisting of water miscable organic solvents, preferably acetone, ethanol, n-propanol and isopropanol and also mixtures thereof.

Especially preferred the polymerizable dental composition according to the invention, for example a dental adhesive, contains water and a water miscible organic solvent/mixture. The ratio of the organic solvent(s)/mixture to water is preferred in the range of 1:1 to 10:1, preferably in the range of 2:1 to 8:1 and further preferably in the range of 3:1 to 5:1.

In one embodiment, the inventive polymerizable dental composition contains the following components:
(A) in an amount of 5 to 99.69% by weight,
(B) in an amount of 0.3 to 92% by weight,
(C) in an amount of 0.01 to 5% by weight,
(D) in an amount of 0 to 94% by weight,
(E) in an amount of 0 to 20% by weight,
(F) in an amount of 0 to 20% by weight, and
(G) in an amount of 0 to 70% by weight,
wherein the weights are based on the respective overall composition.

In one embodiment, preferred inventive polymerizable dental compositions may contain the following components:
(A) in an amount of 5 to 19.99% by weight,
(B) in an amount of 80 to 92% by weight,
(C) in an amount of 0.01 to 5% by weight,
(D) in an amount of 0 to 14% by weight, and
(F) in an amount of 0 to 8% by weight,
or
(A) in an amount of 5 to 49.99% by weight,
(B) in an amount of 50 to 80% by weight,
(C) in an amount of 0.01 to 5% by weight,
(D) in an amount of 0 to 35% by weight,
(E) in an amount of 0 to 20% by weight, and
(F) in an amount of 0 to 20% by weight,
or
(A) in an amount of 5 to 99.69% by weight,
(B) in an amount of 0.3 to 50% by weight,
(C) in an amount of 0.01 to 5% by weight,
(D) in an amount of 0 to 94% by weight,
(E) in an amount of 0 to 20% by weight,
(F) in an amount of 0 to 20% by weight, and
(G) in an amount of 0 to 70% by weight,
wherein the weights are based on the respective overall composition.

In particularly preferred cases, the polymerizable dental composition according to the invention does not contain any component (D).

As mentioned above, the inventive polymerizable dental composition can be cured. The present invention thus also is directed to a polymerized dental composition obtainable from an inventive polymerizable dental composition (as defined above, preferably a polymerizable composition as defined above as preferred) by means of polymerization of the polysiloxane compounds present in the composition, and optionally of further polymerizable constituents present in the dental composition. The polymerization is initiated preferably either free-radically by means of the organically polymerizable double bonds present in the (meth)acrylate groups or cationically by a ring-opening mechanism via an oxirane group.

The statements made above with regard to preferred embodiments of polymerizable dental compositions of the invention apply also correspondingly to the polymerized dental compositions of the invention.

A main aspect of the present invention is directed to a polymerizable dental composition according to the invention (as described above, preferably as defined above as preferred) or a polymerized dental composition according to the invention (as described above, preferably as defined above as preferred) for the use in a therapeutic method (a method for the therapeutic treatment of the human or animal body, preferably the human body).

Especially preferred is the specific application of the polymerizable dental composition according to the invention or the polymerized dental composition according to the invention in a therapeutic method for the temporary or permanent filling of a dental cavity or in a therapeutic method as dental filling material, dental bulk-fill material, dental base material, dental core build-up material, dental luting cement, dental crown material, dental bridge material, relining material, dental adhesive (bonding), dental lacquer, dental sealing material, flowable dental composite material, dental inlay, dental onlay, dental overlay, artificial tooth, orthodontic material, dental framework, dental prosthesis, dental temporary prosthesis or dental block material.

Especially preferred is a polymerizable dental composition according to the invention or a polymerized dental material according to the invention for the specific application in a therapeutic method for temporary or permanent filling a dental cavity, or in a therapeutic method as:

a.) packable filling composite, packable bulk-fill material, inlay, onlay, overlay, dental block material, false teeth, dental framework, wherein it contains
  (A) in an amount of 5 to 19.99% by weight,
  (B) in an amount of 80 to 92% by weight,
  (C) in an amount of 0.01 to 5% by weight,
  (D) in an amount of 0 to 14% by weight, and
  (F) in an amount of 0 to 8% by weight, or as b.) flowable filling composite, flowable bulk-fill material, core build-up material, luting cement, crown and bridge material, orthodontic material, base material or relining material, wherein it contains
  (A) in an amount of 5 to 49.99% by weight,
  (B) in an amount of 50 to 80% by weight,
  (C) in an amount of 0.01 to 5% by weight,
  (D) in an amount of 0 to 35% by weight,
  (E) in an amount of 0 to 20% by weight, and
  (F) in an amount of 0 to 20% by weight, or as c.) dental adhesive, dental sealing material, dental lacquer, dental primer or dental printing composition in additive manufacturing methods, also known as "rapid prototyping", preferably for stereolithography and here preferred for digital light processing (DLP), selective laser assembling (SLA), for microstereolithography, for 3D-printing, for laminated object manufacturing or for film transfer imaging, wherein it contains
  (A) in an amount of 5 to 99.69% by weight,
  (B) in an amount of 0.3 to 50% by weight,
  (C) in an amount of 0.01 to 5% by weight,
  (D) in an amount of 0 to 94% by weight,
  (E) in an amount of 0 to 20% by weight,
  (F) in an amount of 0 to 20% by weight and
  (G) in an amount of 0 to 70% by weight, and
  wherein the weights are based on the respective overall composition.

The present invention also relates to a method for producing a polymerizable dental composition comprising the following steps:
  providing components (A), (B), (C), and optionally the components (D), (E), (F), and/or (G), and
  mixing the components.

The present invention additionally also relates to a method for producing a polymerized, preferably a free-radically polymerized, dental composition, comprising the following steps:
  providing components (A), (B), (C), and optionally the components (D), (E), (F), and/or (G),
  mixing the components and
  polymerizing, preferably free-radically polymerizing, the mixture.

Preferably, the polymerizable dental compositions are used as part of a kit of the invention. The present invention thus also relates to a kit comprising:
  at least one (e.g., one, two or more than two) polymerizable dental composition of the invention in a syringe and/or compule,
    optionally at least one (e.g., one, two or more than two) adhesive,
    optionally at least one (e.g., one, two or more than two) etching gels,
    optionally at least one (e.g., one or more than one) shade guide, and
    optionally at least one (e.g., one or more than one) brush.

EXAMPLES

Abbreviations

CQ: DL-camphorquinone
DABE: ethyl 4-dimethylaminobenzoate
BHT: 2,6-di-tert-butyl-4-methylphenol
BPO: dibenzoyl peroxide
DEPT: N,N-Bis(2-hydroxyethyl)-p-toluidine
NTPB: sodium tetraphenylborate
BisGMA: 2,2-bis[4-(2-hydroxy-3-methacryloxypropyloxy)phenyl]propane
TEGDMA: triethylene glycol dimethacrylate
MDP: 10-methacryloyloxydecyl phosphate
Dental glass 1: barium aluminium borosilicate glass (D50 0.8 µm/D25 0.5 µm/D75 1.0 µm), silanized with γ-methacryloxypropyl-trimethoxysilane
Dental glass 2: barium aluminium borosilicate glass (D50 2.7 µm/D25 1.4 µm/D75 6.1 µm), silanized with γ-methacryloxypropyl-trimethoxysilane
Fumed-$SiO_2$: fumed silica (D50 40 nm), silanized with γ-methacryloxypropyl-trimethoxysilane
Nano-$SiO_2$: non-agglomerated, non-aggregated silica (D50 40 nm), silanized with γ-methacryloxypropyl-trimethoxysilane

Synthesis of the Silanes (a1)

Synthesis of 9,9-dimethoxy-4-oxo-5,10-dioxa-3-aza-9-silaundec-1-yl Methacrylate (Example 1a)

18.03 g (0.1 mol) of 3-(trimethoxysilyl)-1-propanol was heated with 15.52 g of (0.1 mol) 2-isocyanatoethyl methacrylate, 0.25% by weight of dibutyltin dilaurate and 200 ppm BHT at 55° C. for 6 hours with stirring. As a reaction control, the disappearance of the NCO band is observed at about 2270 $cm^{-1}$ in the IR spectrum. A pale yellow liquid was obtained. Viscosity (25° C.): 20 mPa*s. $n^D_{20}$:1.448.

IR (film): $\tilde{v}$ ($cm^{-1}$) 3361 (w, NH), 2972 (w), 1715 (vs, C=O), 1639 (w), 1525 (m), 1447 (w), 1244 (m), 1166 (m), 1073 (vs), 946 (s), 771 (s).

$^1$H NMR (60 MHz, $CDCl_3$): δ (ppm) 0.7-1.0 (m, 2H, $SiCH_2$), 1.9-2.1 (m, 2H, $SiCH_2CH_2$), 2.05 (s, 3H, $CH_3$), 3.2-3.5 (m, 2H, $SiCH_2CH_2CH_2$), 3.60 (s, 9H, $OCH_3$), 4.07 (t, 2H, $NCH_2$), 4.42 (t, 2H, $OCH_2$), 5.05 (s, 1H, NH), 5.59 (1H, C=CH), 6.17 (1H, C=CH).

Synthesis of 9,9-dimethoxy-4-oxo-5-oxa-3-aza-9-siladec-1-yl Methacrylate (Example 1b)

16.43 g (0.1 mol) of 3-(methyldimethoxysilyl)-1-propanol was heated with 15.52 g (0.1 mol) of 2-isocyanatoethyl methacrylate, 0.25% by weight of dibutyltin dilaurate and 200 ppm BHT at 55° C. for 6 hours with stirring. As a reaction control, the disappearance of the NCO band is observed at about 2270 $cm^{-1}$ in the IR spectrum. A pale yellow liquid was obtained. Viscosity (25° C.): 20 mPa*s. $n^D_{20}$:1.460.

IR (film): $\tilde{v}$ ($cm^{-1}$) 3353 (w, NH), 2946 (w), 1713 (vs, C=O), 1637 (w), 1529 (m), 1451 (w), 1247 (m), 1166 (m), 1077 (vs), 945 (s), 767 (s).

$^1$H NMR (60 MHz, $CDCl_3$): δ (ppm) 0.12 (s, 3H $SiCH_3$), 0.9-1.2 (m, 2H, $SiCH_2$), 1.9-2.1 (m, 2H, $SiCH_2CH_2$), 2.05 (s, 3H, $CH_3$), 3.2-3.5 (m, 2H, $SiCH_2CH_2CH_2$), 3.62 (s, 6H, OCH$_3$), 4.08 (t, 2H, NCH$_2$), 4.42 (t, 2H, OCH$_2$), 5.05 (s, 1H, NH), 5.59 (1H, C=CH), 6.17 (1H, C=CH).

Synthesis of 7,7-diethoxy-4-oxo-5,8-dioxa-3-aza-7-siladec-1-yl Methacrylate (Example 1c)

19.43 g (0.1 mol) of 1-(triethoxysilyl)methanol was heated with 15.52 g (0.1 mol) of 2-isocyanatoethyl methacrylate, 0.25% by weight of dibutyltin dilaurate and 200 ppm BHT at 55° C. for 6 hours with stirring. As a reaction control, the disappearance of the NCO band is observed at about 2270 cm$^{-1}$ in the IR spectrum. A pale yellow liquid was obtained. Viscosity (25° C.): 21 mPa*s. n$^D_{20}$:1.455.

IR (film): ṽ (cm$^{-1}$) 3352 (w, NH), 2970 (w), 1717 (vs, C=O), 1635 (w), 1532 (m), 1451 (w), 1245 (m), 1163 (m), 1072 (vs), 945 (s), 776 (s).

$^1$H NMR (60 MHz, CDCl$_3$): δ (ppm) 1.32 (t, 9H, OCH$_2$CH$_3$), 2.05 (s, 3H, CH$_3$), 2.70 (m, 2H, SiCH$_2$), 3.92 (q, 6H, OCH$_2$CH$_3$), 4.09 (t, 2H, NCH$_2$), 4.41 (t, 2H, OCH$_2$), 5.07 (s, 1H, NH), 5.57 (1H, C=CH), 6.19 (1H, C=CH).

Synthesis of 9,9-dimethoxy-4-oxo-3,10-dioxa-5-aza-9-silaundec-1-yl Methacrylate (Example 1d)

20.53 g (0.1 mol) of 3-(trimethoxysilyl)propyl isocyanate was heated with 13.01 g (0.1 mol) of 2-hydroxyethyl methacrylate (HEMA), 0.25% by weight of dibutyltin dilaurate and 200 ppm BHT at 55° C. for 6 hours with stirring. As a reaction control, the disappearance of the NCO band is observed at about 2270 cm$^{-1}$ in the IR spectrum. A pale yellow liquid was obtained. Viscosity (25° C.): 21 mPa*s. n$^D_{20}$:1.448.

IR (film): ṽ (cm$^{-1}$) 3356 (w, NH), 2974 (w), 1716 (vs, C=O), 1638 (w), 1527 (m), 1448 (w), 1242 (m), 1164 (m), 1072 (vs), 947 (s), 773 (s).

$^1$H NMR (60 MHz, CDCl$_3$): δ (ppm) 0.6-0.9 (m, 2H, SiCH$_2$), 1.6-1.8 (m, 2H, SiCH$_2$CH$_2$), 2.05 (s, 3H, CH$_3$), 3.1-3.4 (m, 2H, SiCH$_2$CH$_2$CH$_2$), 3.61 (s, 9H, OCH$_3$), 4.21 (t, 2H, OCH$_2$), 4.41 (t, 2H, OCH$_2$), 5.17 (s, 1H, NH), 5.68 (1H, C=CH), 6.24 (1H, C=CH).

Synthesis of 2-methyl-9,9-dimethoxy-4-oxo-3,10-dioxa-5-aza-9-silaundec-1-yl Methacrylate (Example 1e)

20.53 g (0.1 mol) of 3-(trimethoxysilyl)propyl isocyanate was heated with 14.42 g (0.1 mol) of 2-hydroxypropyl methacrylate (HPMA), 0.25% by weight of dibutyltin dilaurate and 200 ppm BHT at 55° C. for 6 hours with stirring. As a reaction control, the disappearance of the NCO band is observed at about 2270 cm$^{-1}$ in the IR spectrum. A pale yellow liquid was obtained. Viscosity (25° C.): 27 mPa*s. n$^D_{20}$:1.448.

IR (film): ṽ (cm$^{-1}$) 3360 (w, NH), 2975 (w), 1713 (vs, C=O), 1638 (w), 1526 (m), 1449 (w), 1242 (m), 1164 (m), 1072 (vs), 947 (s), 773 (s).

$^1$H NMR (60 MHz, CDCl$_3$): δ (ppm) 0.4-0.7 (m, 2H, SiCH$_2$), 1.15 (d, 3H, CH$_3$), 0.4-1.7 (m, 2H, SiCH$_2$CH$_2$), 1.94 (s, 3H, CH$_3$), 3.0-3.3 (m, 2H, SiCH$_2$CH$_2$CH$_2$), 3.61 (s, 9H, OCH$_3$), 4.15 (d, 4H, OCH$_2$), 4.8-5.2 (m, 2H, NH+OCH), 5.52 (1H, C=CH), 6.12 (1H, C=CH).

Synthesis of 2-[[[[3-(trimethoxysilyl)propyl] amino]carbonyl]oxy]-1,3-propanediyl Methacrylate (Example 1f)

20.53 g (0.1 mol) of 3-(trimethoxysilyl)propyl isocyanate was heated with 22.82 g (0.1 mol) of glycerol 1,3-dimethacrylate, 0.25% by weight of dibutyltin dilaurate and 200 ppm BHT at 55° C. for 6 hours with stirring. As a reaction control, the disappearance of the NCO band is observed at about 2270 cm$^{-1}$ in the IR spectrum. A pale yellow liquid was obtained. Viscosity (25° C.): 100 mPa*s. n$^D_{20}$:1.460.

IR (film): ṽ (cm$^{-1}$) 3366 (w, NH), 2974 (w), 1718 (vs, C=O), 1638 (w), 1525 (m), 1450 (w), 1294 (w), 1241 (m), 1157 (m), 1072 (vs), 946 (s), 776 (s).

$^1$H NMR (60 MHz, CDCl$_3$): δ (ppm) 0.5-0.8 (m, 2H, SiCH$_2$), 1.5-1.7 (m, 2H, SiCH$_2$CH$_2$), 1.97 (s, 3H, CH$_3$), 3.0-3.3 (m, 2H, SiCH$_2$CH$_2$CH$_2$), 3.61 (s, 9H, OCH$_3$), 4.3 (d, 4H, OCH$_2$), 5.00 (s, 1H, NH), 5.25 1 (m, 1H, OCH), 5.62 (1H, C=CH), 6.15 (1H, C=CH).

Synthesis of 17,17-dimethoxy-7,9-dioxo-3,10,15-trioxa-6,8-diaza-8-(2-methacryloyloxyethyl)-17-silahexadec-1-yl Methacrylate (Example 1q)

12.02 g (0.067 mol) of 3-(trimethoxysilyl)-1-propanol was heated with 20.69 g (0.133 mol, 2 eq.) of 2-isocyanatoethyl methacrylate, 0.25% by weight of dibutyltin dilaurate and 200 ppm BHT at 55° C. for 6 hours with stirring. As a reaction control, the disappearance of the NCO band is observed at about 2270 cm$^{-1}$ in the IR spectrum. A pale yellow liquid was obtained. Viscosity (25° C.): 34 mPa*s. n$^D_{20}$:1.454.

IR (film): ṽ (cm$^{-1}$) 3405 (s, NH), 2972 (w), 1712 (vs, C=O), 1635 (w), 1527 (m), 1446 (w), 1245 (s), 1164 (w), 1072 (vs), 945 (s), 770 (s).

$^1$H NMR (60 MHz, CDCl$_3$): δ (ppm) 0.7-1.0 (m, 2H, SiCH$_2$), 1.9-2.1 (m, 2H, SiCH$_2$CH$_2$), 2.05 (s, 3H, CH$_3$), 2.10 (s, 3H, CH$_3$), 3.2-3.5 (m, 2H, SiCH$_2$CH$_2$CH$_2$), 3.60 (s, 9H, OCH$_3$), 4.0-4.2 (4H, NCH$_2$), 4.4-4.6 (4H, OCH$_2$), 7.5 (1H, NH), 5.5-5.7 (2H, C=CH), 6.1-6.3 (2H, C=CH).

Synthesis of 9,9-diethoxy-4-oxo-5-oxa-3-aza-9-silaundec-1-yl Methacrylate (Example 1h)

5.81 g (0.1 mol) of 2-propen-1-ol was heated with 15.52 g (0.1 mol) of 2-isocyanatoethyl methacrylate, 0.25% by weight of dibutyltin dilaurate and 200 ppm BHT at 55° C. for 6 hours with stirring. As a reaction control, the disappearance of the NCO band is observed at about 2270 cm$^{-1}$ in the IR spectrum. A pale yellow liquid was obtained, which was further directly converted.

16.43 g (0.1 mol) of triethoxysilane and 0.2% Karstedt's catalyst solution (platinum(0)-1,3-divinyl-1,1,3,3-tetramethyldisiloxane in vinyl-terminated polydimethylsiloxane, 1% Pt) were added and heated at 80° C. for 2 hours with stirring. A pale yellow liquid was obtained. Viscosity (25° C.): 20 mPa*s. n$^D_{20}$:1.450.

IR (film): ṽ (cm$^{-1}$) 3357 (w, NH), 2975 (w), 1716 (vs, C=O), 1637 (w), 1525 (m), 1447 (w), 1241 (m), 1164 (m), 1072 (vs), 947 (s), 773 (s).

$^1$H NMR (60 MHz, CDCl$_3$): δ (ppm) 0.7-1.0 (m, 2H, SiCH$_2$), 1.32 (t, 9H, OCH$_2$CH$_3$), 1.8-2.0 (m, 2H, SiCH$_2$CH$_2$), 2.05 (s, 3H, CH$_3$), 3.4-3.6 (m, 2H, SiCH$_2$CH$_2$CH$_2$), 3.85 (q, 6H, OCH$_2$CH$_3$), 4.07 (t, 2H, NCH$_2$), 4.42 (t, 2H, OCH$_2$), 5.08 (s, 1H, NH), 5.57 (1H, C=CH), 6.14 (1H, C=CH).

Synthesis of 9,9-diethoxy-4-oxo-3-oxa-5-aza-9-silaundec-1-yl Methacrylate (Example 1i)

8.31 g (0.1 mol) of 3-isocyanato-1-propene was heated with 13.01 g of (0.1 mol) 2-hydroxyethyl methacrylate (HEMA), 0.25% by weight of dibutyltin dilaurate and 200 ppm BHT at 55° C. for 6 hours with stirring. As a reaction control, the disappearance of the NCO band is observed at about 2270 cm$^{-1}$ in the IR spectrum. A pale yellow liquid was obtained, which is further directly converted.

16.43 g (0.1 mol) of triethoxysilane and 0.2% Karstedt's catalyst solution (platinum(0)-1,3-divinyl-1,1,3,3-tetramethyldisiloxane in vinyl-terminated poly-dimethylsiloxane, 1% Pt) were added and heated at 80° C. for 2 hours with stirring. A pale yellow liquid was obtained. Viscosity (25° C.): 21 mPa*s. $n^D_{20}$:1.450.

IR (film): $\tilde{v}$ (cm$^{-1}$) 3356 (w, NH), 2974 (w), 1716 (vs, C=O), 1638 (w), 1527 (m), 1448 (w), 1242 (m), 1164 (m), 1072 (vs), 947 (s), 773 (s).

$^1$H NMR (60 MHz, CDCl$_3$): δ (ppm) 0.6-0.9 (m, 2H, SiCH$_2$), 1.32 (t, 9H, OCH$_2$CH$_3$), 1.6-1.8 (m, 2H, SiCH$_2$CH$_2$), 2.05 (s, 3H, CH$_3$), 3.1-3.4 (m, 2H, SiCH$_2$CH$_2$CH$_2$), 3.92 (q, 6H, OCH$_2$CH$_3$), 4.41 (s, 4H, OCH$_2$CH$_2$O), 5.17 (s, 1H, NH), 5.68 (1H, C=CH), 6.24 (1H, C=CH).

Synthesis of the Silanes (a2)

Synthesis of 3-methacryloyloxypropylmethyldimethoxysilane (Example 2a)

12.62 g (0.1 mol) allyl methacrylate, 10.62 g (0.1 mol) methyldimethoxysilane and 0.2% Karstedt's catalyst solution (platinum(0)-1,3-divinyl-1,1,3,3-tetramethyldisiloxane in vinyl-terminated polydimethylsiloxane, 1% Pt) were heated for 2 hours at 80° C. while stirring. A pale yellow liquid was obtained. Viscosity (25° C.): 5 mPa*s. $n^D_{20}$: 1.436.

IR (film): $\tilde{v}$ (cm$^{-1}$) 2947 (w), 1718 (vs, C=O), 1638 (w), 1525 (m), 1454 (w), 1296 (m), 1162 (s), 1080 (vs), 814 (s), 765 (s).

$^1$H NMR (60 MHz, CDCl$_3$): δ (ppm) 0.12 (s, 3H SiCH$_3$), 0.6-0.9 (m, 2H, SiCH$_2$), 1.7-1.9 (m, 2H, SiCH$_2$CH$_2$), 2.00 (s, 3H, CH$_3$), 3.56 (s, 3H OCH$_3$), 4.16 (t, 2H, SiCH$_2$CH$_2$CH$_2$), 5.58 (1H, C=CH), 6.14 (1H, C=CH).

Synthesis of N-[3-(dimethoxymethylsilyl)propyl]-2-methyl-2-propenamide (Example 2b)

12.52 g (0.1 mol) N-allylmethacrylamide, 10.62 g (0.1 mol) methyldimethoxysilane and 0.2% Karstedt's catalyst solution (Platinum(0)-1,3-divinyl-1,1,3,3-tetramethyldisiloxane in vinyl-terminated polydimethylsiloxane, 1% Pt) were heated for 2 hours at 80° C. under stirring. A pale yellow liquid was obtained. Viscosity (25° C.): 9 mPa*s. $n^D_{20}$:1.439.

IR (film): $\tilde{v}$ (cm$^{-1}$) 3351 (w, NH), 2948 (w), 1716 (vs, C=O), 1636 (w), 1524 (m), 1452 (w), 1295 (m), 1162 (s), 1079 (vs), 812 (s), 766 (s).

$^1$H NMR (60 MHz, CDCl$_3$): δ (ppm) 0.12 (s, 3H SiCH$_3$), 0.4-0.7 (m, 2H, SiCH$_2$), 1.5-1.7 (m, 2H, SiCH$_2$CH$_2$), 2.05 (s, 3H, CH$_3$), 3.0-3.3 (m, 2H, SiCH$_2$CH$_2$CH$_2$), 3.50 (s, 3H OCH$_3$), 5.36 (1H, C=CH), 5.85 (1H, C=CH), 6.94 (1H, NH).

Synthesis of the Silanes (a3)

Synthesis of dimethoxyphenylmethylsilane (Example 3a)

According to example 1 from WO 2012/091154 A1, 0.47 g (1.5 mmol) bismuth(III)-chloride, 8.82 g (0.1 mol) tert.-butylmethylether and 19.11 g (0.1 mol) dichlorophenylmethylsilane were converted. A pale yellow solid was obtained. m.p.: 73° C. $n^D_{20}$:1.469.

Synthesis of 9,9-dimethoxy-9H-9-silafluorene (Example 3b)

According to example 1 from WO 2012/091154 A1 0.47 g (1.5 mmol) bismuth(III)-chloride, 8.82 g (0.1 mol) tert.-butylmethylether and 25.12 g (0.1 mol) 9,9-dichloro-9H-9-silafluorene were converted. A slowly crystallizing yellow oil was obtained. $n^D_{20}$:1.545.

Synthesis of Polysiloxanes:
General Condensation Procedure:

0.1 mol silane compound(s) and 0.5 mmol BHT are dissolved in 100 ml ethyl acetate. Then 2.5 ml of 1N HCl solution is added and heated for 72 hours at 30° C. The organic phase is extracted with 2N NaOH solution and washed with water. Afterwards it is dried over magnesium sulfate and the solvent is removed in vacuum.

Example 4a

According to the general condensation procedure, 0.2 mol of 9,9-dimethoxy-4-oxo-5,10-dioxa-3-aza-9-silaundec-1-yl Methacrylate (silane a1), 0.2 mol of γ-methacyloxypropyltrimethoxysilane (silane a2) and 0.2 mol of dimethoxydiphenylsilane (silane a3) were condensed in presence of 0.3 mmol BHT in 60 ml ethyl acetate. A pale yellow liquid was obtained. Viscosity (25° C.): 24 Pa*s. $n^D_{20}$:1.515.

Example 4b

According to the general condensation procedure, 0.4 mol of 9,9-dimethoxy-4-oxo-5,10-dioxa-3-aza-9-silaundec-1-yl Methacrylate (silane a1), 0.2 mol of γ-methacyloxypropyltrimethoxysilane (silane a2) and 0.2 mol of dimethoxydiphenylsilane (silane a3) were condensed in presence of 0.4 mmol BHT in 80 ml ethyl acetate. A pale yellow liquid was obtained. Viscosity (25° C.): 29 Pa*s. $n^D_{20}$:1.509.

Example 4c

According to the general condensation procedure, 0.4 mol of 7,7-diethoxy-4-oxo-5,8-dioxa-3-aza-7-silaundec-1-yl Methacrylate (silane a1), 0.2 mol of γ-methacyloxypropyltrimethoxysilane (silane a2) and 0.2 mol of dimethoxydiphenylsilane (silane a3) were condensed in presence of 0.4 mmol BHT in 80 ml ethyl acetate. A pale yellow liquid was obtained. Viscosity (25° C.): 28 Pa*s. $n^D_{20}$:1.510.

Example 4d

According to the general condensation procedure, 0.4 mol of 17,17-dimethoxy-7,9-dioxo-3,10,15-trioxa-6,8-diaza-8-(2-methacryloyloxyethyl)-17-silahexadec-1-yl Methacrylate (silane a1), 0.2 mol of γ-methacyloxypropyltrimethoxysilane (silane a2) and 0.2 mol of dimethoxydiphenylsilane (silane a3) were condensed in presence of 0.4 mmol BHT in 80 ml ethyl acetate. A pale yellow liquid was obtained. Viscosity (25° C.): 38 Pa*s. $n^D_{20}$:1.518.

Example 5a

According to the general condensation procedure, 0.8 mol of 9,9-dimethoxy-4-oxo-5,10-dioxa-3-aza-9-silaundec-1-yl Methacrylate (silane a1) was condensed in presence of 0.4 mmol BHT in 80 ml ethyl acetate. A pale yellow liquid was obtained.

Example 5b

According to the general condensation procedure, 0.8 mol of 9,9-dimethoxy-4-oxo-5-oxa-3-aza-9-silaundec-1-yl Methacrylate (silane a1) was condensed in presence of 0.4 mmol BHT in 80 ml ethyl acetate. A pale yellow liquid was obtained.

Example 5c

According to the general condensation procedure, 0.8 mol of 7,7-dimethoxy-4-oxo-5,8-dioxa-3-aza-7-silaundec-1-yl Methacrylate (silane a1) was condensed in presence of 0.4 mmol BHT in 80 ml ethyl acetate. A pale yellow liquid was obtained.

Example 5d

According to the general condensation procedure, 0.8 mol of 2-[[[[3-(trimethoxysilyl)propyl]amino]carbonyl]oxy]-1,3-propanediyl methacrylate (silane a1) was condensed in presence of 0.4 mmol BHT in 80 ml ethyl acetate. A pale yellow liquid was obtained.

Example 5e

According to the general condensation procedure, 0.6 mol of 17,17-dimethoxy-7,9-dioxo-3,10,15-trioxa-6,8-diaza-8-(2-methacryloyloxyethyl)-17-silahexadec-1-yl Methacrylate (silane a1) was condensed in presence of 0.3 mmol BHT in 60 ml ethyl acetate. A pale yellow liquid was obtained.

Example 5f

According to the general condensation procedure, 0.8 mol of γ-methacyloxypropyltrimethoxysilane (silane a2) was condensed in presence of 0.4 mmol BHT in 80 ml ethyl acetate. A pale yellow liquid was obtained. Viscosity (25° C.): 20 Pa*s. $n^D_{20}$:1.479.

Example 5g

According to the general condensation procedure, 0.8 mol of γ-methacyloxypropylmethyldimethoxysilane (sila(i a2) was condensed in presence of 0.4 mmol BHT in 80 ml ethyl acetate. A pale yellow liquid was obtained. Viscosity (25° C.): 3 Pa*s. $n^D_{20}$:1.466.

Example 5h

According to the general condensation procedure, 0.8 mol of methacryloxymethyl trimethoxysilane (silane a2) was condensed in presence of 0.4 mmol BHT in 80 ml ethyl acetate. A pale yellow liquid was obtained. Viscosity (25° C.): 18 Pa*s. $n^D_{20}$:1.475.

Example 5i

According to the general condensation procedure, 0.8 mol of (methacryloxymethyl)methyldimethoxysilane (sila(i a2) was condensed in presence of 0.4 mmol BHT in 80 ml ethyl acetate. A pale yellow liquid was obtained. Viscosity (25° C.): 3 Pa*s. $n^D_{20}$:1.462.

Example 5j

According to the general condensation procedure, 0.8 mol of 2-dimethoxydiphenylsilane (silane a3) was condensed in presence of 0.4 mmol BHT in 80 ml ethyl acetate. A pale yellow liquid eas obtained.

Example 5k

According to the general condensation procedure, 0.8 mol of 2-dimethoxyphenylmethylsilane (silane a3) was condensed in presence of 0.4 mmol BHT in 80 ml ethyl acetate. A pale yellow liquid was obtained.

Example 5l

According to the general condensation procedure, 0.8 mol of 9,9-dimethoxy-9H-9-silafluorene (silane a3) was condensed in presence of 0.4 mmol BHT in 80 ml ethyl acetate. A pale yellow liquid was obtained.

Example 5m

According to the general condensation procedure, 0.8 mol of dimethoxydi-1-naphthalenylsilane (silane a3) was condensed in presence of 0.4 mmol BHT in 80 ml ethyl acetate. A pale yellow liquid was obtained.

Example 6a

According to the general condensation procedure, 0.4 mol of γ-methacyloxypropyltrimethoxysilane (silane a2) and 0.4 mol of dimethoxydiphenylsilane (silane a3) were condensed in presence of 0.4 mmol BHT in 80 ml ethyl acetate. A pale yellow liquid was obtained. Viscosity (25° C.): 24 Pa*s. $n^D_{20}$:1.523.

Example 6b

According to the general condensation procedure, 0.4 mol of γ-methacyloxypropylmethyldimethoxysilane (silane a2) and 0.4 mol of dimethoxydiphenylsilane (silane a3) were condensed in presence of 0.4 mmol BHT in 80 ml ethyl acetate. A pale yellow liquid was obtained. Viscosity (25° C.): 2 Pa*s. $n^D_{20}$:1.534.

Example 6c

According to the general condensation procedure, 0.4 mol of methacryloxymethyl trimethoxysilane (silane a2) and 0.4 mol of dimethoxydiphenylsilane (silane a3) were condensed in presence of 0.4 mmol BHT in 80 ml ethyl acetate. A pale yellow liquid was obtained. Viscosity (25° C.): 3 Pa*s. $n^D_{20}$:1.546.

Example 6d

According to the general condensation procedure, 0.4 mol of methacryloxymethyl trimethoxysilane (silane a2) and 0.4 mol of dimethoxydi-1-naphthalenylsilane (silane a3) were condensed in presence of 0.4 mmol BHT in 80 ml ethyl acetate. A pale yellow liquid was obtained. Viscosity (25° C.): 4 Pa*s. $n^D_{20}$:1.565.

Example 6e

According to the general condensation procedure, 0.4 mol of 9,9-dimethoxy-4-oxo-5,10-dioxa-3-aza-9-silaundec-1-yl Methacrylate (silane a1) and 0.4 mol of methacryloxymethyl trimethoxysilane (silane a2) were condensed in presence of 0.4 mmol BHT in 80 ml ethyl acetate. A pale yellow liquid was obtained.

Example 7 (Condensable Filling Composites)

| Example | 7a | 7b | 7c | 7d |
|---|---|---|---|---|
| Polysiloxane (a1) | Example 5a 6.00 | Example 4a 18.00 | Ex. 6e 9.00 + | Example 5a 6.00 |
| Polysiloxane (a2) | Example 5f 6.00 | — | — | Ex. 6a 9.00 / Example 6a 12.00 |
| Polysiloxane (a3) | Example 5j 6.00 | — | — | — |
| Dental glass 1 | 14.00 | 14.00 | 14.00 | 14.00 |
| Dental glass 2 | 62.00 | 62.00 | 62.00 | 62.00 |
| Fumed $SiO_2$ | 5.00 | 5.00 | 5.00 | 5.00 |
| Nano-$SiO_2$ | — | — | — | — |
| CQ | 0.40 | 0.40 | 0.40 | 0.40 |
| DABE | 0.60 | 0.60 | 0.60 | 0.60 |
| FS [MPa] | 120.4 | 125.7 | 122.4 | 128.1 |
| MOE [GPa] | 9.9 | 10.2 | 10.1 | 10.8 |
| Shrinkage [%] | 1.72% | 1.62% | 1.62% | 1.55% |

| Example | 7e | 7f | 7g | 7h |
|---|---|---|---|---|
| Polysiloxane (a1) | Example 4a 18.00 | Example 5a 6.00 | Example 5a 6.00 | Example 4b 18.00 |
| Polysiloxane (a2) | — | Example 5f 6.00 | Example 6a 12.00 | — |
| Polysiloxane (a3) | — | Example 5j 6.00 | — | — |
| Dental glass 1 | 12.00 | 12.00 | 12.00 | 12.00 |
| Dental glass 2 | 56.00 | 56.00 | 56.00 | 56.00 |
| Fumed $SiO_2$ | — | — | — | — |
| Nano-$SiO_2$ | 13.00 | 13.00 | 13.00 | 13.00 |
| CQ | 0.40 | 0.40 | 0.40 | 0.40 |
| DABE | 0.60 | 0.60 | 0.60 | 0.60 |
| FS [MPa] | 142.5 | 130.4 | 138.1 | 135.6 |
| MOE [GPa] | 11.1 | 10.9 | 10.8 | 10.9 |
| Shrinkage [%] | 1.23% | 1.32% | 1.25% | 1.27% |

| Example | 7i | 7j | 7k | 7l |
|---|---|---|---|---|
| Polysiloxane (a1) | Example 4a 12.00 | Example 5a 4.00 | Example 5c 8.00 | Ex. 4a 12.25 + Ex. 5a 3.25 |
| Polysiloxane (a2) | — | Example 5f 4.00 | Example 6d 10.00 | Ex. 6d 2.25 |
| Polysiloxane (a3) | — | Example 5j 4.00 | — | — |
| BisGMA | 4.00 | 4.00 | — | — |
| TEGDMA | 2.00 | 2.00 | — | — |
| Dental glass 1 | 14.00 | 14.00 | 12.00 | 11.30 |
| Dental glass 2 | 62.00 | 62.00 | 56.00 | 56.55 |
| Fumed $SiO_2$ | 5.00 | 5.00 | — | — |
| Nano-$SiO_2$ | — | — | 13.00 | 13.40 |
| CQ | 0.40 | 0.40 | 0.40 | 0.40 |
| DABE | 0.60 | 0.60 | 0.60 | 0.60 |
| FS [MPa] | 121.3 | 118.7 | 132.5 | 142.5 |
| MOE [GPa] | 10.4 | 10.1 | 11.2 | 11.6 |
| Shrinkage [%] | 1.72% | 1.83% | 1.24% | 1.21% |

| Example | 7m | 7n | 7o | 7p |
|---|---|---|---|---|
| Polysiloxane (a1) | Example 4d 17.70 | Example 5e 7.60 | Example 5e 6.00 | Ex. 4d 12.25 + Ex. 4a 5.45 |
| Polysiloxane (a2) | — | Example 6a 9.90 | Example 5f 6.00 | — |
| Polysiloxane (a3) | — | — | Example 5j 6.00 | — |
| Dental glass 1 | 11.30 | 11.30 | 11.30 | 11.30 |
| Dental glass 2 | 56.60 | 56.80 | 56.30 | 56.60 |
| Fumed $SiO_2$ | 0.50 | 0.50 | 0.50 | 0.50 |
| Nano-$SiO_2$ | 13.40 | 13.40 | 13.40 | 13.40 |
| CQ | 0.20 | 0.20 | 0.20 | 0.20 |
| DABE | 0.30 | 0.30 | 0.30 | 0.30 |
| FS [MPa] | 146.3 | 145.8 | 141.7 | 147.3 |
| MOE [GPa] | 12.2 | 12.1 | 11.5 | 12.5 |
| Shrinkage [%] | 1.13% | 1.16% | 1.26% | 1.21% |

Example 8(Flowable Filling Composites)

| Example | 8a | 8b | 8c | 8d |
|---|---|---|---|---|
| Polysiloxane (a1) | — | — | Example 5a 11.00 | Example 5a 11.00 |
| Polysiloxane (a2) | Example 4a 35.00 | Example 4b 35.00 | Example 5f 14.00 | Example 6a 21.00 |
| Polysiloxane (a3) | — | — | Example 5j 7.00 | — |
| Dental glass 1 | 10.00 | 10.00 | 10.50 | 10.50 |
| Dental glass 2 | 43.00 | 43.00 | 45.50 | 45.50 |
| Fumed $SiO_2$ | — | — | — | — |
| Nano-$SiO_2$ | 11.00 | 11.00 | 11.00 | 11.00 |
| CQ | 0.40 | 0.40 | 0.40 | 0.40 |
| DABE | 0.60 | 0.60 | 0.60 | 0.60 |
| FS [MPa] | 118.3 | 116.8 | 121.0 | 123.1 |
| MOE [GPa] | 7.2 | 6.9 | 7.5 | 7.7 |
| Shrinkage [%] | 2.49% | 2.38% | 2.31% | 2.28% |

Example 9(Dual-Curing Core Buildup Materials)

| Example | 9a | 9b |
|---|---|---|
| Polysiloxane (a1) | Example 5a 11.00 | Example 5a 11.00 |
| Polysiloxane (a2) | Example 4a 35.00 / Example 4a 35.00 | Example 5f 14.00 / Example 5f 14.00 |
| Polysiloxane (a3) | Example 5j 7.00 | Example 5j 7.00 |
| Dental glass 1 | 10.00 / 10.00 | 10.50 / 10.50 |
| Dental glass 2 | 43.00 / 43.00 | 45.50 / 45.50 |
| Fumed $SiO_2$ | 3.00 / 3.00 | 3.00 / 3.00 |
| Nano-$SiO_2$ | 8.00 / 8.00 | 8.00 / 8.00 |
| DEPT | 0.60 / — | 0.60 / — |
| BPO | — / 1.00 | — / 1.00 |
| BHT | — / 0.05 | — / 0.05 |
| CQ | 0.15 / — | 0.15 / — |
| DABE | 0.25 / — | 0.25 / — |
| FS [MPa] | 112.3 | 118.6 |
| MOE [GPa] | 6.5 | 6.9 |
| Shrinkage [%] | 2.53% | 2.41% |

Example 10 (Dual-Curing Luting Material)

| Example | 10a | 10b |
|---|---|---|
| Polysiloxane (a1) | Example 5a 11.00 | Example 5a 8.25 |
| Polysiloxane (a2) | Example 4a 35.00 / Example 4a 27.00 | Example 5f 14.00 / Example 5f 10.50 |
| Polysiloxane (a3) | Example 5j 7.00 | Example 5j 5.25 |
| MDP | — / 9.00 | — / 9.00 |
| Dental glass 1 | 9.60 / 9.50 | 10.10 / 10.00 |
| Dental glass 2 | 43.00 / 42.50 | 45.50 / 45.00 |
| Fumed $SiO_2$ | 3.00 / 3.00 | 3.00 / 3.00 |
| Nano-$SiO_2$ | 8.00 / 8.00 | 8.00 / 8.00 |
| DEPT | 0.60 / — | 0.60 / — |
| NTPB | 0.40 / — | 0.40 / — |
| BPO | — / 0.95 | — / 0.95 |
| BHT | — / 0.05 | — / 0.05 |
| CQ | 0.15 / — | 0.15 / — |
| DABE | 0.25 / — | 0.25 / — |
| FS [MPa] | 111.5 | 117.7 |
| MOE [GPa] | 6.3 | 6.8 |
| Shrinkage [%] | 2.58% | 2.43% |

Flexural strength (FS): The flexural strength was determined in accordance with ISO 4049. All the materials were light-cured with a Celalux 2 lamp (VOCO GmbH) section by section for 40 seconds. The flexural strength was determined at a cross-head speed of 0.75 mm/min on a Zwick universal tester (Zwick GmbH & Co. KG, Ulm).

Modulus of elasticity (MOE): The modulus of elasticity was determined from the slope in the elastic range of the stress-strain curves from the flexural strength measurements.

Shrinkage: Shrinkage was determined by the bonded-disk method of Watts et al. (Watts D C, Cash A J, Determination of polymerization kinetics in visible-light cured materials: Methods development, *Dent Mater* 1991; 7: 281-287). Deviating from this, exposure was effected with a Celalux 2 lamp (VOCO GmbH) for 40 seconds per measurement.

Viscosity: The viscosity was determined by means of a rheometer (Physica MCR 301) from Anton Paar (Graz, Austria). The measurement was effected at 25° C. in a rotation experiment with plate/plate arrangement (diameter 25 mm, gap 1 mm) in a shear rate range from $10^{-2}$ to $10$ $s^{-1}$. For each measurement, 16 measured values were recorded within an interval of 30 seconds per shear rate. The tables each state the viscosities for the shear rates of $10$ $s^{-1}$.

Since the filler phase of a dental composite material is of decisive importance for its mechanical properties, it is essential for a meaningful and reliable comparison of mechanical properties to always compare only those products which have a similar filler content and a similar filler composition. The product categories above compared concerning their mechanical properties correspond to this requirement, since there was distinguished for example between condensable or highly viscous (i.e. highly filled) and flowable (i.e. medium filled) composites (for the different filler quantities, we refer to our comments on Component (B)). Furthermore, terms such as "hybrid composite", "micro hybrid", "nano hybrid", "microfilled composites" or "fibre-reinforced composite" provide information on the type of filler composition and thus also indirectly provide information on the quantities of added fillers. Thus microfilled composites consist of (fumed) silica in their filler phase. Due to its high thixotropy this product category can only contain a medium amount of filler. The hybrid composites are composed of different glasses with different size fractions (from 10 μm to <1 μm) in combination with silica. The hybrid composites have been established as dental universal composites that can be used for almost all dental restorations, from large incisal reconstructions to fillings that support masticatory forces in the posterior region. A further variant of a hybrid composite is the "nanohybrid type". Here are nanoscale, mainly non-aggregated and non-agglomerated fillers integrated into the filler phase. The incorporation of surface-modified nanoparticles thus enables an increase in the filler content without a corresponding increase in the viscosity of the composite. This should further improve the mechanical properties.

Our example composites 7a to 7d correspond to a typical hybrid composite that have a bimodal glass particle distribution as macroscopic filler component. The filler amount of the composite is approximately 81% by weight.

To ensure a reliable comparison of the mechanical values of the polymerizable dental compositions based on condensed silanes according to the invention with corresponding values of composites from the literature, not only the systems have to be comparable but also the measurements performed must be identical. Especially the standard DIN EN ISO 4049 stipulates that the cured test specimens must be stored in deionised water at 37° C. for a period of 24 hours after demolding before the mechanical properties are determined. This step of water storage is not considered in many tests of the mechanical properties of dental polymerizable compositions based on condensed silanes. Thus, systematically higher values are obtained.

In DE 198 60 364 C2, entitled "Polymerisierbare Dentalmassen auf Basis von zur Aushartung befahigten Siloxanverbindungen, deren Verwendung und Herstellung" ("Polymerisable Materials Which Are Based on Hardenable Siloxane Compounds"), in examples 3 and 5, the condensed silane 1,3,5,7-tetramethyl-1,3,5,7-tetrakis-(3-methacryloxypropyl)-cyclotetrasiloxane is cured as main monomer component by the initiator system camphorquinone/amine and an inorganic filler amount of approximately 80% by weight. In example 3 the classical dental monomer UDMA (7,7,9-trimethyl-3,14-dioxa-4,13-dioxo-5,12-diazahexadecan-1, 16-diol dimethacrylate) and in example 5 the classical dental monomer bis-GMA (2,2-bis-4-(3-hydroxypropoxyphenyl) propane dimethacrylate) complete the monomer matrix.

These composites should be comparable with the composites according to the invention, although the classical, proven dental monomers are here additionally used supporting the polysiloxanes. In examples 3 and 5 the amount of the polysiloxanes is higher than the amount of the standard monomers.

Composite 3 of DE 198 60 364 C2 has a flexural strength of 119 MPa, a modulus of elasticity of 8731 MPa and a volume shrinkage of 2.73%.

Composite 5 of DE 198 60 364 C2 has a flexural strength of 115 MPa, a modulus of elasticity of 8713 MPa and a volume shrinkage of 2.67%.

In DE 198 60 361 A1, entitled "Vernetzbare Monomere auf Cyclosiloxanbasis, deren Herstellung und deren Verwendung in polymerisierbaren Massen" are also disclosed polymerizable dental compositions based on co- and homocondensates of silanes having a filler amount of approximately 80% by weight and with the initiator system camphorquinone/amine. Consideration is given to compositions in which the quantity of polysiloxane is at least of the same order of magnitude as that of conventional dental monomers.

Example 3 of DE 198 60 361 A1 discloses a dental composite consisting of the differently condensed 1-(trimethoxysilylethyl)-3,5,7-tris(3-methacryloxypropyl)-1,3,5,7-tetramethyltetra siloxane, the cocondensate of 1-(trimethoxysilylethyl)-3,5,7-tris(3-methacryloxypropyl)-1,3,5,7-tetramethyltetrasiloxane and tetramethoxysilane, the classical dental monomer UDMA (7,7,9-trimethyl-3,14-dioxa-4,13-dioxo-5,12-diazahexadecan-1,16-diol dimethacrylate) in small surplus compared to the condensed silanes, fillers in an amount of approximately 82% by weight, and also the photoinitiator system camphorquinone/amine.

Composite 3 of DE 198 60 361 A1 has a flexural strength of 107 MPa, a modulus of elasticity of 7317 MPa and a volume shrinkage of 2.57%.

Example 5 of DE 198 60 361 A1 discloses a dental composite containing the homocondensate 1-(trimethoxysilylethyl)-3,5,7-tris(3-methacryloxypropyl)-1,3,5,7-tetramethyltetrasiloxane, the cocondensate of 1-(trimethoxysilylethyl)-3,5,7-tris(3-methacryloxypropyl)-1,3,5,7-tetramethyltetrasiloxane with bis-(hydroxymethyl)-tricyclo[5.2.1.0$^{2,6}$]decane-methacrylate-(3-trimethoxysilyl-1-carbamate), the classical dental monomers bis-GMA (2,2-bis-4-(2-hydroxypropoxyphenyl)propane dimethacrylate) and bis(acryloyloxymethyl)tricyclo[5.2.1.0$^{2,6}$]decane as monomer matrix, a filler amount of approximately 80% by weight and the photoinitiator system camphorquinone/amine.

Composite 5 of DE 198 60 361 A1 has a flexural strength of 121 MPa, a modulus of elasticity of 8132 MPa and a volume shrinkage of 2.29%.

Example 6 of DE 198 60 361 A1 discloses a dental composite containing the homocondensate 1-(trimethoxysilylethyl)-3,5,7-tris(3-methacryloxypropyl)-1,3,5,7-tetramethyltetrasiloxane, the cocondensate of 1-(trimethoxysilylethyl)-3,5,7-tris(3-methacryloxypropyl)-1,3,5,7-tetramethyltetrasiloxane and tetramethoxysilane, the cocondensate of 1-(trimethoxysilylethyl)-3,5,7-tris(3-methacryloxypropyl)-1,3,5,7-tetramethyltetrasiloxane with 2,2-bis-(4-hydroxyphenyl)propane-4-methacrylate-4'-(3-trimethoxysilyl-1-carbamate), the classical dental monomers bis-GMA (2,2-bis-4-(3-hydroxypropoxyphenyl)propane dimethacrylate), 2,2-bis-4-(2-hydroxyethoxyphenyl)propane dimethacrylate), bis(acryloyloxymethyl)tricyclo[5.2.1.0$^2$,6]decane as monomer matrix, filler amount of 80.8% by weight and the photoinitiator system camphorquinone/amine.

Composite 6 of DE 198 60 361 A1 has a flexural strength of 117 MPa, a modulus of elasticity of 8615 MPa and a volume shrinkage of 2.51%.

Example 8 of DE 198 60 361 A1 discloses a dental composite containing the homocondensate 1-(trimethoxysilylethyl)-3,5,7-tris(3-methacryloxypropyl)-1,3,5,7-tetramethyltetrasiloxane, the cocondensate of 1-(trimethoxysilylethyl)-3,5,7-tris(3-methacryloxypropyl)-1,3,5,7-tetramethyltetrasiloxane mit 2,2-bis-(4-hydroxyphenyl)-propane-4-methacrylate-4'-(3-trimethoxysilyl-1-carbamate), and also the classical dental monomer UDMA (7,7,9-trimethyl-3,14-dioxa-4,13-dioxo-5,12-diazahexadecan-1,16-diol dimethacrylate) as monomer matrix, filler amount of approximately 80% by weight and the photoinitiator system camphorquinone/amine.

Composite 8 of DE 198 60 361 A1 has a flexural strength of 116 MPa, a modulus of elasticity of 7513 MPa and a volume shrinkage of 2.19%.

Example 9 of DE 198 60 361 A1 discloses a dental composite containing the differently condensed 1-(trimethoxysilylethyl)-3,5,7-tris(3-methacryloxypropyl)-1,3,5,7-tetramethyltetra-siloxane, the cocondensate of 1-(trimethoxysilylethyl)-3,5,7-tris(3-methacryloxypropyl)-1,3,5,7-tetramethyltetrasiloxane and tetramethoxysilane, the cocondensate of 1-(trimethoxysilylethyl)-3,5,7-tris(3-methacryloxypropyl)-1,3,5,7-tetramethyltetrasiloxane with 2,2-bis-(4-hydroxyphenyl)-propane-4-methacrylate-4'-(3-trimethoxysilyl-1-carbamate), and also the classical dental monomers bis-GMA (2,2-bis-4-(2-hydroxypropoxyphenyl)propane dimethacrylate) UDMA (7,7,9-trimethyl-3,14-dioxa-4,13-dioxo-5,12-diazahexadecan-1,16-diol dimethacrylate) and bis(acryloyloxymethyl)tricyclo[5.2.1.0$^{2,6}$]decane as monomer matrix, filler amount of 80% by weight and the photoinitiator system camphorquinone/amine.

Composite 9 of DE 198 60 361 A1 has a flexural strength of 117 MPa, a modulus of elasticity of 7916 MPa and a volume shrinkage of 2.24%.

In the DE 41 33 494 A1, entitled "Dentalharzmassen" chemically, thermally or photochemically curing dental resin compositions based on polymerizable polysiloxanes, processes for their production and their use for production of pasty, curable dental materials obtainable by hydrolytic condensation of one or more hydrolytically condensable silanes are disclosed. In this document the systems are both free-radically and cationically polymerized.

The composite system L1 of DE 41 33 494 A1 (example 16, page 27) consists of a resin system, which is obtained by reaction of trimethylolpropane triacrylate (TMPTA) and (mercaptomethyl)methyldiethoxysilane in a molar ratio of 1.2 to 1 to give the corresponding Michael adduct. The ethoxy groups of the adduct are hydrolysed under normal acidic conditions to a transparent resin, then condensed and finally silanized with trimethylchlorosilane to convert free Si—OH groups and thus to reduce the viscosity of the resin phase to achieve a higher filler amount in the composite. A dental hybrid composite with a filler amount of 75% by weight is obtained from the resin, which is then mixed with a photoinitiator and as mono-component is free-radically cured.

The composite L1 of DE 41 33 494 A1 has a flexural strength (here referred to as fracture strength, whereby the test bars were not stored in water before the test) of 120 MPa, a modulus of elasticity of 8000 MPa and a volume shrinkage of 2.9% (see table, page 28).

Example 18 of DE 41 33 494 A1 discloses a dental composite composition of a two-component dental paste/paste system, that cures chemically by means of the redox system BPO (benzoyl peroxide)/amine (N,N-bis-(2-hydroxyethyl)-p-toluidine). The resin mixture of the hybrid composite comprises—as above—the product of the reaction of trimethylolpropane triacrylate (TMPTA) and (mercaptomethyl)methyldiethoxysilane in a molar ratio of 1.2 to 1, but in this case the resulting Michael adduct is not silanized. Correspondingly the viscosity of the obtained resin is higher. The hybrid composite contains in addition to the silane condensate also the classic dental monomer "2,2-bis-[4'-(2'-methacroylethoxy)phenyl]propane", an ethoxylated bisphenol A dimethacrylate and also a filler amount of 76% by weight. The flexural strength of the not water-stored test specimens is 120 MPa and the volume shrinkage is 2.3%.

In DE 199 03 177 A1, entitled "Dentalmaterialien auf der Basis von Polysiloxanen" dental materials which comprise at least one polysiloxane based on one or more hydrolytically condensable silane(s) of a specific structure are disclosed. The dental material can additionally contain further ionically and/or free-radically polymerizable monomers.

Example 7 of DE 199 03 177 A1 discloses a pasty dental cement in form of a hybrid composite comprising a polysiloxane in an amount of 31.6% by weight, that was obtained after hydrolytic condensation and subsequent silylation of bis(methacryloylethoxycarbonylethyl)-[3-(triethoxysilyl-propyl)]amine (obtained from the Michael addition of 3-amininopropyltriethoxysilane and 2-acryloyloxyethyl methacrylate), UDMA (7,7,9-trimethyl-3,14-dioxa-4,13-dioxo-5,12-diazahexadecan-1,16-diol dimethacrylate) in an amount of 7.8% by weight, silanized fumed silica in an amount of 41.1% by weight, ytterbium fluoride in an amount of 18.7% by weight and the photoinitiator mixture "camphorquinone/amine" in an amount of 0.5% by weight. The flexural strength of the dental composite is 62 MPa, the modulus of elasticity is 3260 MPa and the volume shrinkage is 3.6%.

In DE 101 02 297 A1, entitled "Dentalmaterialien auf der Basis von Metalloxid-Clustern" the dental materials described above are further improved mechanically by the use of clusters.

In composition K-1 of DE 101 02 297 A1, like above, a polysiloxane is used that is obtained after hydrolytic condensation of bis(methacryloylethoxycarbonylethyl)-[3-(triethoxysilylpropyl)]amine and was not sylated. This photoinitiated polysiloxane is processed into a paste in a hybrid composite in an amount of 25% by weight with filler in an amount of 75% by weight (fumed silica in an amount of 1% by weight, ytterbium fluoride in an amount of 15% by weight, spherosil in an amount of 15% by weight and glass in an amount of 44% by weight) and cured according to DIN EN ISO 4049. The flexural strength of the dental composite K-1 is 68 MPa, the modulus of elasticity is 5500 MPa.

In composition K-3 of DE 101 02 297 A1, a polysiloxane is used that after hydrolytic condensation of the photoinitiated (3-triethoxysilylpropylaminocarbonyl) butyric acid-(1,3-(2)-bismethacryloyloxypropyl)ester in a hybrid composite in an amount of 25% by weight with 75% by weight of the above specified filler mixture, is processed into a paste and cured according to DIN EN ISO 4049. The polysiloxane was obtained from 3-aminopropyl-triethoxysilane and the adduct of glycerol dimethacrylate and glutaric acid anhydride with amide bonding.

As photoinitiator of the composition it was used a mixture of camphorquinonein an amount of 0.3% by weight, 0.6% by weight of 4-(N,N-dimethylamino)-benzoic acid ethyl ester and 0.4% by weight of acylphosphine oxide, wherein the weights are based on the total composition.

The flexural strength of the dental composite K-3 of DE 101 02 297 A1 is 89 MPa, the modulus of elasticity is 7160 MPa.

Due to the higher filler amount the mechanical values of the dental hybrid composite are little higher in this publication than in the DE 199 03 177 A1 mentioned above.

In the DE 101 02 297 A1 the mechanical strength of polymerizable dental compositions based on condensed silanes should be improved by the addition of certain clusters of the type $Zr_4O_2(OMc)_{12}$ and lead to an increase in the modulus of elasticity of the materials.

If 10% by weight of the monomer matrix from K-1 of DE 101 02 297 A1 is substituted with the cluster type $Zr_4O_2(OMc)_{12}$, then K-2 of DE 101 02 297 A1 is formed, which has flexural strength of 100 MPa and modulus of elasticity of 9300 MPa.

If 10% by weight of the monomer matrix from K-3 of DE 101 02 297 A1 is substituted with the cluster type $Zr_4O_2(OMc)_{12}$, then K-4 of DE 101 02 297 A1 is formed, which has a flexural strength of 110 MPa and a modulus of elasticity of 9750 MPa.

If 20% by weight of the monomer matrix from K-3 of DE 101 02 297 A1 is substituted with the cluster type $Zr_4O_2(OMc)_{12}$, then K-5 of DE 101 02 297 A1 is formed, which has a flexural strength of 113 MPa and a modulus of elasticity of 10900 MPa.

In the DE 10 2006 016 474 A1, entitled "Dentalmaterialien enthaltend hydrophobe, nanopartikuläre Kieselsäurecokondensate und deren Verwendung" dental composite materials based on polysiloxane with additionally liquid, functionalized cocondensates of silicic acid tetraalkyl esters with functionalized trialkoxysilanes are disclosed. The presence of these cocondensates, whose end groups are reacted with trimethylsilyl groups, should improve the mechanical properties of the composites.

In the dental hybrid composite material A of DE 10 2006 016 474 A1, the hydrolytic condensate of the silane (1,3-dimethacryloyloxypropyl-[4-(3-triethoxysilyl)propyl-N-methylaminocarbonyl)]butyrate, which is obtained by reaction of glycerol dimethacrylate with glutaric acid anhydride, is in an amount of 29.8% by weight with the photoinitiator system "camphorquinone/p-dimethylaminobenzoic acid ethyl ester" in an amount of 0.2% by weight and a filler phase of ytterbium fluoride (12.7% by weight), fumed silica (0.9% by weight), barium aluminium borosilicate glass filler (44.1% by weight) and a silica-zirconia mixed oxide (12.3% by weight) in an total filler amount of 70% by weight based on the total composition processed into a paste and cured. The flexural strength is 51 MPa and the modulus of elasticity is 5410 MPa.

If a proportion of 5.9% by weight of the polysiloxane from composite A of DE 10 2006 016 474 A1 is substituted with the additional low viscosity cocondensate of tetraethoxysilane with 3-methacryloxypropyltriethoxysilane and end group reaction with trimethylchlorosilane, then composite B of DE 10 2006 016 474 A1 is formed, which has a flexural strength of 75 MPa and a modulus of elasticity of 5240 MPa.
Mechanical Values (Prior Art)

| Patent | Resin/Filler | Flexural strength (MPa) | MOE (MPa) | Shrinkage (%) |
|---|---|---|---|---|
| DE 19 860 364 C2 | | | | |
| Example 3 | 20/80 | 119 | 8731 | 2.7 |
| Example 5 | 20/80 | 115 | 8713 | 3.3 |
| DE 19 860 361 A1 | | | | |
| Example 3 | 20/80 | 107 | 7317 | 2.6 |
| Example 5 | 20/80 | 121 | 8132 | 2.3 |
| Example 6 | 19/81 | 117 | 8615 | 2.5 |
| Example 8 | 20/80 | 116 | 7513 | 2.2 |
| Example 9 | 20/80 | 117 | 7916 | 2.2 |
| DE 41 33 494 A1 | | | | |
| Example 16 | 25/75 | 120 | 8000 | 2.9 |
| Example 18 | 24/76 | 120 | — | 2.3 |
| DE 19 903 177 A1 | | | | |
| Example 7 | 40/60 | 62 | 3260 | 3.6 |
| DE 10102297 A1 | | | | |
| K1 | 25/75 | 68 | 5500 | — |
| K3 | 25/75 | 89 | 7160 | — |
| K2 | 25/75 | 100 | 9300 | — |
| K4 | 25/75 | 110 | 9750 | — |
| K5 | 25/75 | 113 | 10900 | — |
| DE 10 2006 016 474 A1 | | | | |
| A | 30/70 | 51 | 5410 | — |
| B | 30/70 | 75 | 5240 | — |

The comparison between the clinically relevant values of the compositions according to the invention and the corresponding values of the state of literature shows a clear superiority of the novel systems based on the condensed silanes according to the invention. Considering the improvement of these values in the order of the literature data from 2009 and 2018 (see above), the values of comparable inventive dental compositions of the "hybrid composite" type reach new highs, even exceeding the values of fibre reinforced composites from the current composition of Rosentritt, Illie and Lohbauer from 2018. Additionally due to the extremely low shrinkage only a very small change of the density during the transition from the liquid/pasty phase into the solid phase is induced, so that an especially advantageous curing depth can be reached.

What is claimed is:

1. A polymerizable dental composition comprising:
   (A) polysiloxanes, wherein the polysiloxanes comprise i) a mixture of the condensates of silanes (a1), (a2) and (a3), ii) a cocondensate of a mixture of silanes (a1), (a2) and (a3), iii) a mixture of at least two of the cocondensates (a1)/(a2), (a1)/(a3) and (a2)/(a3), iv) a mixture of the condensate of one of the three silanes (a1), (a2) or (a3) with the cocondesnate of the other two silanes, or v) combinations thereof,
   wherein silane (a1) has the formula $(R^1O)_aR^2_bSi[—A(—Y\{—B[—PG]_f\}_e)_d]_c$, wherein
   $Y=—(X)_x—C(=O)NH—$, $—NHC(=O)—(X)_x—$ and $—(X)_xC(=O)N(—C(=O)NH—)—$, $—C(=O)NHC(=O)NH—$, $—NHC(=O)NHC(=O)—$,
   wherein the bond arranged on the left in each formula is closer to the structural element A and the bond arranged to the right is closer to the structural element B,
   PG=polymerizable group,
   A=an organic linking group, connecting Si with Y and comprising 1 to 20 C-atoms,
   B an organic linking group, connecting Y with PG and comprising 1 to 20 C-atoms,
   X=O, S, or NH,
   $R^1$=H or C1- to C4-alkyl,
   $R^2$=C1- to C4-alkyl,
   a=2 or 3,
   b=0 or 1,
   c=1 or 2,
   d=1 to 3,
   e=1 or 2,
   f=1 to 5,
   a+b+c=4, and
   x=0 or 1,
   and wherein silane (a2) has the formula $(R^1O)_aR^2_bSi[—A'(—PG)_f]_c$, wherein
   PG=polymerizable group,
   A'=an organic linking group, connecting Si with PG, and comprising 1 to 20 C-atoms, wherein A' is not $—C(=O)NH—$, $—NHC(=O)—$, $—OC(=O)NH—$, $—NHC(=O)O—$, $—SC(=O)NH—$, $—NHC(=O)S—$, $—NHC(=O)NH—$, $—OC(=O)N(—C(=O)NH—)—$, $—SC(=O)N(—C(=O)NH—)—$, $—NHC(=O)N(—C(=O)NH—)—$, $—C(=O)NHC(=O)NH—$, or $—NHC(=O)NHC(=O)—$,
   $R^1$=H or C1- to C4-alkyl,
   $R^2$=C1- to C4-alkyl,
   a=2 or 3,
   b=0 or 1,
   c=1 or 2,
   f=1 to 5, and
   a+b+c=4,
   and wherein silane (a3) has the formula $(R^1O)_aR^2_bSiAr_c$, wherein
   $R^1$=H or C1- to C4-alkyl,
   $R^2$=C1- to C4-alkyl,
   Ar=aryl wherein different Ar groups may be the same or different,
   a=2 or 3,
   b=0 or 1,
   c=1 or 2,
   a+b+c=4,
   (B) fillers, and
   (C) initiators, catalysts, activators, or combinations thereof, for polymerization.

2. The polymerizable dental composition as claimed in claim 1, comprising at least one component selected from the group consisting of:
   (D) organic, polymerizable monomers, which are not component (A) polysiloxanes,
   (E) organic monomers containing acid groups without any Si-atom,
   (F) additives,
   (G) solvents,
   and combinations thereof.

3. The polymerizable dental composition as claimed in claim 2, wherein the component (D)organic, polymerizable monomers, which are not component (A) polysiloxanes, is selected from the group consisting of:

monofunctional or polyfunctional (meth)acrylate monomers, from esters of (meth)acrylic acid with alkyl groups of 1 to 12 carbon atoms and esters of (meth)acrylic acid containing aromatic groups having 6 to 12 carbon atoms, wherein the alkyl groups and aromatic groups that form the esters may contain substituents selected from the group consisting of hydroxyl groups and ether bonds, polymerizable monomers that are hydroxyl compounds having at least one ethylenic double bond, polyfunctional (meth)acrylate monomers selected from the group consisting of di(meth)acrylates of alkylene glycol having 2 to 20 carbon atoms, di(meth)acrylates of oligomers of alkylene glycols, polyalkylene glycol di(meth)acrylate, and di(meth)acrylates of bisphenol A or of the diglycidyl ether of bisphenol A, polymerizable compounds based on a central polyalicyclic structural element selected from the group consisting of:
3(4),8(9)-bis((meth)acryloyloxymethyl)tricyclo[5.2.1.0$^{2,6}$]decane, alkoxylated 3(4),8(9)-bis((meth)acryloyl-oxymethyl)tricyclo[5.2.1.0$^{2,6}$]decane, 2,3-bis((meth)-acryloyloxymethyl)bicyclo[2.2.1]heptane, alkoxylated 2,3-bis((meth)acryloyloxymethyl)bicyclo[2.2.1]heptane, 1,3,5-tri(meth)acryloyloxytricyclo[3.3.1.1$^{3,7}$]decane, alkoxylated tri(meth)acryloyloxytricyclo[3.3.1.1$^{3,7}$]-decane, and (meth)acrylates of tricyclo[5.2.1.0$^{2,6}$]-decane-3(4),8(9)-dimethanol, alkoxylated tricyclo-[5.2.1.0$^{2,6}$]decane-3(4),8(9)-dimethanol, bicyclo[2.2.1]-heptane-2,3-dimethanol, alkoxylated bicyclo[2.2.1]-heptane-2,3-dimethanol, 1,3,5-adamantanetriol, alkoxylated 1,3,5-adamantanetriol, with urethane, urea, amide, allophanate, acylurea or biuret groups arranged between the polyalicyclic structural element and the (meth)acrylates, urethane (meth)acrylates that are reaction products formed from 2 moles of a (meth)acrylate with a hydroxyl group and one mole of a diisocyanate, and ethylene glycol di (meth)acrylate, diethylene glycol di (meth)acrylate, hexane-1,6-diol di (meth)acrylate (HEDMA), triethyl ene glycol di (meth)acrylate (TEGDMA), dodecane-1,12-diol di(meth)acrylate, bisphenol A di(meth)acrylate, alkoxylated bisphenol A di(meth)acrylate, bisphenol B di(meth)acrylate, alkoxylated bisphenol B di(meth)acrylate, bisphenol C di(meth)acrylate, alkoxylated bisphenol C di(meth)acrylate, bisphenol F di (meth)acrylate, alkoxylated bisphenol F di(meth)acrylate, polyethylene glycol di (meth)acrylate, 7,7, 9-trimethyl-3, 14-dioxa-4, 13-dioxo-5,12-diazahexadecan-1,16-diol dimethacrylate (UDMA), butanedioldi(meth)acrylate, tetraethylene glycoldi (meth)acrylate, neopentyl glycol di (meth)acrylate, 2-hydroxypropyl 1,3-di (meth)acrylate, 3-hydroxypropyl 1, 2-di (meth)acrylate, pentaerythritol di (meth)acrylate, di (meth)acrylate s of dihydroxymethyltricyclo[5 0.2.0$^{2,6}$]decane, 2-hydroxy-ethyl (meth)acrylate, 2-hydroxypropyl (meth)acrylate, 3-hydroxypropyl (meth)acrylate, 1, 2-dihydroxypropyl (meth)acrylate, 1,3-dihydroxypropyl (meth)acrylate, 2,3-dihydroxypropyl (meth)acrylate, 2,2-bis-4-(2-hydroxypropoxyphenyl)propane dimethacrylate (bis-GMA), trimethylolpropane tri (meth)acrylate, trimethylolethane tri (meth)acrylate, pentaerythritol tri (meth)acrylate, trimethylolmethane tri (meth)acrylate, pentaerythritol tetra(meth)acrylate, dimethylolpropane tetra(meth)acrylate, pentaerythritol hexa(meth)acrylate, butyleneglycol di (meth)acrylate, propyleneglycol di (meth)acrylate, nonanediol di (meth)acrylate, decanediol di (meth)acrylate, glycerol mono(meth)acrylate, glycerol di (meth)acrylate, trimethylolpropane mono(meth)acrylate, trimethylol-propane di(meth)acrylate, sorbitol mono-, di-, tri-, tetra- or penta (meth)acrylate, methyl (meth)acrylate, ethyl (meth)acrylate, propyl (meth)acrylate, butyl (meth)acrylate, hexyl (meth)acrylate, tetrahydro-furfuryl (meth)acrylate, lauryl (meth)acrylate, cyclohexyl (meth)acrylate, allyl (meth)acrylate, glycidyl (meth)acrylate, 2-ethoxy ethyl (meth)acrylate, methoxy polyethylene glycol (meth)acrylate, isobornyl (meth)acrylate, 2-(N,N-dimethyl amino)ethyl (meth)acrylate, N-methylol (meth)acrylamide, diacetone-(meth)acrylamide, 2,2-bis [4-(meth)acryloyloxyphenyl]propane, 2-bis [4-(meth)acryloyloxyethoxyphenyl]propane, 2, 2-bis [4-(meth)acryloyloxydiethoxyphenyl] propane, 2,2-bis [4-(meth)acryloyloxytriethoxyphenyl]propane, 2,2-bis [4-(meth)acryloyloxytetraethoxyphenyl] propane, 2,2-bis [4-(meth)acryloyloxypentaethoxyphenyl] propane, 2,2-bis [4-(meth)acryloyloxydipropoxyphenyl]2,2-bis [4-(meth)acryloyloxyethoxyphenyl]-244-(meth)acryloyloxydiethoxyphenyl] propane, 2-[4-(meth)-acryloyloxy diethoxyphenyl]-2-[4-(meth)acryloyloxytriethoxyphenyl] propane, 2-[4-(meth)acryloyloxydipropoxy-phenyl]-2-[4-(meth)acryloyloxytriethoxyphenyl]propane, 2,2-bis [4-(meth)acryloyloxyisopropoxyphenyl]propane, neopentylglycolhydroxypivalate di(meth)acrylate, aceto-acetatoxyethyl (meth)acrylate, polypropylene glycol di(meth)acrylate, glycerol alkoxylate dimethacrylate, neopentyl glycol (meth)acrylate, N,N-(1,2-dihydroxyethylene)bisacrylamide, 2,2-bis [4-(meth)acryloyloxypentaethoxyphenyl] propane, 2,2-bis[4-(meth)acryloyloxypolyethoxyphenyl]propane, diethylene glycol di(meth)acrylate, dipentaerythritol tetra(meth)acrylate, dipentaerythritol hexa(meth)acrylate, N,N-(2,2,4-trim ethyl hexamethyl ene)bis [2-(aminocarboxy)-propane-1,3-di ol] tetra(meth)acrylate, the condensation product of 3-(4)-(meth)acryloyloxymethyl-8,(9)-hydroxymethyltricyclo[5.2.1.0$^{2,6}$]decane with dicarboxylic acids, 2-ethylhexyl (meth)acrylate, tridecyl (meth)acrylate, stearyl (meth)acrylate, benzyl (meth)acrylate, methoxy diethylene glycol (meth)acrylate, dicyclopentenyl (meth)acrylate, phenyl (meth)acrylate, pentaerythritol mono(meth)acrylate, dipentaerythritol mono(meth)-acrylate, and caprolactone-modified tetrahydrofurfuryl (meth)acrylate.

4. The polymerizable dental composition as claimed in claim 2, wherein the component (E) organic monomers containing acid group, without Si atom are selected from the group consisting of:

10-(meth)acryloyloxydecyl dihydrogen phosphate (10-MDP), 2-(meth)acryloyloxyethyl dihydrogen phosphate, 6-(meth)acryloyloxyhexyl dihydrogen phosphate, 4-(meth)acryloyloxybutyl dihydrogen phosphate, 8-(meth)acryloyloxyoctyl dihydrogen phosphate, 2-(meth)acryloyloxynonyl dihydrogen phosphate, 11-(meth)acryloyloxyundecyl dihydrogen-phosphate, 20-(meth)acryloyloxyeicosyl dihydrogen phosphate, 1,3-di(meth)acyloyloxypropyl-2-dihydrogen phosphate, 2-(meth)acryloyloxyethylphenyl dihydrogen phosphate, di(2-(meth)acyloyloxyethyl)pyrophosphate, di (2-(meth)acyloyloxypropyl) pyrophosphate, di (2-(meth)acyloyloxybutyl) pyrophosphate, di (2-(meth)acyloyloxypentyl) pyrophosphate, di (2-(meth)acyloyloxyhexyl) pyrophosphate, di(2-(meth)acyloyloxydecyl) pyrophosphate, mono-, di- and/or triester of the phosphoric acid with hydroxy-C2-C8-alkyl methacrylate, glycerol dimethacrylate phosphate, pentaerythritol trimethacrylate phosphate, dipentaerythritol pentaacrylate phosphate, tetramethacryloxyethyl pyrophosphate, 4-Methacryloyloxyethyl trimellitic acid (4-MET), 4-ethacryloxyethyltrimelliticanhydride (4-META), pyromellitic acid dimethacrylate, pyromellitic glycerol dimethacrylate, methacryloyloxyethyl phthalate, methacryloyloxyethyl maleate, methacryloyloxyethyl succinate, 1,3-glyceroldimethacrylate maleate and glycine-N,N'-1,2-ethanediylbis [N-(carboxymethyl)-1, 1 '-bis [2-[(2-methyl-1-oxo-2-propen-1-yl)oxy] ethyl.

5. The polymerizable dental composition as claimed in claim 2, wherein the component (F) additives are selected from the group consisting of rheological auxiliaries, colorants, aromas, stabilizers, inhibitors, molecular weight regulators, preservatives, interface-active substances, microbicides, organic polymers and oligomers and compounds having high molecular weights, thickeners, dental medicaments, and plasticizers.

6. The polymerizable dental composition as claimed in claim 2, wherein the component (G) solvents are selected from the group consisting of water, toluene, xylene, isooctane, acetone, butanone, methyl isobutyl ketone, ethyl acetate, butyl acetate, tetrahydrofuran, N-methylpyrrolidone, dimethylacetamine and dimethylformamide, ethanol, propanols, butanols, pentanols, hexanols, cyclohexanol, heptanols, octanols, nonanols, decanols, water miscible organic solvents, and mixtures thereof, wherein the ratio of the organic solvent(s)/mixture to water is in the range of 1:1 to 10:1.

7. The polymerizable dental composition as claimed in claim 2, wherein
the refractive index $n_A$ of the total amount of the components (A) and (D) is in the range of 1.45 to 1.55,
the refractive index $n_B$ of the total amount of the fillers (B) is in the range of 1.50 to 1.55,
the amount of difference $|n_A-n_B|$ between the refractive index $n_A$ of the total amount of the components (A) and (D) and the refractive index $n_B$ of the total amount of the fillers (B) is smaller than 0.05, and/or
the difference $n_P-n_A$ of the refractive index $n_P$ of a polymerized resin matrix obtained following polymerization of the polymerizable dental composition (from components (A) and (D)) and the refractive index $n_A$ of the total amount of the components (A) and (D), before the polymerization is smaller than 0.03.

8. The polymerizable dental composition as claimed in claim 1, wherein the composition comprises:
the component (A) polysiloxanes in an amount of 5 to 99.69% by weight,
the component (B) fillers in an amount of 0.3 to 92% by weight,
the component (C) initiators, catalysts, activators, or combinations thereof in an amount of 0.01 to 5% by weight,
(D) organic, polymerizable monomers, which are not component (A) polysiloxanes, in an amount of 0 to 94% by weight,
(E) organic monomers containing acid groups without any Si-atom in an amount of 0 to 20% by weight,
(F) additives in an amount of 0 to 20% by weight, and
(G) solvents in an amount of 0 to 70% by weight, and
wherein the weights are based on the respective overall composition.

9. The polymerizable dental composition as claimed in claim 1, wherein the group Y in silane (a1) is selected from the group consisting of $-(X)_x-C(=O)NH-$, $-NHC(=O)-(X)_x-$ and $-(X)_xC(=O)N(-C(=O)NH-)-$ wherein X is selected from the group consisting of O, S and NH, and wherein the index x is either 0 or 1, and wherein the polymerizable group PG is selected from the group consisting of $-CH=CH_2$, $-C(CH_3)=_cH_2$, $-C(=O)-CH=CH_2$, $-C(=O)-C(CH_3)=CH_2$, $-Z-C(=O)-CH=CH_2$ and $-Z-C(=O)-C(CH_3)=CH_2$, and wherein Z is selected from the group consisting of O and NH.

10. The polymerizable dental composition as claimed in claim 1, wherein the fillers (B) comprise organic fillers inorganic fillers, or combinations thereof,
wherein the organic fillers are selected from the group consisting of polyvinyl acetate and copolymers of polyvinyl acetate with one or more polymerizable compounds, polystyrene, polyethylene, polypropylene, waxes polybutylene, polybutadiene, copolymers of butadiene and styrene, polyacrylonitrile, resins poly (meth)acrylate esters, polydialkyl maleates and copolymers thereof, and polymers containing silyl groups, wherein the organic fillers can be used alone or as mixtures,
wherein the inorganic fillers are selected from the group consisting of amorphous materials based on mixed oxides composed of $SiO_2$, $ZrO_2$ and/or $TiO_2$ quartz glass ceramic, glass powder, barium silicate glasses, barium fluorosilicate glasses, strontium silicate glasses, strontium borosilicate, Li/Al silicate glasses, barium glasses, calcium silicates, sodium aluminosilicates, fluoroaluminosilicate glasses, oxides of aluminum, zirconium or silicon, zeolites, apatite, zirconium silicate, barium sulfate, calcium fluoride, ytterbium fluoride and strontium fluoride,
wherein the inorganic fillers are organically surface-modified and
wherein the inorganic fillers have a proportion of nanoscale particles in the range from 1 nm to 200 nm and a proportion of macroscopic particles in the range from 0.4 μm to 10 μm.

11. The polymerizable dental composition as claimed in claim 10, wherein the nanoscale particles have an average particle size of not more than 100 nm, and
wherein the nanoscale particles are in nonagglomerated and/or nonaggregated form, and wherein
the macroscopic particles have one or more first microparticle fractions each having an average particle size in the range from 1 μm to 10 μm, and one or more second microparticle fractions each having an average particle size in the range from greater 0.4 μm to less than 1 μm and wherein the ratio of the total mass of the first microparticle fractions to the total mass of the second microparticle fractions is in the range from 1:1 to 12:1, and wherein the ratio of the average particle size of the first microparticle fraction to the average particle size of the second microparticle fraction of the component is in the range from 1.5:1 to 10:1 preferably in the range from 2:1 to 5:1.

12. The polymerizable dental composition as claimed in claim 1, wherein Y is selected from the group consisting of —C(=O)NH—, —NHC(=O)—, —OC(=O)NH—, —NHC(=O)O—, —SC(=O)NH—, —NHC(=O)S—, —NHC(=O)NH—, —OC(=O)N(—C(=O)NH—)—, —SC(=O)N(—C(=O)NH—)—, —NHC(=O)N(—C(=O)NH—)—, —C(=O)NHC(=O)NH—, —NHC(=O)NHC(=O)—, wherein the bond arranged on the left in each formula is closer to the structural element A and the bond arranged to the right is closer to the structural element B.

13. A cured dental material obtainable by polymerization of the polymerizable dental composition as claimed in claim 1.

14. A method for temporarily or permanently filling a dental cavity, the method comprising using the polymerizable dental composition as claimed in claim 1 as stable filling composite, stable bulk-fill material, inlay, onlay, overlay, dental block material, false teeth, dental framework, flowable filling composite, flowable bulk-fill material, core build-up material, luting cement, crown and bridge material, orthodontic material, base material or relining material, dental adhesive, dental sealing material, dental lacquer, dental primer or dental printing composition in additive manufacturing methods.

15. The method of claim 14, wherein the polymerizable dental composition is used as stable filling composite, stable bulk-fill material, inlay, onlay, overlay, dental block material, false teeth, or dental framework, and wherein the polymerizable dental composition comprises:
the component (A) polysiloxanes in an amount of 5 to 19.99% by weight,
the component (B) fillers in an amount of 80 to 92% by weight,
the component (C) initiators, catalysts, activators, or combinations thereof in an amount of 0.01 to 5% by weight,
(D) organic polymerizable monomers which are not component (A) polysiloxanes in an amount of 0 to 14% by weight, and
(F) additives in an amount of 0 to 8% by weight,
wherein the weights are based on the respective overall composition.

16. The method of claim 14, wherein the polymerizable dental composition is used as flowable filling composite, flowable bulk-fill material, core build-up material, luting cement, crown and bridge material, orthodontic material, base material, or relining material, and wherein the polymerizable dental composition comprises:
the component (A) polysiloxanes in an amount of 5 to 49.99% by weight,
the component (B) fillers in an amount of 50 to 80% by weight,
the component (C) initiators, catalysts, activators, or combinations thereof in an amount of 0.01 to 5% by weight,
(D) organic polymerizable monomers which are not component (A) polysiloxanes in an amount of 0 to 35% by weight,
(E) organic monomers containing acid groups without any Si-atom in an amount of 0 to 20% by weight, and
(F) additives in an amount of 0 to 20% by weight,
wherein the weights are based on the respective overall composition.

17. The method of claim 14, wherein the polymerizable dental composition is used as dental adhesive, dental sealing material, dental lacquer, dental primer, or dental printing composition in additive manufacturing methods, and wherein the polymerizable dental composition comprises:
the component (A) polysiloxanes in an amount of 5 to 99.69% by weight,
the component (B) fillers in an amount of 0.3 to 50% by weight,
the component (C) initiators, catalysts, activators, or combinations thereof in an amount of 0.01 to 5% by weight,
(D) organic polymerizable monomers which are not component (A) polylsiloxanes in an amount of 0 to 94% by weight,
(E) organic monomers containing acid groups without Si atoms in an amount of 0 to 20% by weight,
(F) additives in an amount of 0 to 20% by weight, and
(G) solvents in an amount of 0 to 70% by weight,
wherein the weights are based on the respective overall composition.

18. A method for producing the polymerizable dental composition as claimed in claim 1 comprising the following steps:
providing components (A), (B), (C), and optionally the components (D) organic polymerizable monomers which are not component (A) polysiloxanes, (E) organic monomers containing acid groups without any Si-atom, (F) additives, (G) solvents, or combinations thereof, and
mixing the components.

19. A method for producing the polymerized, dental composition as claimed in claim 13 comprising the following steps:
providing components (A), (B), (C), and optionally the components (D) organic polymerizable monomers which are not component (A) polysiloxanes, (E) organic monomers containing acid groups without any Si-atom, (F) additives, (G) solvents, or combinations thereof,
mixing the components, and
polymerizing the mixture.

20. A kit, comprising
at least one polymerizable dental composition as claimed in claim 1 in a syringe and/or compule,
optionally at least one adhesives,
optionally at least one etching gels,
optionally at least one shade guide,
optionally at least one brush.

* * * * *